United States Patent
Brandl et al.

(10) Patent No.: US 12,338,249 B2
(45) Date of Patent: Jun. 24, 2025

(54) CRYSTALLINE FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO[2,3-D]PYRIMIDIN-6-YL)PHENYL)-N'-METHOXYUREA

(71) Applicants: Sumitomo Pharma Switzerland GmbH, Basel (CH); Takeda Pharmaceutical Company Limited, Osaka (JP)

(72) Inventors: Michael Thomas Brandl, Redwood City, CA (US); Patricia Andres, Bend, OR (US); Petinka I. Vlahova, West Lafayette, IN (US); Tsuyoshi Sasaki, Osaka (JP)

(73) Assignees: Sumitomo Pharma Switzerland GmbH, Basel (CH); Takeda Pharmaceutical Company Limited, Osaka (JP)

( * ) Notice: Subject to any disclaimer, the term of this patent is extended or adjusted under 35 U.S.C. 154(b) by 658 days.

(21) Appl. No.: 17/716,963

(22) Filed: Apr. 8, 2022

(65) Prior Publication Data

US 2022/0396582 A1 Dec. 15, 2022

Related U.S. Application Data

(63) Continuation of application No. PCT/EP2020/078493, filed on Oct. 9, 2020.

(60) Provisional application No. 62/913,560, filed on Oct. 10, 2019.

(51) Int. Cl.
*C07D 495/04* (2006.01)

(52) U.S. Cl.
CPC ........ *C07D 495/04* (2013.01); *C07B 2200/13* (2013.01)

(58) Field of Classification Search
CPC .......... C07D 495/04; C07B 2200/13
See application file for complete search history.

(56) References Cited

U.S. PATENT DOCUMENTS

| | | | |
|---|---|---|---|
| 3,872,115 A | 3/1975 | Sugimoto et al. |
| 5,312,958 A | 5/1994 | Suenaga et al. |
| 6,297,379 B1 | 10/2001 | Furuya et al. |
| 6,340,686 B1 | 1/2002 | Furuya et al. |
| 7,300,935 B2 | 11/2007 | Cho et al. |
| 7,569,570 B2 | 8/2009 | Furuya et al. |
| 8,058,280 B2 | 11/2011 | Cho et al. |
| 8,735,401 B2 | 5/2014 | Cho et al. |
| 9,346,822 B2 | 5/2016 | Cho et al. |
| 9,758,528 B2 | 9/2017 | Fukuoka et al. |
| 10,150,778 B2 | 12/2018 | Miwa |
| 10,160,765 B2 | 12/2018 | Enlow et al. |
| 10,350,170 B2 | 7/2019 | Yamane et al. |
| 10,449,191 B2 | 10/2019 | Rajasekhar et al. |
| 10,464,945 B2 | 11/2019 | Miwa |
| 10,544,160 B2 | 1/2020 | Miwa |
| 10,689,359 B2 | 6/2020 | Shu et al. |
| 10,786,501 B2 | 9/2020 | Rajasekhar et al. |
| 11,033,551 B2 | 6/2021 | Johnson et al. |
| 11,053,257 B2 | 7/2021 | Miwa |
| 11,583,526 B2 | 2/2023 | Rajasekhar et al. |
| 11,655,256 B1 | 5/2023 | Paschalides |
| 11,731,983 B2 | 8/2023 | Miwa |
| 11,793,812 B2 | 10/2023 | Johnson et al. |
| 11,795,178 B2 | 10/2023 | Fukuoka et al. |
| 11,957,684 B2 | 4/2024 | Johnson et al. |
| 12,097,198 B2 | 9/2024 | Rajasekhar et al. |
| 2003/0055269 A1 | 3/2003 | Fukuoka et al. |
| 2004/0014634 A1 | 1/2004 | Bantick et al. |
| 2006/0160829 A1 | 7/2006 | Cho et al. |
| 2008/0287465 A1 | 11/2008 | Tumey et al. |
| 2009/0048273 A1 | 2/2009 | Furuya et al. |
| 2011/0172249 A1 | 7/2011 | Kamikawa et al. |
| 2015/0266891 A1 | 9/2015 | Fukuoka et al. |
| 2017/0210753 A1 | 7/2017 | Fukuoka et al. |
| 2019/0224196 A1 | 7/2019 | Rajasekhar et al. |
| 2019/0262346 A1 | 8/2019 | Johnson et al. |
| 2020/0000730 A1 | 1/2020 | Yamane et al. |
| 2021/0205303 A1 | 7/2021 | Rajasekhar et al. |
| 2021/0401841 A1 | 12/2021 | Johnson et al. |
| 2022/0135585 A1 | 5/2022 | Miwa |
| 2022/0204525 A1 | 6/2022 | Fukuoka et al. |
| 2022/0227784 A1 | 7/2022 | Kantor et al. |
| 2022/0372044 A1 | 11/2022 | Jagusch et al. |
| 2023/0165800 A1 | 6/2023 | Alonzo et al. |
| 2023/0212184 A1 | 7/2023 | Fukuoka et al. |
| 2024/0165118 A1 | 5/2024 | Johnson et al. |

FOREIGN PATENT DOCUMENTS

| | | | |
|---|---|---|---|
| CA | 3010509 A1 | 7/2017 |
| CN | 87101864 A | 11/1987 |
| CN | 1349536 A | 5/2002 |
| CN | 1406239 A | 3/2003 |

(Continued)

OTHER PUBLICATIONS

Byrn, S. et al. (1995). "Pharmaceutical solids: A Strategic Approach to Regulatory Considerations," Pharma. Res. 12:945-954.

(Continued)

*Primary Examiner* — Joseph K McKane
*Assistant Examiner* — Quincy McKoy
(74) *Attorney, Agent, or Firm* — Cooley LLP

(57) ABSTRACT

This disclosure relates to novel crystalline forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea. It also relates to methods of making the disclosed crystalline forms, pharmaceutical compositions and kits comprising them, and methods of treatment and uses comprising their administration.

20 Claims, 33 Drawing Sheets

(56) References Cited

FOREIGN PATENT DOCUMENTS

| | | |
|---|---|---|
| CN | 1551883 A | 12/2004 |
| CN | 1761671 A | 4/2006 |
| CN | 1768065 A | 5/2006 |
| CN | 101048065 A | 10/2007 |
| CN | 111333633 A | 6/2020 |
| CN | 111423452 A | 7/2020 |
| CN | 112552312 A | 3/2021 |
| CN | 115417883 A | 12/2022 |
| CN | 115947734 A | 4/2023 |
| EP | 1 266 898 A1 | 12/2002 |
| EP | 1 591 446 A1 | 11/2005 |
| EP | 3 666 776 A1 | 6/2020 |
| IN | 31/2023 | 8/2023 |
| JP | H-06-192170 A | 7/1994 |
| JP | H-10-298156 A | 11/1998 |
| JP | 2001-278884 A | 10/2001 |
| JP | 2001-316391 A | 11/2001 |
| JP | 2002-088044 A | 3/2002 |
| JP | 2010-229098 A | 10/2010 |
| JP | 2015-532262 A | 11/2015 |
| JP | 2016-041720 A | 3/2016 |
| JP | 2017-088564 A | 5/2017 |
| JP | 2018-538348 A | 12/2018 |
| JP | 2019-038825 A | 3/2019 |
| JP | 2019-511510 A | 4/2019 |
| WO | WO-00/56739 A1 | 9/2000 |
| WO | WO-2004/067535 A1 | 8/2004 |
| WO | WO-2007/011072 A1 | 1/2007 |
| WO | WO-2010/026993 A1 | 3/2010 |
| WO | WO-2014/051164 A2 | 4/2014 |
| WO | WO-2014/051164 A3 | 4/2014 |
| WO | WO-2017/172615 A1 | 10/2017 |
| WO | WO-2018/060463 A2 | 4/2018 |
| WO | WO-2018/060463 A3 | 4/2018 |
| WO | WO-2018/060501 A2 | 4/2018 |
| WO | WO-2018/060501 A3 | 4/2018 |
| WO | WO-2019/178304 A1 | 9/2019 |
| WO | WO-2020/230094 A1 | 11/2020 |
| WO | WO-2021/026011 A1 | 2/2021 |
| WO | WO-2021/027937 A1 | 2/2021 |
| WO | WO-2021/031148 A1 | 2/2021 |
| WO | WO-2021/069700 A1 | 4/2021 |
| WO | WO-2021/069711 A1 | 4/2021 |
| WO | WO-2021/239917 A1 | 12/2021 |
| WO | WO-2022/101303 A1 | 5/2022 |
| WO | WO-2022/166121 A1 | 11/2022 |
| WO | WO-2023/042214 A1 | 3/2023 |
| WO | WO-2023/066941 A1 | 4/2023 |
| WO | WO-2023/119333 A1 | 6/2023 |
| WO | WO-2023/194924 A1 | 10/2023 |

OTHER PUBLICATIONS

Caira, M.R. (1998). "Crystalline polymorphism of organic compounds," Topics in Curr. Chem. 198:163-208.
Chinese Office Action mailed on Nov. 17, 2016, for Chinese patent application No. 201380051107.2, filed on Sep. 27, 2013, 14 pages (with English translation).
Ex Parte Quayle Action mailed on Jun. 5, 2018, for U.S. Appl. No. 15/481,505, filed Apr. 7, 2017, 4 pages.
Extended European Search Report mailed on Nov. 9, 2018, for EP Application No. 18 185 835.8, filed on Sep. 27, 2013, 5 pages.
Holzer, G. et al. (1997). "$K\alpha_{1,2}$ and $K\beta_{1,3}$ X-ray emission lines of the 3d transition metals," Phys. Rev. A56(6):4554-4568.
International Search Report mailed on Mar. 24, 2014, for PCT Application No. PCT/JP2013/077013, filed on Sep. 27, 2013, 7 pages.
International Search Report mailed on Jan. 25, 2021, for PCT Application No. PCT/EP2020/078493, filed on Oct. 9, 2020, 6 pages.
International Search Report mailed on Jan. 25, 2021, for PCT Application No. PCT/EP2020/078475, filed on Oct. 9, 2020, 6 pages.
Liu Xin-yong et al. (2011). Laboratory Preparation, Separation and Purification Technology of Organic Compounds, People's Medical Publishing House, pp. 103-106 (with English translation).
Miwa, K. et al. (2011). "Discovery of 1-{4-[1-(2,6-Difluorobenzyl)-5-[(dimethylamino)methyl]-3-(6-methoxypyridazin-3-yl)-2,4-dioxo-I,2,3,4-tetrahydrothieno[2,3- d ]pyrimidin-6-yl]phenyl}-3-methoxyurea (TAK-385) as a Potent, Orally Active, Non-Peptide Antagonist of the Human Gonadotropin-Releasing Hormone Receptor," J. Med. Chem. 54:4998-5012.
Non-Final Office Action mailed on May 12, 2016, for U.S. Appl. No. 14/432,188, filed Mar. 27, 2015, 4 pages.
Non-Final Office Action mailed on Nov. 21, 2017, for U.S. Appl. No. 15/481,505, filed Apr. 7, 2017, 7 pages.
Non-Final Office Action mailed on Mar. 22, 2019, for U.S. Appl. No. 16/034,002, filed Jul. 12, 2018, 4 pages.
Non-Final Office Action mailed on Jun. 6, 2019, for U.S. Appl. No. 16/116,804, filed Aug. 29, 2018, 6 pages.
Non-Final Office Action mailed on Aug. 24, 2020, for U.S. Appl. No. 16/710,390, filed Dec. 11, 2019, 4 pages.
Notice of Allowance mailed on May 17, 2017, for U.S. Appl. No. 14/432,188, filed Mar. 27, 2015, 5 pages.
Notice of Allowance mailed on Sep. 17, 2018, for U.S. Appl. No. 15/481,505, filed Apr. 7, 2017, 5 pages.
Notice of Allowance mailed on Jul. 3, 2019, for U.S. Appl. No. 16/034,002, filed Jul. 12, 2018, 5 pages.
Notice of Allowance mailed on Sep. 12, 2019, for U.S. Appl. No. 16/116,804, filed Aug. 29, 2018, 6 pages.
Notice of Allowance mailed on Nov. 26, 2019, for U.S. Appl. No. 16/116,804, filed Aug. 29, 2018, 2 pages.
Notice of Allowance mailed on Mar. 10, 2021, for U.S. Appl. No. 16/710,390, filed jon Dec. 11, 2019, 6 pages.
Written Opinion of the International Searching Authority mailed on Mar. 24, 2014, for PCT Application No. PCT/JP2013/077013, filed on Sep. 27, 2013, 10 pages.
Written Opinion of the International Searching Authority mailed on Jan. 25, 2021, for PCT Application No. PCT/EP2020/078493, filed on Oct. 9, 2020, 10 pages.
Written Opinion of the International Searching Authority mailed on Jan. 25, 2021, for PCT Application No. PCT/EP2020/078475, filed on Oct. 9, 2020, 11 pages.
Yang, Lv et al. (2009). Polymorphic Drugs, People's Medical Publishing House, pp. 24-25 (with English translation).
U.S. Appl. No. 17/349,584, filed Jun. 16, 2021, by Fukuoka et al.
U.S. Appl. No. 17/716,965, filed Apr. 8, 2022, by Jagusch et al.
Corrected Notice of Allowability mailed on Jul. 12, 2023, for U.S. Appl. No. 17/349,584, filed Jun. 16, 2021, 2 pages.
Corrected Notice of Allowability mailed on Sep. 1, 2023, for U.S. Appl. No. 17/694,635, filed Mar. 14, 2022, 2 pages.
Ding, Z. et al. (Oct. 22, 2018). "Crystalline forms," Chinese Pharmaceutical Journal, pp. 85 (with English Translation).
Extended European Search Report mailed on Nov. 25, 2022, for EP Application No. 22 168 256.0, filed on Sep. 27, 2013, 8 pages.
Guo, Z. et al. (2003). "Synthesis and structure-activity relationships of Thieno[2,3-d]pyrimidine-2,4-dione derivatives as potent GnRH receptor antagonists," Bioorganic & Medicinal Chemistry Letters 13:3617-3622.
Hirayama, N. (2008). Organic Compound Crystal Production Handbook, 32 pages (English Summary Provided).
Huang Li et al. (Nov. 18, 2018). "Progress in the study of new drug therapies for endometriosis," The Journal of Practical Medicine, vol. 34, No. 21, pp. 164-167 (with English Abstract Provided).
International Search Report mailed on Jan. 26, 2023, for PCT Application No. PCT/EP2022/078989, filed on Oct. 18, 2022, 4 pages.
Kumar, J.S. et al. (2001). "Simple and chemoselective reduction of aromatic nitro compounds to aromatic amines: Reduction with hydriodic acid revisited," Tetrahedron Letter 42:5601-5603.
Non-Final Office Action mailed on Apr. 10, 2023, for U.S. Appl. No. 17/349,584, filed Jun. 16, 2021, 7 pages.
Non-Final Office Action mailed on Jul. 18, 2024, for U.S. Appl. No. 18/121,886, filed Mar. 15, 2023, 6 pages.
Notice of Allowance mailed on May 10, 2023, for U.S. Appl. No. 17/349,584, filed Jun. 16, 2021, 5 pages.

(56) References Cited

OTHER PUBLICATIONS

Notice of Allowance mailed on Aug. 17, 2023, for U.S. Appl. No. 17/694,635, filed Mar. 14, 2022, 6 pages.
Notice of Allowance mailed on Aug. 21, 2024, for U.S. Appl. No. 18/121,886, filed Mar. 15, 2023, 5 pages.
Sasaki, S. et al. (2002). "Discovery of a thieno[2,3-d]pyrimidine-2,4-dione bearing a p-methoxyureidophenyl moiety at the 6-position: a highly potent and orally bioavailable non-peptide antagonist for the human luteinizing hormone-releasing hormone receptor ," J. Med. Chem. 46:113-124.
Serizawa, K. (2002). Optimization of salt and crystal forms and crystallization techniques, Pharm. Tech. Japan, vol. 18, No. 10, pp. 81-96 (with English Abstract Provided).
Written Opinion of the International Searching Authority mailed on Jan. 26, 2023, for PCT Application No. PCT/EP2022/078989, filed on Oct. 18, 2022, 8 pages.
Zhang Hongli et al. (Dec. 31, 2016). "Microstructure and performance in the desolvation process of HNS/dioxane solvate by In-situ XRD method," Chinese Journal of Energetic Materials, vol. 24, No. 4, pp. 363-367 (with English Abstract Provided).
U.S. Appl. No. 18/195,654, filed May 10, 2023, by Migoya et al.
U.S. Appl. No. 18/392,110, filed Dec. 21, 2023, by Migoya et al.
U.S. Appl. No. 18/427,033, filed Jan. 30, 2024, by Johnson et al.
U.S. Appl. No. 18/636,642, filed Apr. 16, 2024, by Vlahova et al.
U.S. Appl. No. 18/758,904, filed Jun. 28, 2024, by Rajasekhar et al.
U.S. Appl. No. 18/792,752, filed Aug. 2, 2024, by Rajasekhar et al.
U.S. Appl. No. 18/797,045, filed Aug. 7, 2024, by Migoya et al.
U.S. Appl. No. 18/926,157, filed Oct. 24, 2024, by Johnson et al.
U.S. Appl. No. 18/927,346, filed Oct. 25, 2024, by Miwa.

US 12,338,249 B2

CRYSTALLINE FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO[2,3-D]PYRIMIDIN-6-YL)PHENYL)-N'-METHOXYUREA

CROSS-REFERENCE TO RELATED APPLICATIONS

This application is a continuation of PCT Patent Application Serial No. PCT/EP2020/078493, filed on Oct. 9, 2020, which claims the benefit of U.S. Provisional Application Ser. No. 62/913,560, filed on Oct. 10, 2019, the entire disclosure of each of which is incorporated herein by reference in its entirety.

This disclosure relates to novel crystalline forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, also referred to herein as Compound 1. It also relates to methods of making the disclosed crystalline forms, pharmaceutical compositions and kits comprising them, and methods of treatment and uses comprising their administration.

BACKGROUND

Compound 1, N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, is a gonadotropin-releasing hormone (GnRH) antagonist being developed as a new pharmaceutical agent useful for treating various conditions including heavy menstrual bleeding and other symptoms associated with uterine fibroids, pain and other symptoms associated with endometriosis, and prostate cancer. Compound 1 may also useful to treat other diseases or disorders. See, e.g., U.S. Pat. Nos. 7,300,935, 8,058,280, 8,735,401, 9,346,822, WO2018060501, and WO2018060463.

Compound 1 and methods of preparing Compound 1 are described in U.S. Pat. Nos. 7,300,935, 8,058,280, 8,735,401, 9,346,822, and 9,758,528.

U.S. Pat. No. 9,758,528, which is herein incorporated by reference in its entirety, describes methods for producing Compound 1 and certain synthetic intermediates, as well as two crystalline forms of Compound 1: a crystal of a tetrahydrofuran solvate of Compound 1 and a crystal of an anhydrous form of Compound 1 (referred to herein as Form I of Compound 1). For reference, as detailed in U.S. Pat. No. 9,758,528, Form I of Compound 1 may be characterized by an XRPD pattern having peaks at approximately 7.4°, 8.9°, 9.9°, 12.1°, 16.6°, 17.3°, 22.2°, 22.8°, and 27.4° 2θ.

Form I of Compound 1 may also be characterized by the XRPD pattern depicted in FIG. 25 of the present application. Form I of Compound 1 begins to melt at about 189° C. and begins to degrade at about 197° C. Form I of Compound 1 shows an exothermic peak at about 237° C. by DSC with degradation at about 245° C. by TG. FIGS. 28 and 29 show the thermogravimetry (TG) and differential scanning calorimetry (DSC) thermograms, respectively, of Form I of Compound 1.

SUMMARY

An aspect of the disclosure relates to a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form II of Compound 1. In some embodiments, Form II of Compound 1 is characterized by an X-ray power diffraction pattern comprising at least three peaks selected from the group consisting of 9.7°, 10.7°, 19.0°, 19.3° and 20.9° 2θ±0.2° 2θ. In some embodiments, Form II of Compound 1 is characterized by an X-ray power diffraction pattern comprising at least five peaks selected from the group consisting of 7.2°, 9.7°, 10.7°, 13.1°, 15.7°, 19.0°, 19.3° and 20.9° 2θ±0.2° 2θ. In some embodiments, Form II of Compound 1 is characterized by an X-ray power diffraction pattern comprising peaks at 9.7°, 10.7°, 19.0°, 19.3° and 20.9° 2θ±0.2° 2θ. In certain such embodiments, the X-ray power diffraction pattern comprises one or more peaks selected from the group consisting of 7.2°, 13.1° and 15.7°±0.2° 2θ. In some embodiments, Form II of Compound 1 is by an XRPD pattern substantially the same as the pattern shown in FIG. 1.

In some embodiments, Form II of Compound 1 is characterized by an onset of degradation between about 174° C. and about 176° C. In some embodiments, Form II of Compound 1 is characterized by an onset of degradation at about 175° C. In some embodiments, Form II of Compound 1 is characterized by a thermogravimetry (TG) thermogram substantially the same as the pattern shown in FIG. 2.

In some embodiments, Form II of Compound 1 is characterized by an onset of melting between about 179° C. and about 181° C. In some embodiments, Form II of Compound 1 is characterized by an onset of melting at about 180° C. In some embodiments, Form II of Compound 1 is characterized by a differential scanning calorimetry (DSC) thermogram comprising an exothermic peak between about 191° C. and about 194° C. In some embodiments, Form II of Compound 1 is characterized by a DSC thermogram comprising an exothermic peak at about 192° C. In some embodiments, Form II of Compound 1 is characterized by a DSC thermogram substantially the same as the pattern shown in FIG. 3.

In some embodiments, Form II of Compound 1 is characterized by having at least two of the following:
  a) an XRPD pattern comprising at least three peaks selected from the group consisting of 9.7°, 10.7°, 19.0°, 19.3° and 20.9° 2θ±0.2° 2θ;
  b) an onset of degradation at about 175° C. as measured by TG; and
  c) an exothermic peak at about 192° C. as measured by DSC.

An aspect of the disclosure relates to a pharmaceutical composition comprising a crystalline form of the disclosure and a pharmaceutically acceptable carrier.

Another aspect of the disclosure relates to a method for preparing Form II of Compound 1, said method comprising:
  a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in a mixture of DMF and acetone (about 6:94, v/v) at about 25° C. to form a solution;
  b) stirring the solution at a temperature of about −15° C. to about −25° C. for about 3 days to generate a suspension; and
  c) isolating solids from the suspension by vacuum filtration to afford Form II of Compound 1.

This method may comprise vacuum drying the isolated solids at about 60° C. for about 4 hours to afford the Form II of Compound 1.

DETAILED DESCRIPTION

Described herein are novel crystalline forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (Compound 1), methods of making them, pharmaceutical compositions and kits comprising them, and methods of treatment and uses comprising their administration. The chemical structure of Compound 1 is as follows:

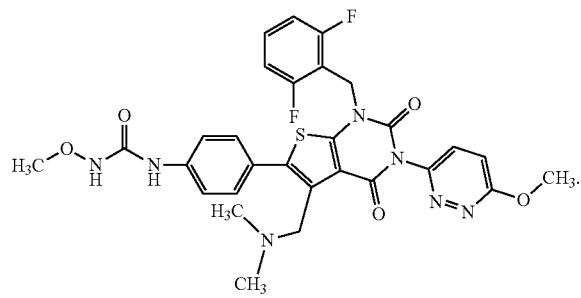 [SMILES: CONC(=O)Nc1ccc(-c2sc3c(c2CN(C)C)c(=O)n(-c2ccc(OC)nn2)c(=O)n3Cc2c(F)cccc2F)cc1]

General Information

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Crystalline Forms of the Disclosure

Table 1 lists the various crystalline forms described herein. As used herein, the term "solvate" includes stoichiometric solvates and non-stoichiometric solvates, such as channel-type solvates, formed by Compound 1 and solvent. Examples of suitable solvents may include, but are not limited to, water, toluene, THF, anisole, isopropanol, dioxane, α,α,α-trifluorotoluene, and trifluoroethanol. Solvates wherein water is the solvent molecule are typically referred to as hydrates. Hydrates may include compositions containing stoichiometric amounts of water, as well as compositions containing variable amounts of water. As will be understood by the skilled artisan, unlike stoichiometric hydrates, the dehydration and rehydration of non-stoichiometric hydrates is not accompanied by a phase transition, and thus all hydration states typically represent the same crystal form.

TABLE 1

Crystalline Forms of Compound 1

| Name | Comments |
|---|---|
| Form II | Anhydrate |
| Form III | Hemihydrate |
| Form IV | Not isolable |
| Form V | Toluene solvate |
| Form VI | Anisole solvate |

TABLE 1-continued

Crystalline Forms of Compound 1

| Name | Comments |
|---|---|
| Form VII | Isopropyl alcohol solvate |
| Form VIII | Dioxane solvate |
| Form IX | α,α,α-Trifluorotoluene solvate |
| Form X | Trifluoroethanol solvate |
| Form XI | DMF solvate |
| Form XII | Acetone solvate |

Form II of Compound 1

Figure 1:
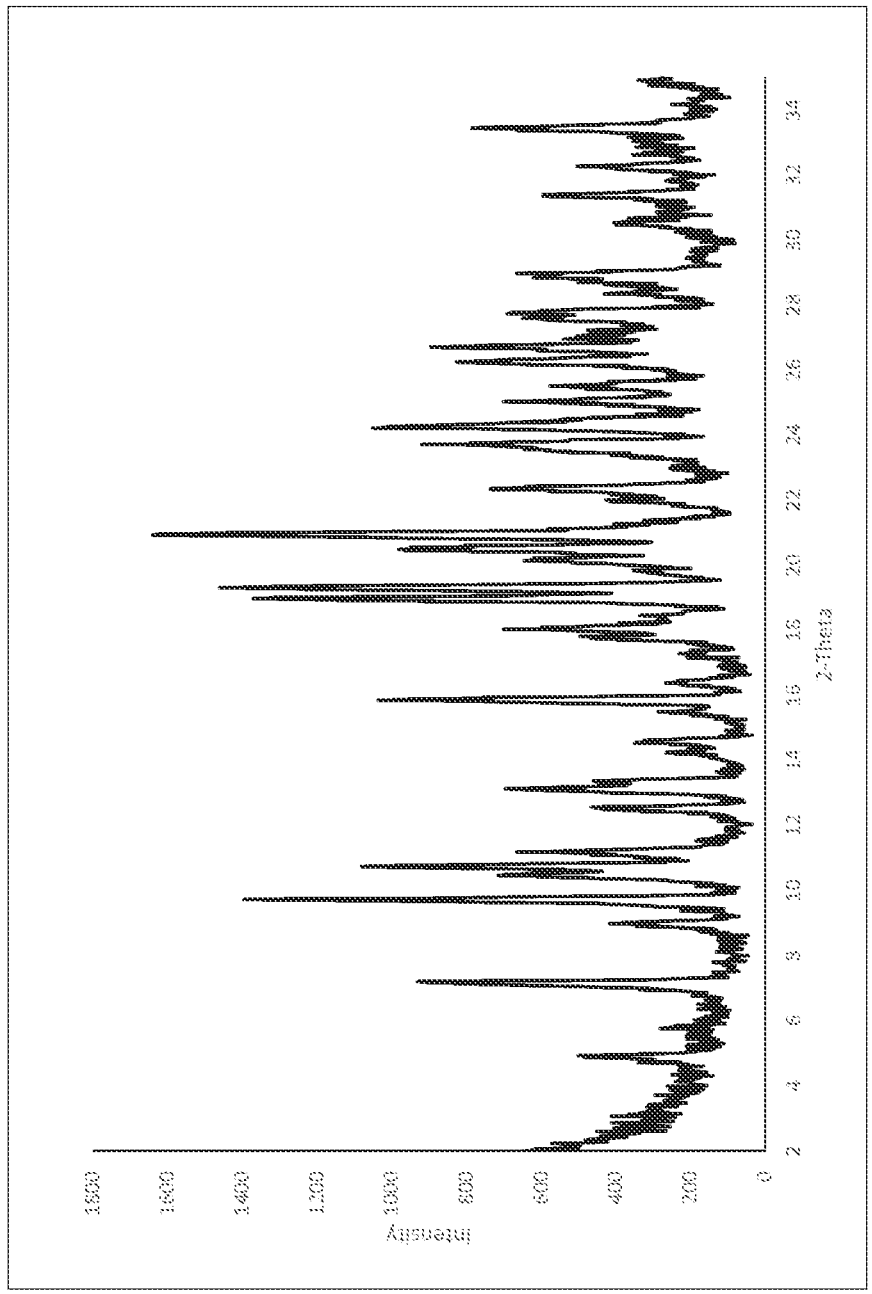
FIG. 1 depicts a powder X-ray diffraction pattern of Form II of Compound 1.

The present disclosure provides a crystalline form of Compound 1 characterized as Form II of Compound 1. In some embodiments, Form II of Compound 1 is an anhydrate. In some embodiments, Form II of Compound 1 is characterized by an XRPD pattern comprising at least three peaks selected from the group consisting of 9.7°, 10.7°, 19.0°, 19.3° and 20.9° 2θ±0.2° 2θ. In some embodiments, Form II of Compound 1 is characterized by an XRPD pattern comprising at least five peaks selected from the group consisting of 7.2°, 9.7°, 10.7°, 13.1°, 15.7°, 19.0°, 19.3° and 20.9° 2θ±0.2° 2θ. In some embodiments, Form II of Compound 1 is characterized by an XRPD pattern having peaks at 9.7°, 10.7°, 19.0°, 19.3° and 20.9° 2θ±0.2° 2θ. In certain such embodiments, the XRPD pattern has one or more peaks selected from the group consisting of 7.2°, 13.1°, and 15.7°±0.2° 2θ. In some embodiments, Form II of Compound 1 is characterized by an XRPD pattern substantially the same as the pattern shown in FIG. 1.

Figure 2:
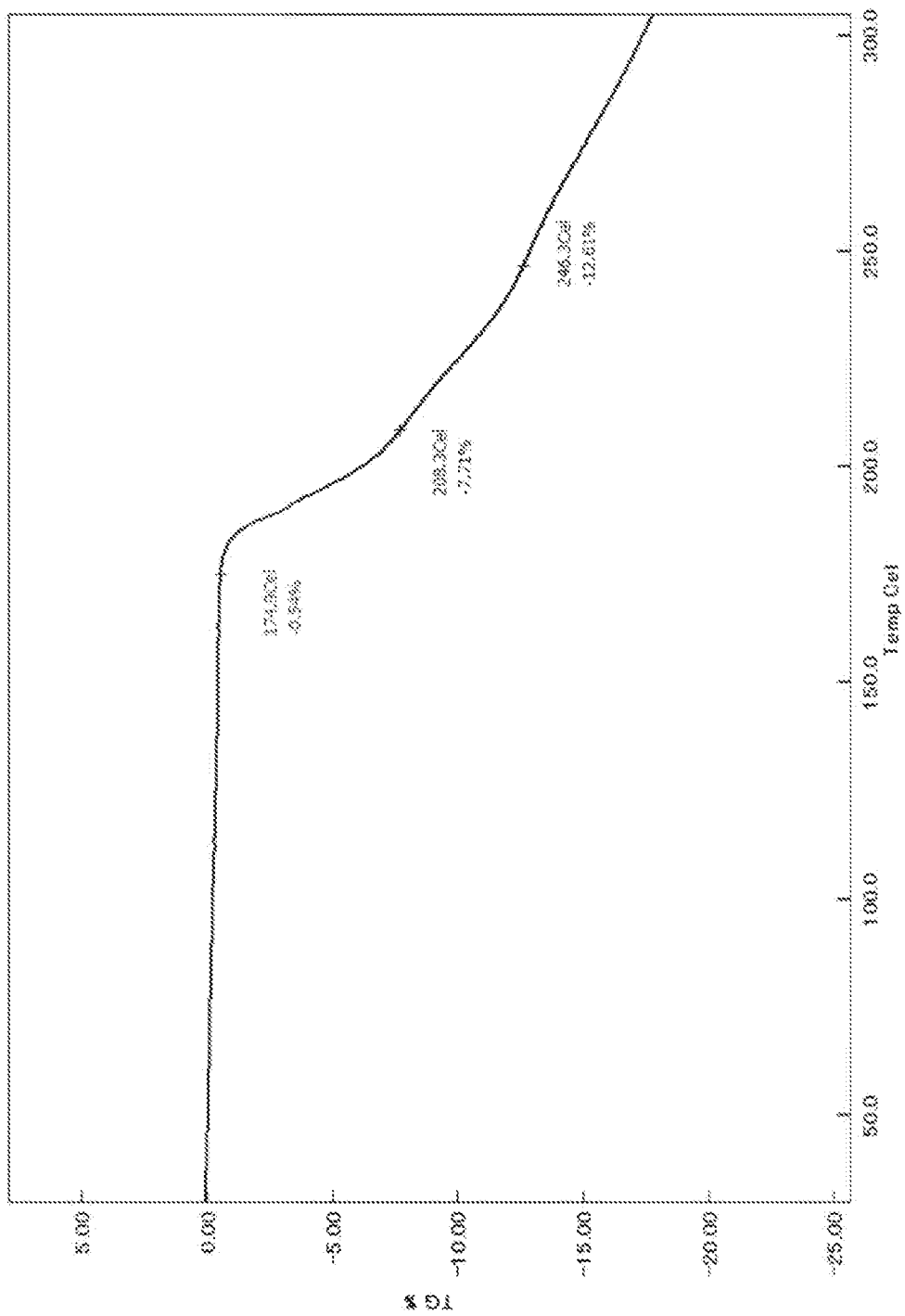
FIG. 2 depicts a thermogravimetry (TG) thermogram of Form II of Compound 1.

Form II of Compound 1 may also be characterized by thermogravimetry (TG). In some embodiments, Form II of Compound 1 is characterized by an onset of degradation between about 174° C. and about 176° C. In some embodiments, Form II of Compound 1 is characterized by an onset of degradation at about 175° C. In some embodiments, Form II of Compound 1 is characterized by a TG thermogram substantially the same as the pattern shown in FIG. 2.

Figure 3:
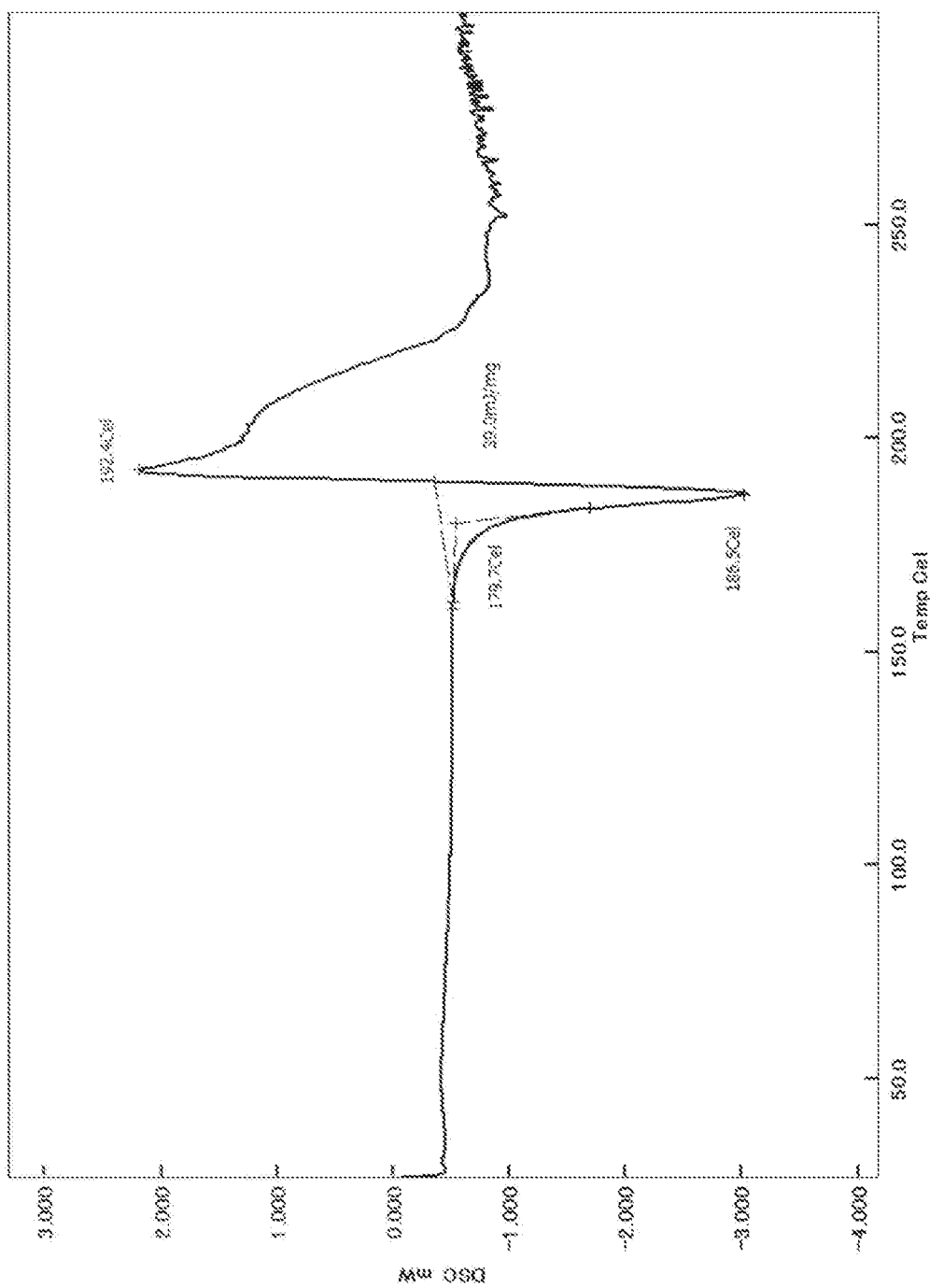
FIG. 3 depicts a differential scanning calorimetry (DSC) thermogram of Form II of Compound 1.

Form II of Compound 1 may also be characterized by differential scanning calorimetry (DSC). In some embodiments, Form II of Compound 1 is characterized by an onset of melting between about 179° C. and about 181° C. and/or by an exothermic peak between about 191° C. and about 194° C. In some embodiments, Form II of Compound 1 is characterized by an onset of melting at about 180° C. and/or by an exothermic peak at about 192° C. In some embodiments, Form II of Compound 1 is characterized by a DSC thermogram substantially the same as the pattern shown in FIG. 3.

In some embodiments, Form II of Compound 1 is characterized by having at least two of the following:
a) an XRPD pattern comprising at least three peaks selected from the group consisting of 9.7°, 10.7°, 19.0°, 19.3° and 20.9° 2θ±0.2° 2θ;
b) an onset of degradation at about 175° C. as measured by TG; and
c) an exothermic peak at about 192° C. as measured by DSC.

In some embodiments, the XRPD pattern comprises peaks at 9.7°, 10.7°, 19.0°, 19.3° and 20.9° 2θ±0.2° 2θ. In some embodiments, the XRPD pattern comprises peaks at 9.7°, 10.7°, and 19.0° 2θ±0.2° 2θ. In some embodiments, the XRPD pattern comprises peaks at 9.7°, 10.7°, and 19.3° 2θ±0.2° 2θ. In some embodiments, the XRPD pattern comprises peaks at 9.7°, 10.7°, and 20.9° 2θ±0.2° 2θ. In some embodiments, the XRPD pattern comprises peaks at 10.7°, 19.0°, and 19.3° 2θ±0.2° 2θ. In some embodiments, the XRPD pattern comprises peaks at 10.7°, 19.0°, and 20.9° 2θ±0.2° 2θ. In some embodiments, the XRPD pattern comprises peaks at 10.7°, 19.3°, and 20.9° 2θ±0.2° 2θ. In some embodiments, the XRPD pattern comprises peaks at 19.0°, 19.3° and 20.9° 2θ±0.2° 2θ. In some embodiments, the XRPD pattern comprises peaks at 9.7°, 19.0°, and 19.3° 2θ±0.2° 2θ. In some embodiments, the XRPD pattern comprises peaks at 9.7°, 19.0°, and 20.9° 2θ±0.2° 2θ. In some embodiments, the XRPD pattern comprises peaks at 9.7°, 19.3°, and 20.9° 2θ±0.2° 2θ. In some embodiments, the XRPD pattern comprises one or more peaks selected from the group consisting of 7.2°, 13.1°, and 15.7°±0.2° 2θ.

Form III of Compound 1

Figure 4:
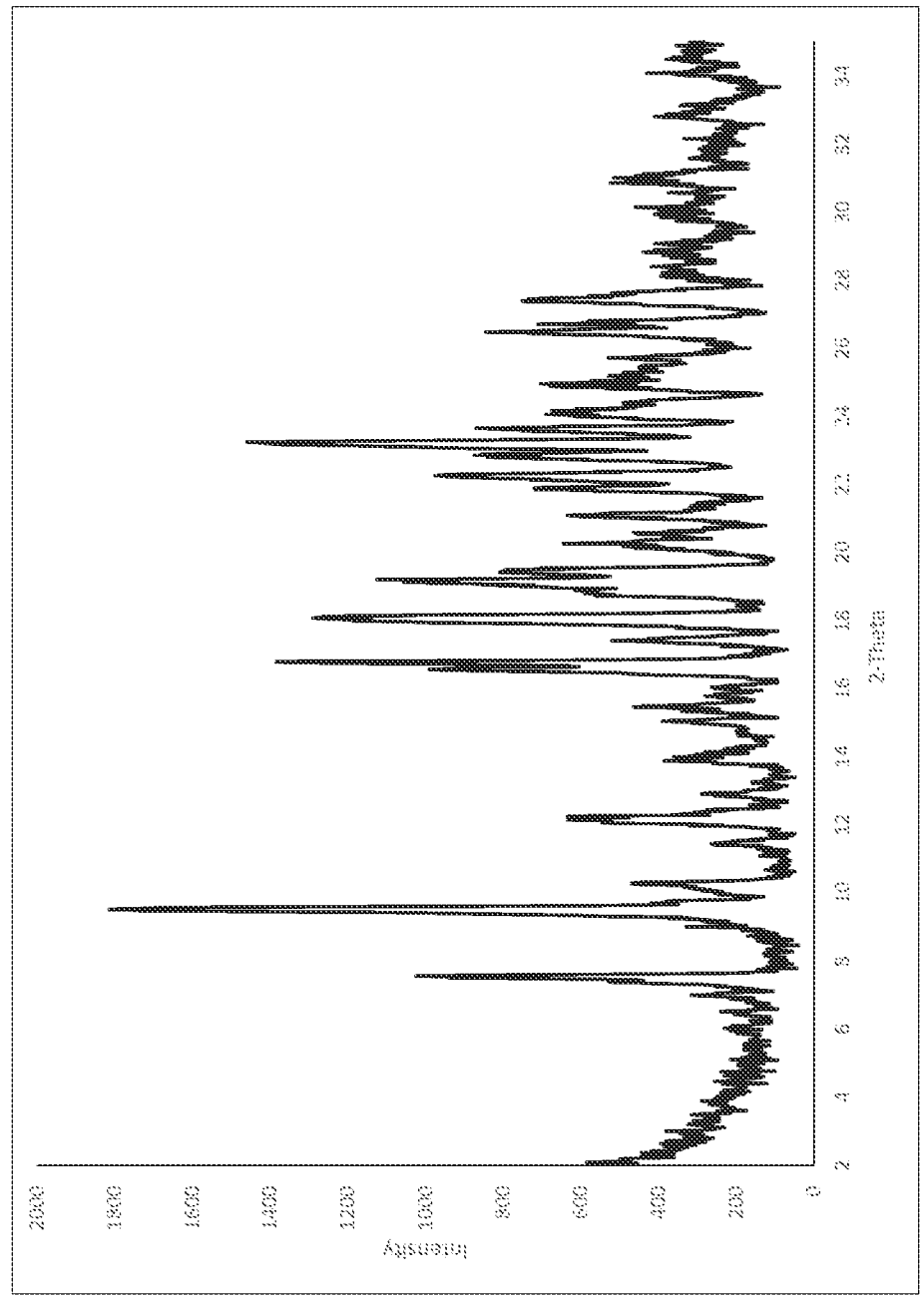
FIG. 4 depicts a powder X-ray diffraction pattern of Form III of Compound 1.

The present disclosure provides a crystalline form of Compound 1 characterized as Form III of Compound 1. In some embodiments, Form III of Compound 1 is a hemihydrate. In some embodiments, Form III of Compound 1 is characterized by an XRPD pattern comprising at least three peaks selected from the group consisting of 7.5°, 9.5°, 16.8°, and 18.1° 2θ±0.2° 2θ. In some embodiments, Form III of Compound 1 is characterized by an XRPD pattern comprising at least five peaks selected from the group consisting of 7.5°, 9.5°, 12.2°, 16.6°, 16.8°, and 18.1° 2θ±0.2° 2θ. In some embodiments, Form III of Compound 1 is characterized by an XRPD pattern having peaks at 7.5°, 9.5°, 16.8°, and 18.1° 2θ±0.2° 2θ. In certain such embodiments, the XRPD pattern has one or more peaks selected from the group consisting of 12.2° and 16.6°±0.2° 2θ. In some embodiments, Form III of Compound 1 is characterized by an XRPD pattern substantially the same as the pattern shown in FIG. 4.

Figure 5:
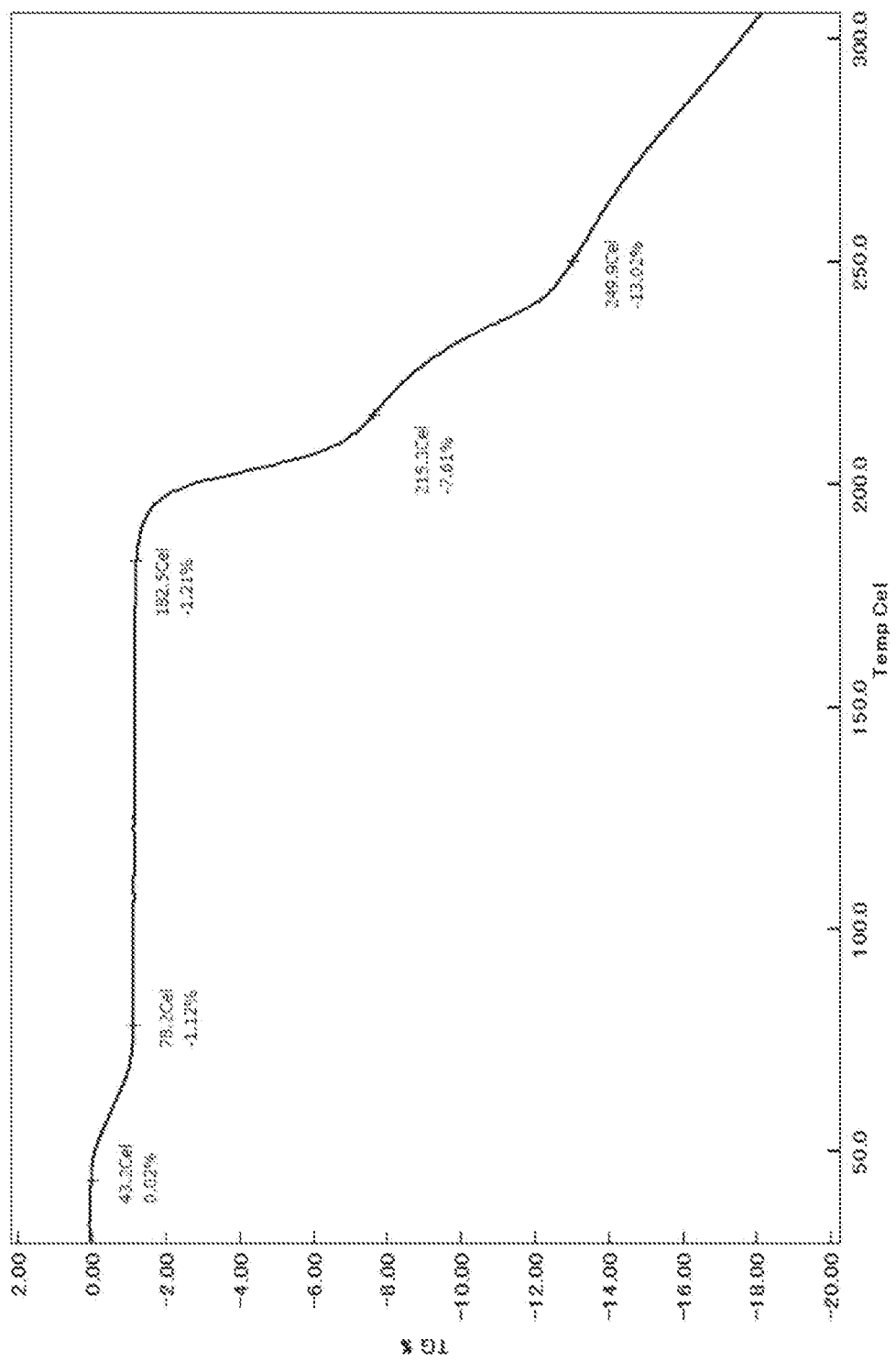
FIG. 5 depicts a TG thermogram of Form III of Compound 1.

Form III of Compound 1 may also be characterized by thermogravimetry (TG). In some embodiments, Form III of Compound 1 is characterized by an onset of dehydration at about 43° C. and continued dehydration to about 78° C. In some embodiments, Form III of Compound 1 is characterized by an onset of degradation at about 183° C. In some embodiments, Form III of Compound 1 is characterized by a TG thermogram substantially the same as the pattern shown in FIG. 5.

Figure 6:
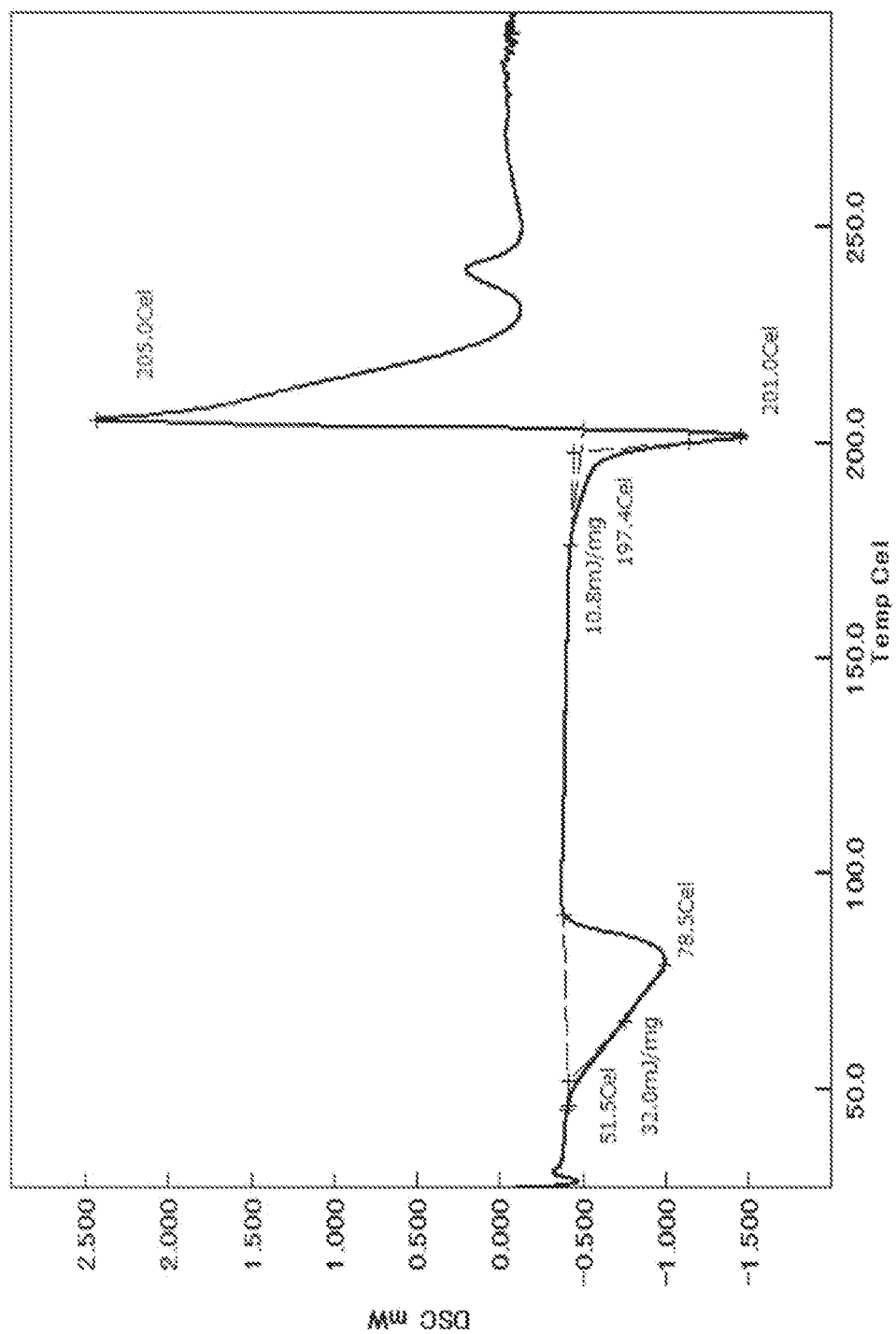
FIG. 6 depicts a DSC thermogram of Form III of Compound 1.

Form III of Compound 1 may also be characterized by differential scanning calorimetry (DSC). In some embodiments, Form III of Compound 1 is characterized by an endothermic peak at about 79° C. or by an exothermic peak at about 205° C. In some embodiments, Form II of Compound 1 is characterized by a DSC thermogram substantially the same as the pattern shown in FIG. 6.

In some embodiments, Form III of Compound 1 is characterized by having at least two of the following:
a) an XRPD pattern comprising at least three peaks selected from the group consisting of 7.5°, 9.5°, 16.8°, and 18.1° 2θ±0.2° 2θ;
b) an onset of dehydration at about 43° C. as measured by TG; and
c) an endothermic peak at about 79° C. as measured by DSC.

In some embodiments, the XRPD pattern comprises peaks at 7.5°, 9.5°, 16.8°, and 18.1° 2θ±0.2° 2θ. In some embodiments, the XRPD pattern comprises peaks at 7.5°, 9.5°, and 16.8° 2θ±0.2° 2θ. In some embodiments, the XRPD pattern comprises peaks at 7.5°, 9.5°, and 18.1° 2θ±0.2° 2θ. In some embodiments, the XRPD pattern comprises peaks at 9.5°, 16.8°, and 18.1° 2θ±0.2° 2θ. In some embodiments, the XRPD pattern comprises peaks at 7.5°, 16.8°, and 18.1°

2θ±0.2° 2θ. In some embodiments, the XRPD pattern comprises one or more peaks selected from the group consisting of 12.2° and 16.6°±0.2° 2θ.

Form IV of Compound 1

The present disclosure provides a crystalline form of Compound 1 characterized as Form IV of Compound 1. Form IV, thought to be an anhydrate crystalline form distinct from the other forms disclosed herein, was produced by heating Form III, beginning at about 52° C. Form IV converted back to Form III upon cooling to room temperature. Form IV was not able to be isolated for further characterization.

Form V of Compound 1

Figure 7:
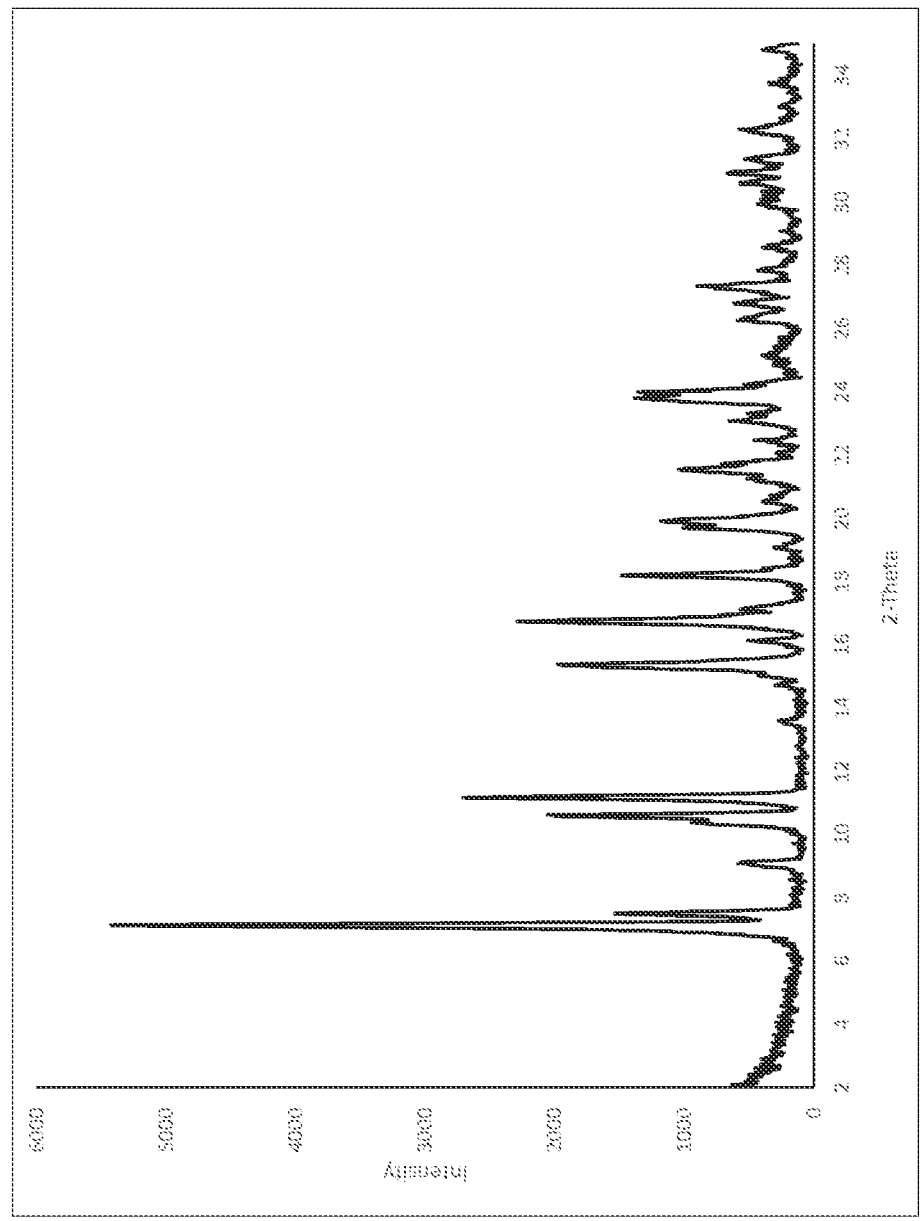
FIG. 7 depicts a powder X-ray diffraction pattern of Form V of Compound 1.

The present disclosure provides a crystalline form of Compound 1 characterized as Form V of Compound 1. In some embodiments, Form V of Compound 1 is a toluene solvate. In some embodiments, Form V of Compound 1 is characterized by an XRPD pattern comprising at least three peaks selected from the group consisting of 7.1°, 10.6°, 11.2°, 15.3° and 16.7° 2θ±0.2° 2θ. In some embodiments, Form V of Compound 1 is characterized by an XRPD pattern substantially the same as the pattern shown in FIG. 7.

Form V of Compound 1 may also be characterized by TG or DSC. In some embodiments, Form V of Compound 1 is characterized by a TG thermogram substantially the same as the pattern shown in FIG. 8 and/or by a DSC thermogram substantially the same as the pattern shown in FIG. 9.

Figure 8:
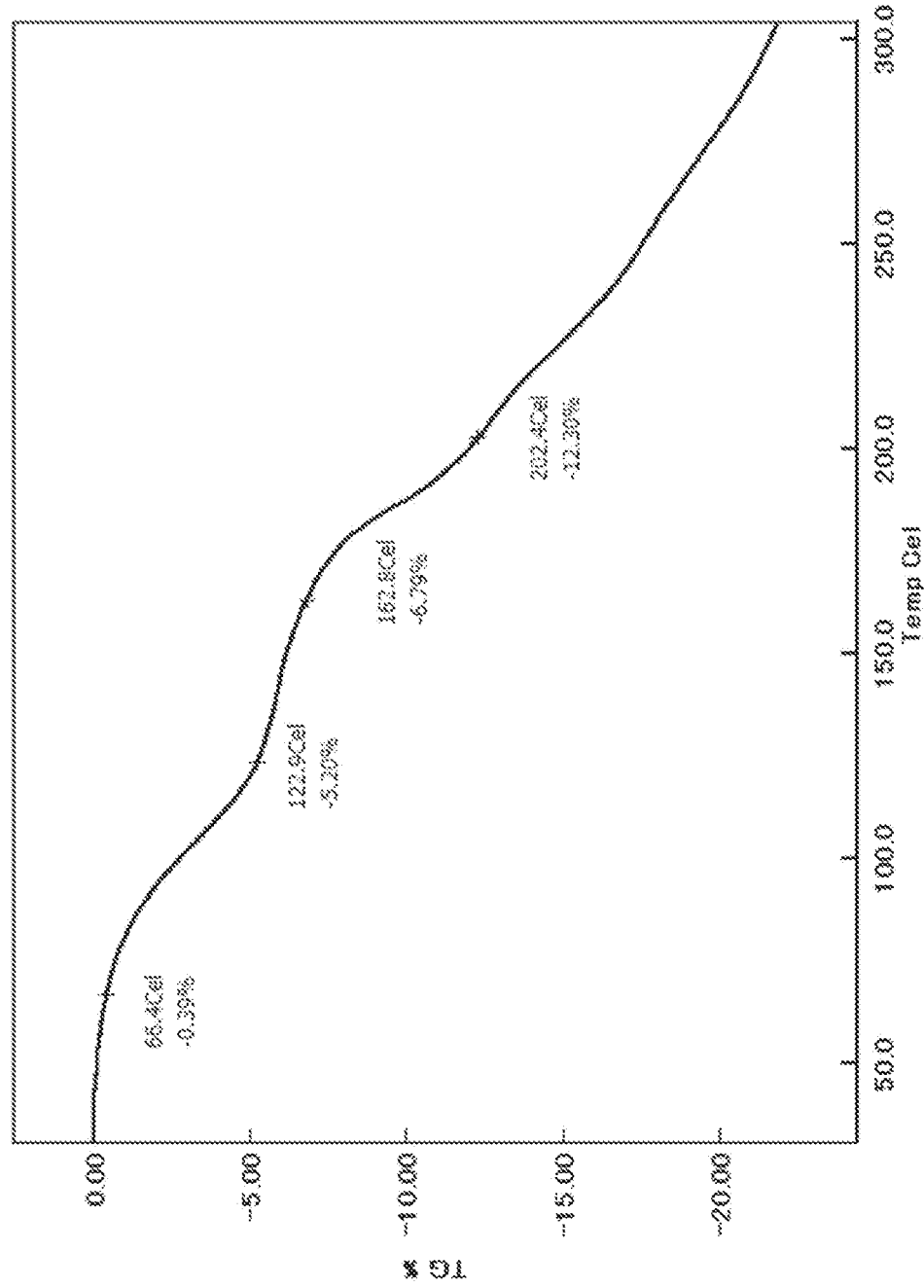
FIG. 8 depicts a TG thermogram of Form V of Compound 1.
Figure 9:
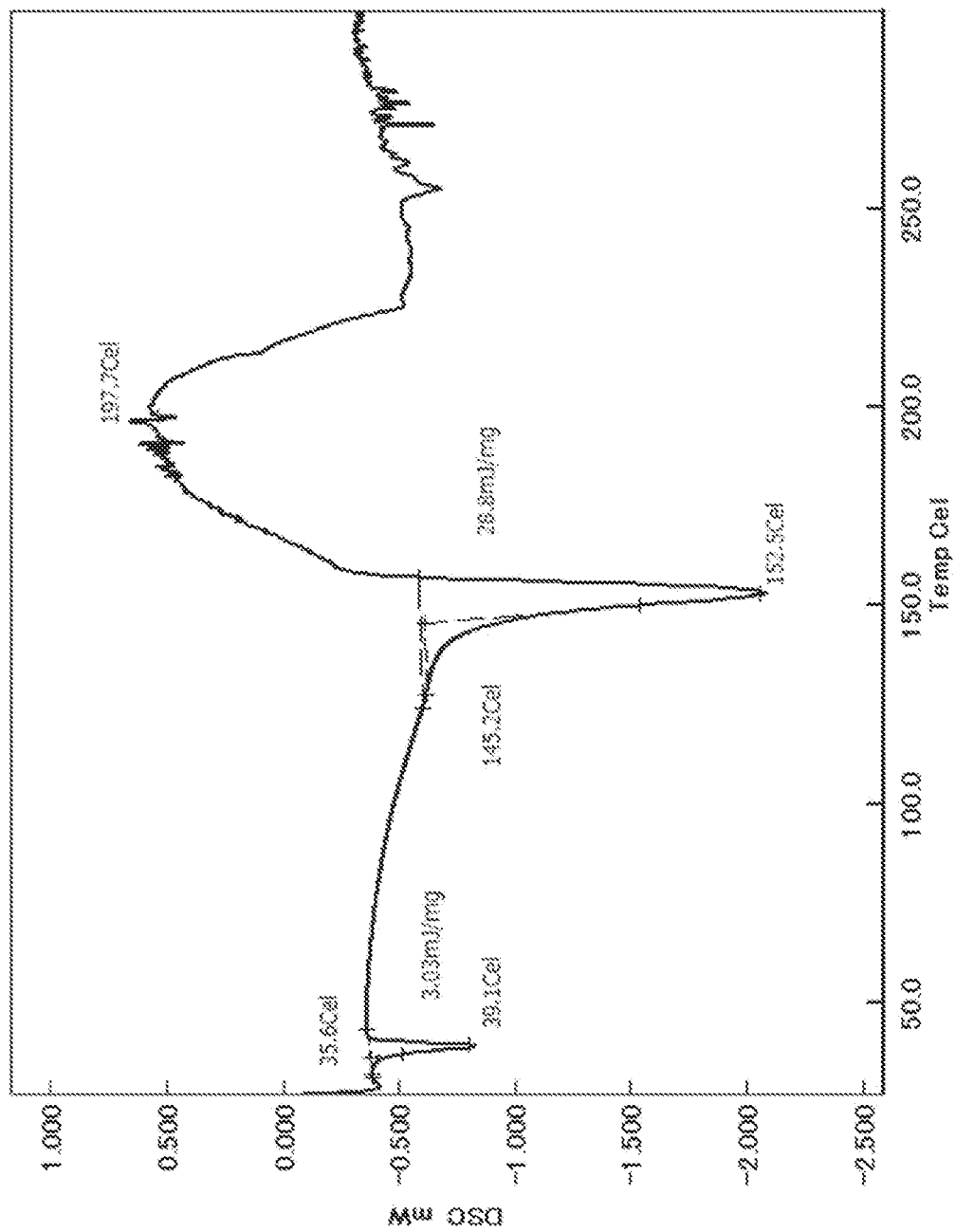
FIG. 9 depicts a DSC thermogram of Form V of Compound 1.

In some embodiments, Form V of Compound 1 is characterized by having at least two of the following:
a) an XRPD pattern comprising at least three peaks selected from the group consisting of 7.1°, 10.6°, 11.2°, 15.3° and 16.7° 2θ±0.2° 2θ;
b) a TG thermogram substantially the same as the pattern shown in FIG. 8; and
c) a DSC thermogram substantially the same as the pattern shown in FIG. 9.

In some embodiments, the XRPD pattern comprises peaks at 7.1°, 10.6°, 11.2°, 15.3° and 16.7° 2θ±0.2° 2θ. In some embodiments, the XRPD pattern comprises peaks at 7.1°, 10.6°, and 11.2° 2θ±0.2° 2θ. In some embodiments, the XRPD pattern comprises peaks at 7.1°, 10.6°, and 15.3° 2θ±0.2° 2θ. In some embodiments, the XRPD pattern comprises peaks at 7.1°, 10.6°, and 16.7° 2θ±0.2° 2θ. In some embodiments, the XRPD pattern comprises peaks at 7.1°, 11.2°, and 15.3° 2θ±0.2° 2θ. In some embodiments, the XRPD pattern comprises peaks at 7.1°, 11.2°, and 16.7° 2θ±0.2° 2θ. In some embodiments, the XRPD pattern comprises peaks at 7.1°, 15.3° and 16.7° 2θ±0.2° 2θ. In some embodiments, the XRPD pattern comprises peaks at 11.2°, 15.3° and 16.7° 2θ±0.2° 2θ. In some embodiments, the XRPD pattern comprises peaks at 10.6°, 15.3° and 16.7° 2θ±0.2° 2θ. In some embodiments, the XRPD pattern comprises peaks at 10.6°, 11.2°, and 16.7° 2θ±0.2° 2θ. In some embodiments, the XRPD pattern comprises peaks at 10.6°, 11.2°, and 15.3° 2θ±0.2° 2θ.

Form VI of Compound 1

Figure 10:
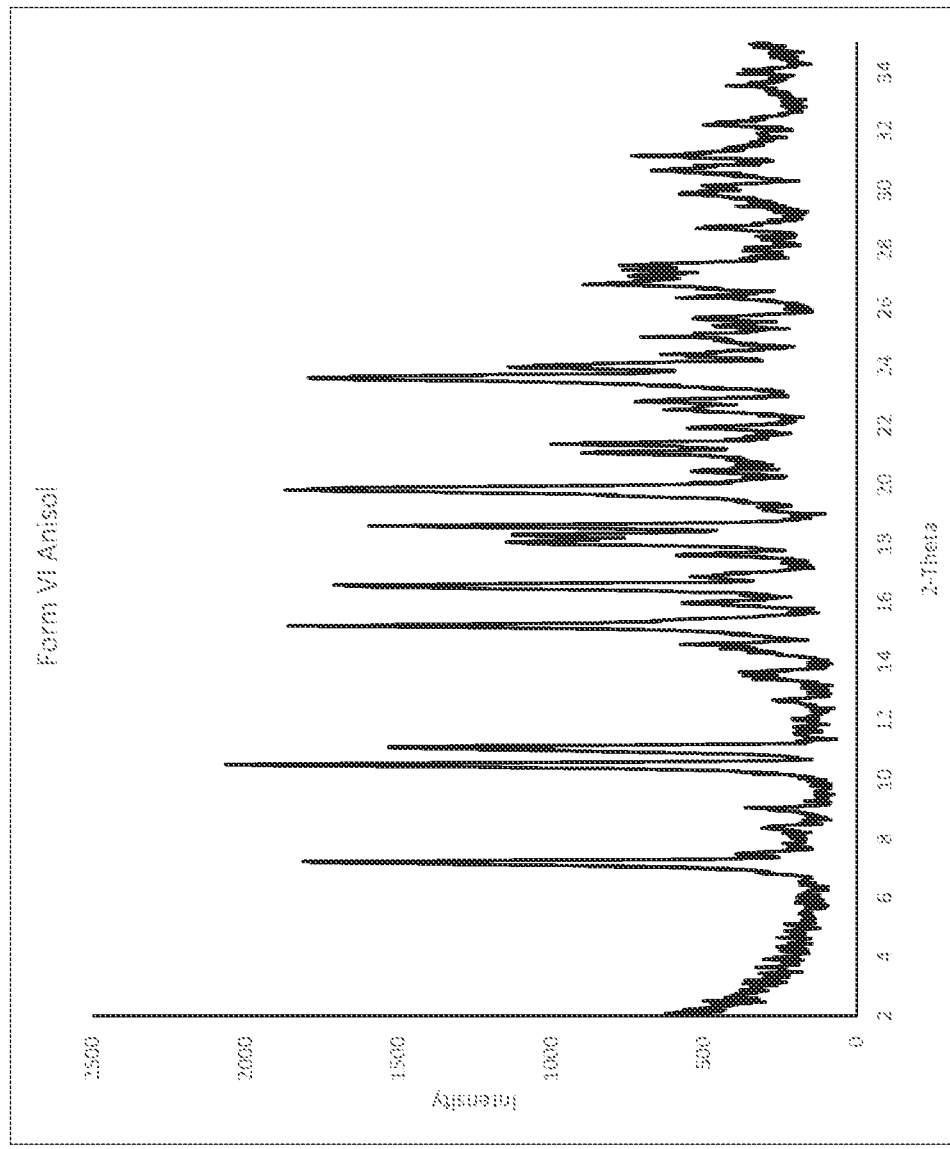
FIG. 10 depicts a powder X-ray diffraction pattern of Form VI of Compound 1.

The present disclosure provides a crystalline form of Compound 1 characterized as Form VI of Compound 1. In some embodiments, Form VI of Compound 1 is an anisole solvate. In some embodiments, Form VI of Compound 1 is characterized by an XRPD pattern comprising at least three peaks selected from the group consisting of 7.2°, 10.5°, 11.1°, 15.2° and 16.6° 2θ±0.2° 2θ. In some embodiments, Form VI of Compound 1 is characterized by an XRPD pattern substantially the same as the pattern shown in FIG. 10.

Form VI of Compound 1 may also be characterized by TG or DSC. In some embodiments, Form VI of Compound 1 is characterized by a TG thermogram substantially the same as the pattern shown in FIG. 11 and/or by a DSC thermogram substantially the same as the pattern shown in FIG. 12.

Figure 11:
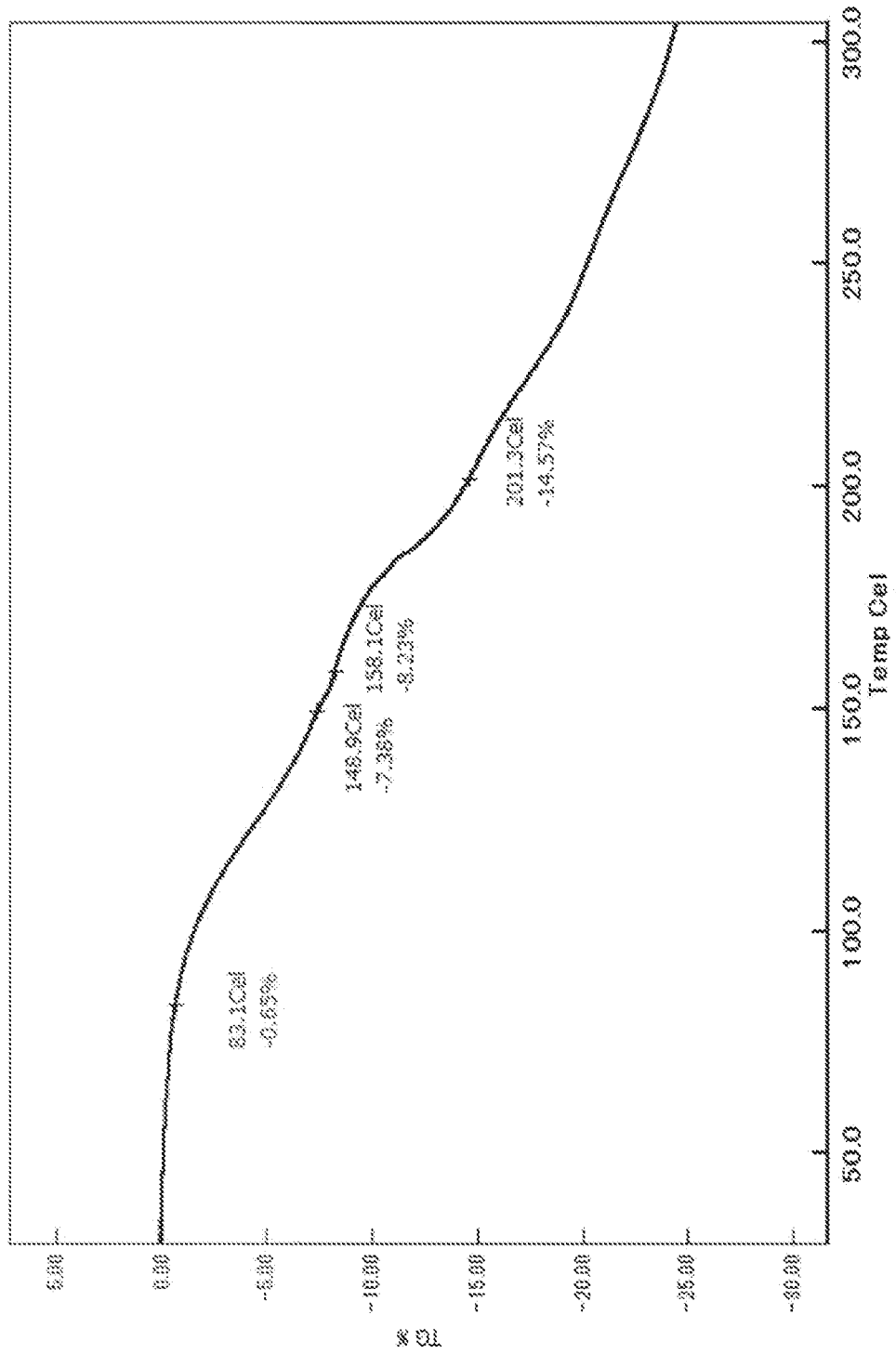
FIG. 11 depicts a TG thermogram of Form VI of Compound 1.
Figure 12:
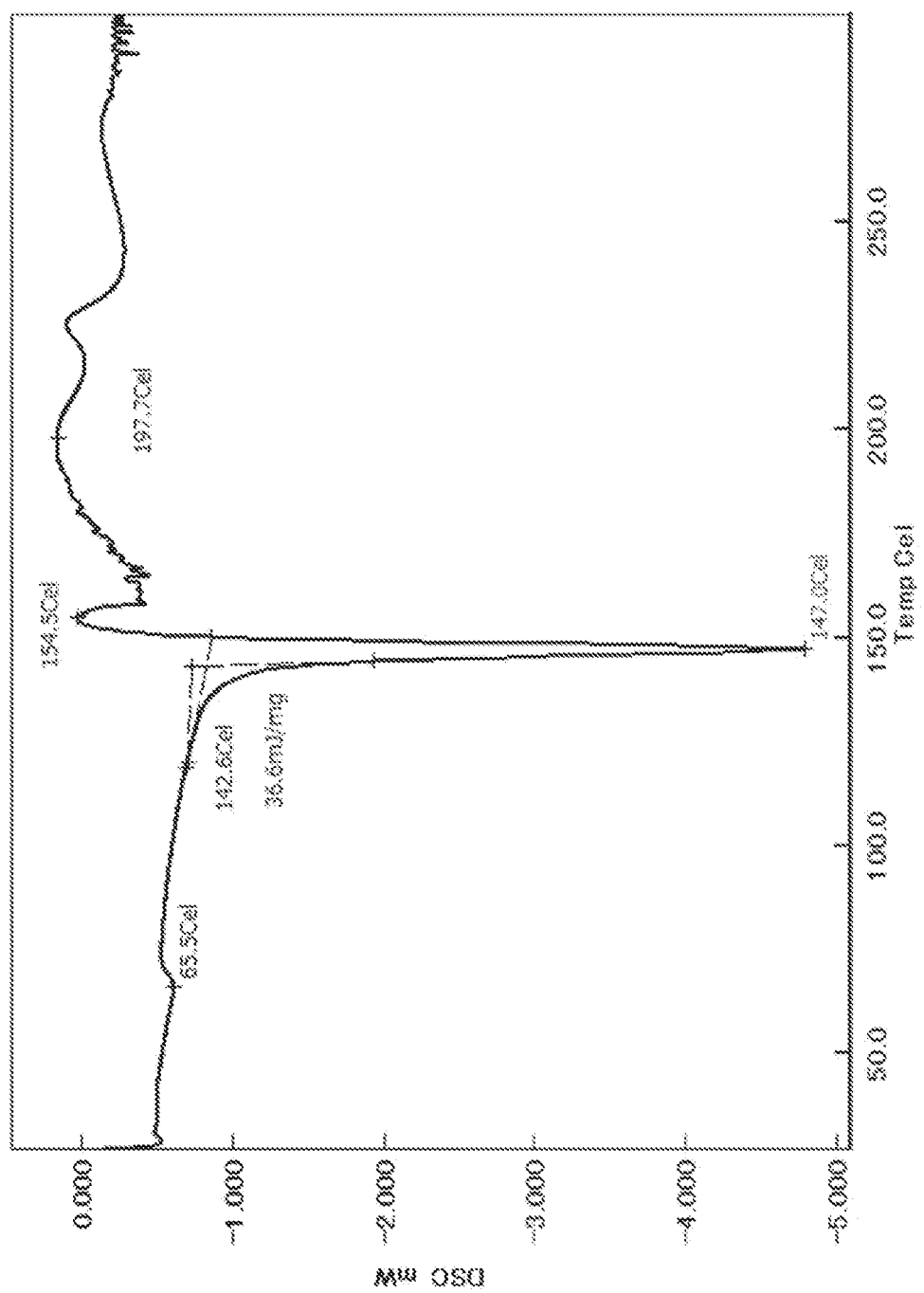
FIG. 12 depicts a DSC thermogram of Form VI of Compound 1.

In some embodiments, Form VI of Compound 1 is characterized by having at least two of the following:
a) an XRPD pattern comprising at least three peaks selected from the group consisting of 7.2°, 10.5°, 11.1°, 15.2° and 16.6° 2θ±0.2° 2θ;
b) a TG thermogram substantially the same as the pattern shown in FIG. 11; and
c) a DSC thermogram substantially the same as the pattern shown in FIG. 12.

In some embodiments, the XRPD pattern comprises peaks at 7.2°, 10.5°, 11.1°, 15.2° and 16.6° 2θ±0.2° 2θ. In some embodiments, the XRPD pattern comprises peaks at 7.2°, 10.5°, and 11.1° 2θ±0.2° 2θ. In some embodiments, the XRPD pattern comprises peaks at 7.2°, 10.5°, and 15.2° 2θ±0.2° 2θ. In some embodiments, the XRPD pattern comprises peaks at 7.2°, 10.5°, and 16.6° 2θ±0.2° 2θ. In some embodiments, the XRPD pattern comprises peaks at 7.2°, 11.1°, and 15.2° 2θ±0.2° 2θ. In some embodiments, the XRPD pattern comprises peaks at 7.2°, 11.1°, and 16.6° 2θ±0.2° 2θ. In some embodiments, the XRPD pattern comprises peaks at 7.2°, 15.2° and 16.6° 2θ±0.2° 2θ. In some embodiments, the XRPD pattern comprises peaks at 11.1°, 15.2° and 16.6° 2θ±0.2° 2θ. In some embodiments, the XRPD pattern comprises peaks at 10.5°, 11.1°, and 15.2° 2θ±0.2° 2θ. In some embodiments, the XRPD pattern comprises peaks at 10.5°, 11.1°, and 16.6° 2θ±0.2° 2θ. In some embodiments, the XRPD pattern comprises peaks at 10.5°, 15.2° and 16.6° 2θ±0.2° 2θ.

Form VII of Compound 1

Figure 13:
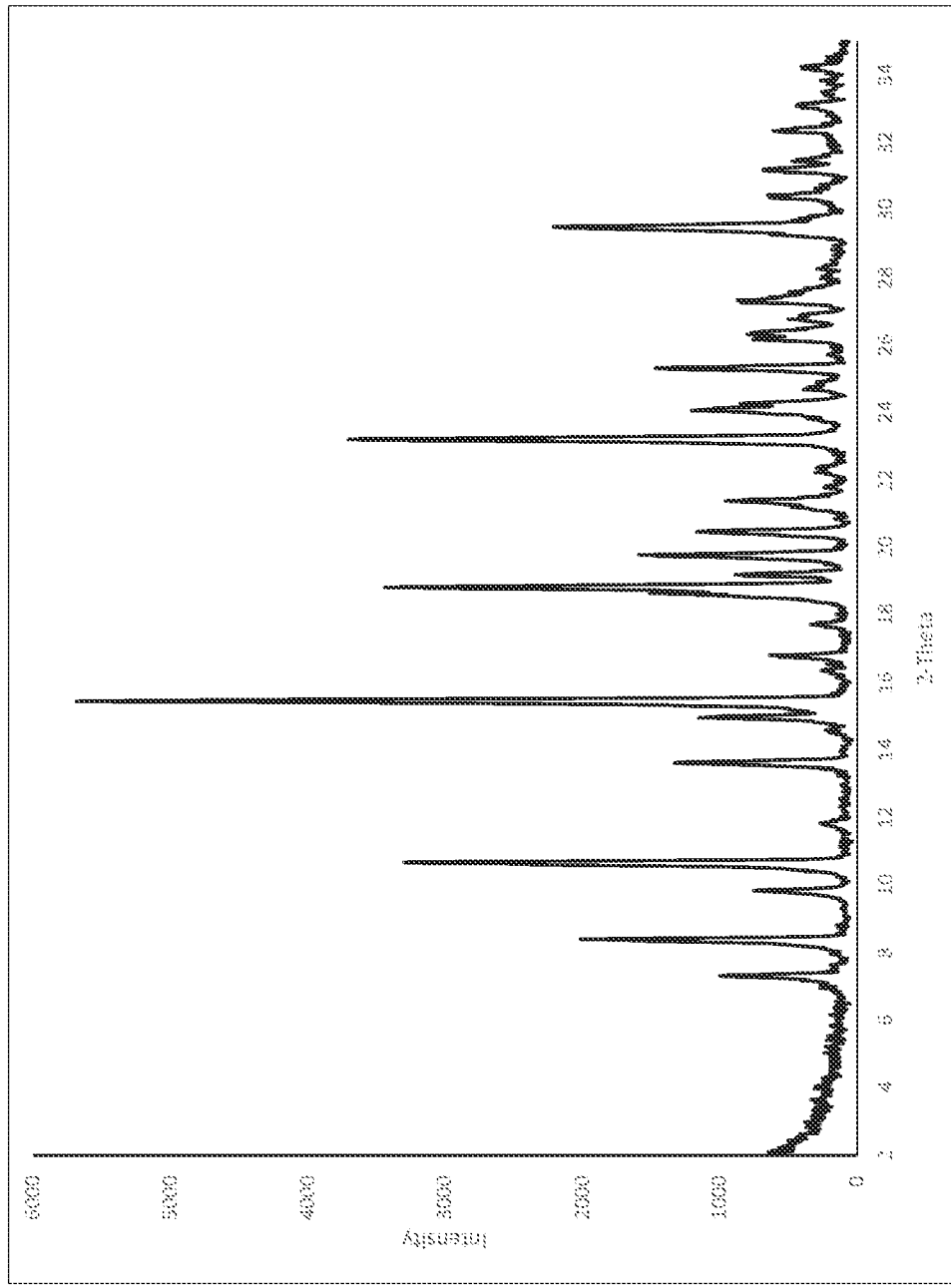
FIG. 13 depicts a powder X-ray diffraction pattern of Form VII of Compound 1.

The present disclosure provides a crystalline form of Compound 1 characterized as Form VII of Compound 1. In some embodiments, Form VII of Compound 1 is an isopropyl alcohol solvate. In some embodiments, Form VII of Compound 1 is characterized by an XRPD pattern comprising at least three peaks selected from the group consisting of 8.4°, 10.6°, 13.6°, 15.4° and 18.8° 2θ±0.2° 2θ. In some embodiments, Form VII of Compound 1 is characterized by an XRPD pattern substantially the same as the pattern shown in FIG. 13.

Form VII of Compound 1 may also be characterized by TG or DSC. In some embodiments, Form VII of Compound 1 is characterized by a TG thermogram substantially the same as the pattern shown in FIG. 14 and/or by a DSC thermogram substantially the same as the pattern shown in FIG. 15.

Figure 14:
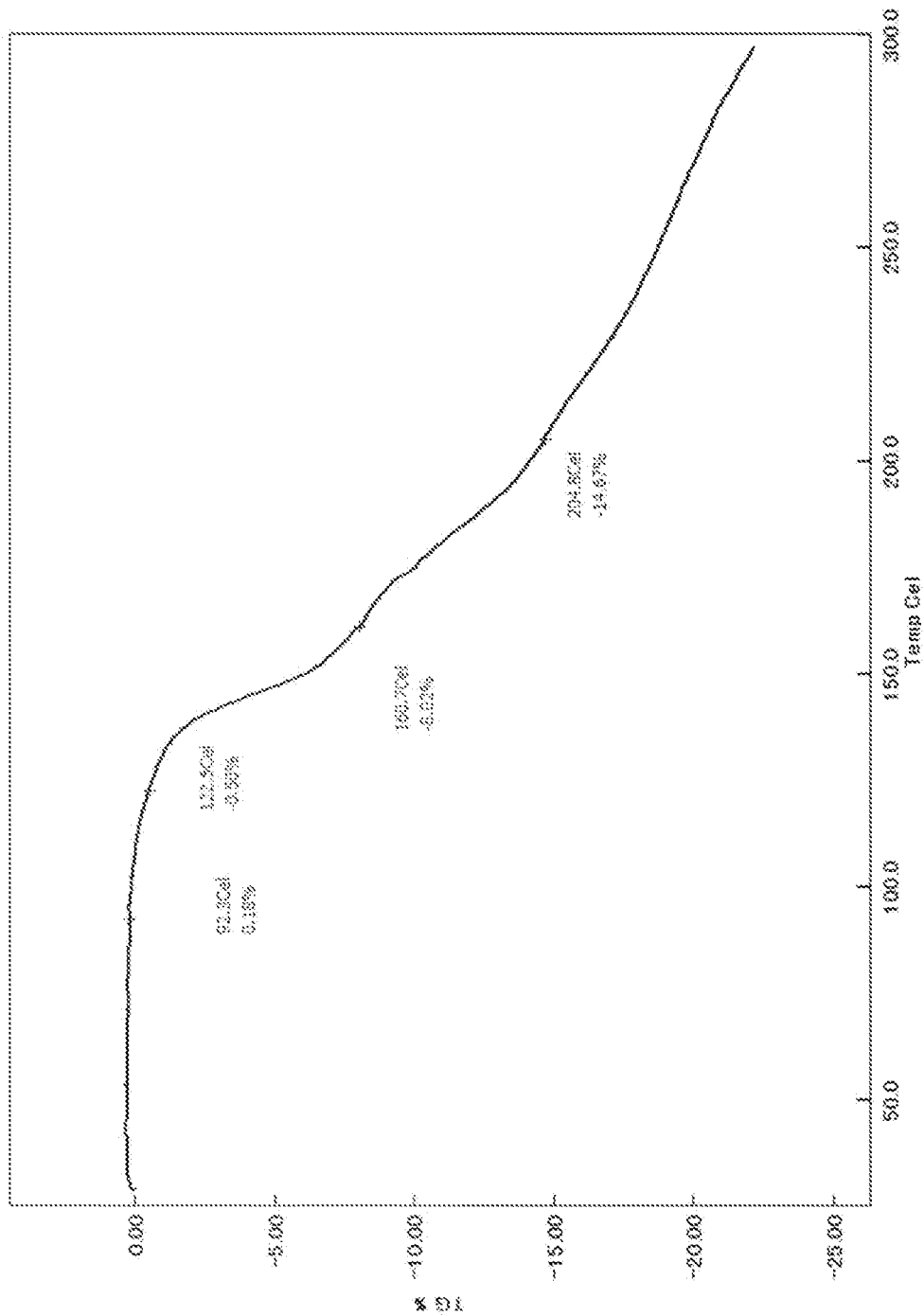
FIG. 14 depicts a TG thermogram of Form VII of Compound 1.
Figure 15:
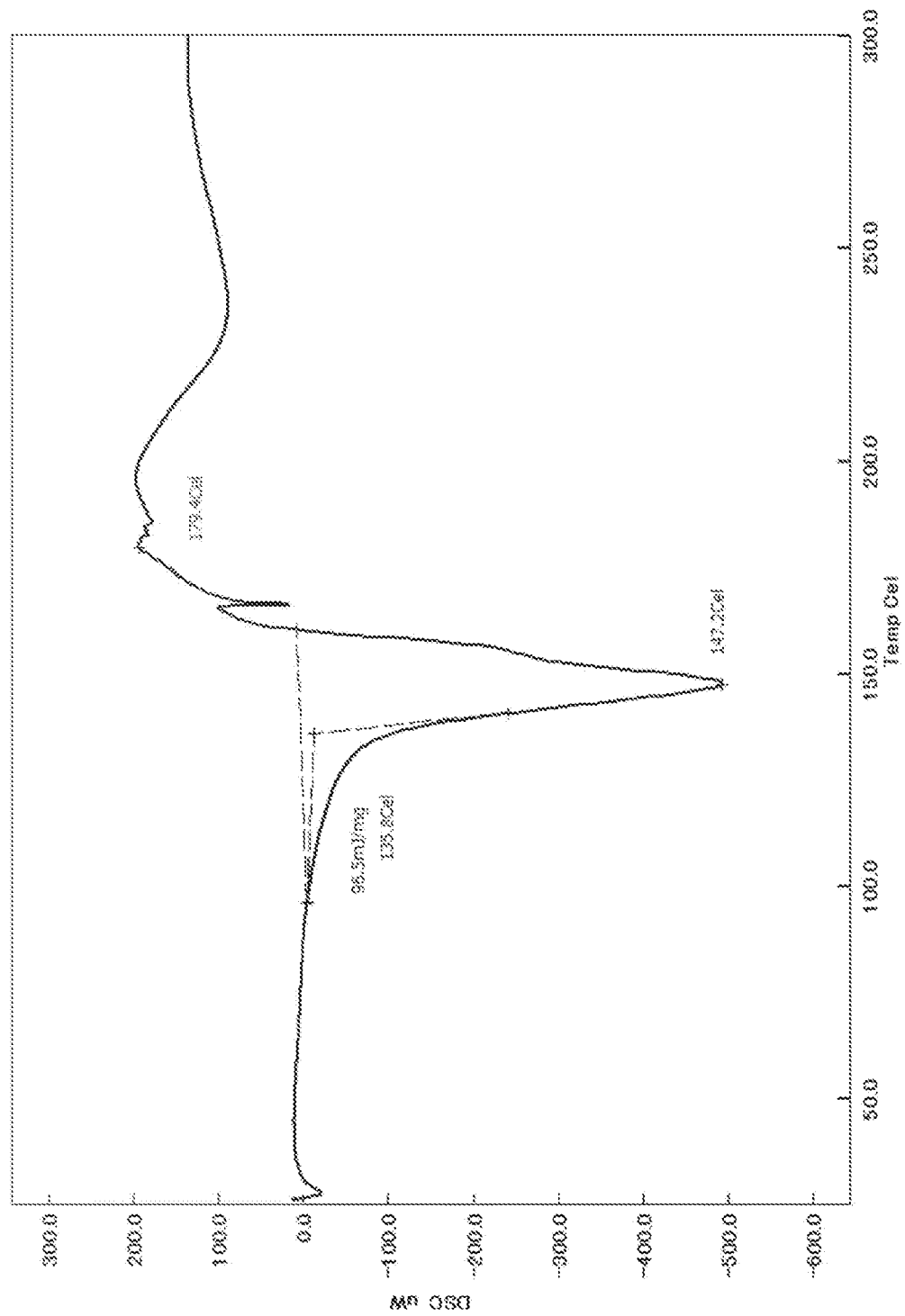
FIG. 15 depicts a DSC thermogram of Form VII of Compound 1.

In some embodiments, Form VII of Compound 1 is characterized by having at least two of the following:
a) an XRPD pattern comprising at least three peaks selected from the group consisting of 8.4°, 10.6°, 13.6°, 15.4° and 18.8° 2θ±0.2° 2θ;
b) a TG thermogram substantially the same as the pattern shown in FIG. 14; and
c) a DSC thermogram substantially the same as the pattern shown in FIG. 15.

In some embodiments, the XRPD pattern comprises peaks at 8.4°, 10.6°, 13.6°, 15.4° and 18.8° 2θ±0.2° 2θ. In some embodiments, the XRPD pattern comprises peaks at 8.4°, 10.6°, and 13.6° 2θ±0.2° 2θ. In some embodiments, the XRPD pattern comprises peaks at 8.4°, 10.6°, and 15.4° 2θ±0.2° 2θ. In some embodiments, the XRPD pattern comprises peaks at 8.4°, 10.6°, and 18.8° 2θ±0.2° 2θ. In some embodiments, the XRPD pattern comprises peaks at 8.4°, 13.6°, and 15.4° 2θ±0.2° 2θ. In some embodiments, the XRPD pattern comprises peaks at 8.4°, 13.6°, and 18.8° 2θ±0.2° 2θ. In some embodiments, the XRPD pattern comprises peaks at 8.4°, 15.4° and 18.8° 2θ±0.2° 2θ. In some embodiments, the XRPD pattern comprises peaks at 10.6°, 13.6°, and 15.4° 2θ±0.2° 2θ. In some embodiments, the XRPD pattern comprises peaks at 10.6°, 13.6°, and 18.8° 2θ±0.2° 2θ. In some embodiments, the XRPD pattern comprises peaks at 10.6°, 15.4° and 18.8° 2θ±0.2° 2θ. In some embodiments, the XRPD pattern comprises peaks at 13.6°, 15.4° and 18.8° 2θ±0.2° 2θ.

Form VIII of Compound 1

Figure 16:
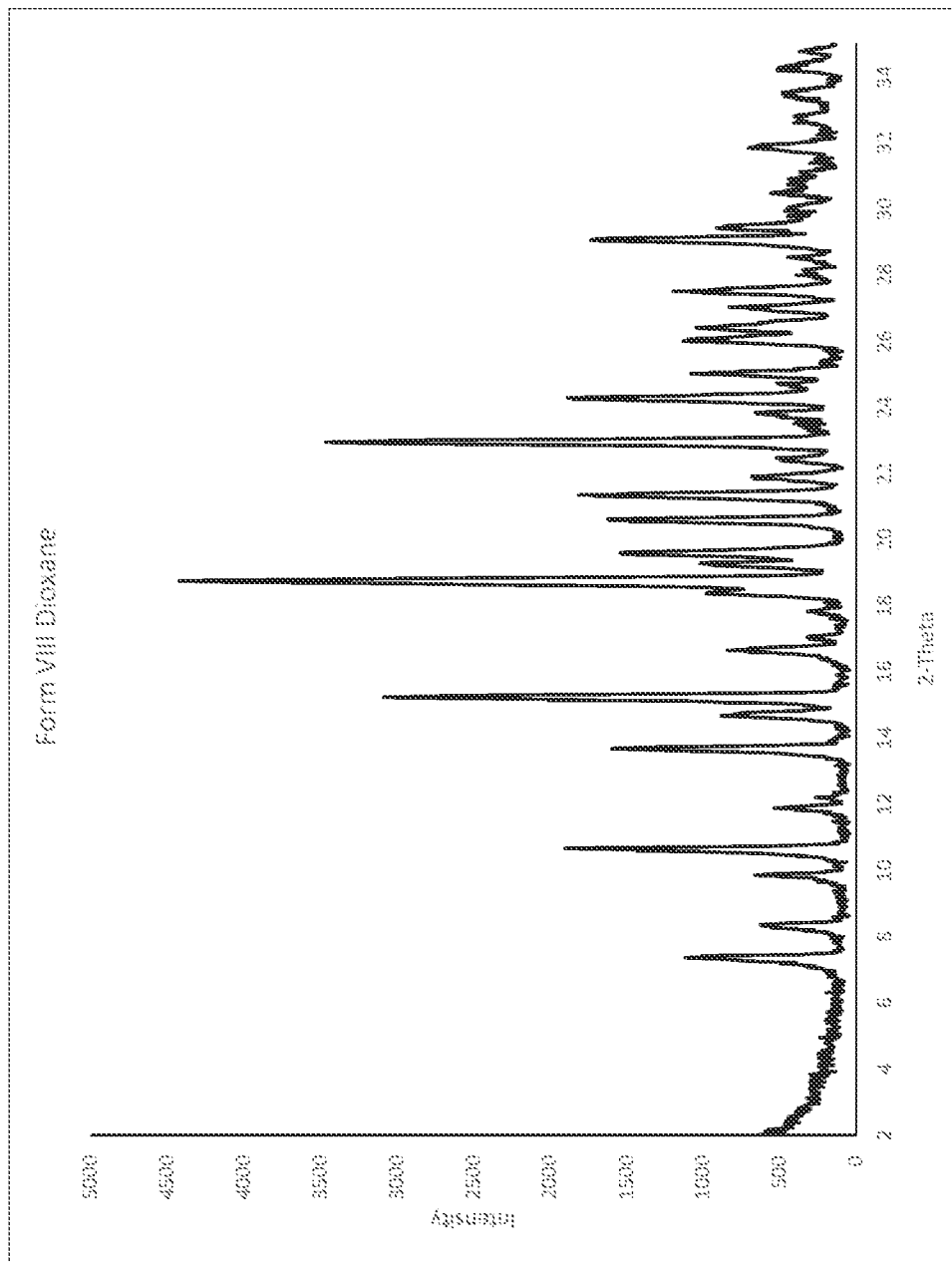
FIG. 16 depicts a powder X-ray diffraction pattern of Form VIII of Compound 1.

The present disclosure provides a crystalline form of Compound 1 characterized as Form VIII of Compound 1. In some embodiments, Form VIII of Compound 1 is a dioxane solvate. In some embodiments, Form VIII of Compound 1 is characterized by an XRPD pattern comprising at least three peaks selected from the group consisting of 7.4°, 10.6°, 13.7°, 15.2°, and 18.7° 2θ±0.2° 2θ. In some embodiments, Form VIII of Compound 1 is characterized by an XRPD pattern substantially the same as the pattern shown in FIG. 16.

Form VIII of Compound 1 may also be characterized by TG or DSC. In some embodiments, Form VIII of Compound 1 is characterized by a TG thermogram substantially the same as the pattern shown in FIG. 17 and/or by a DSC thermogram substantially the same as the pattern shown in FIG. 18.

Figure 17:
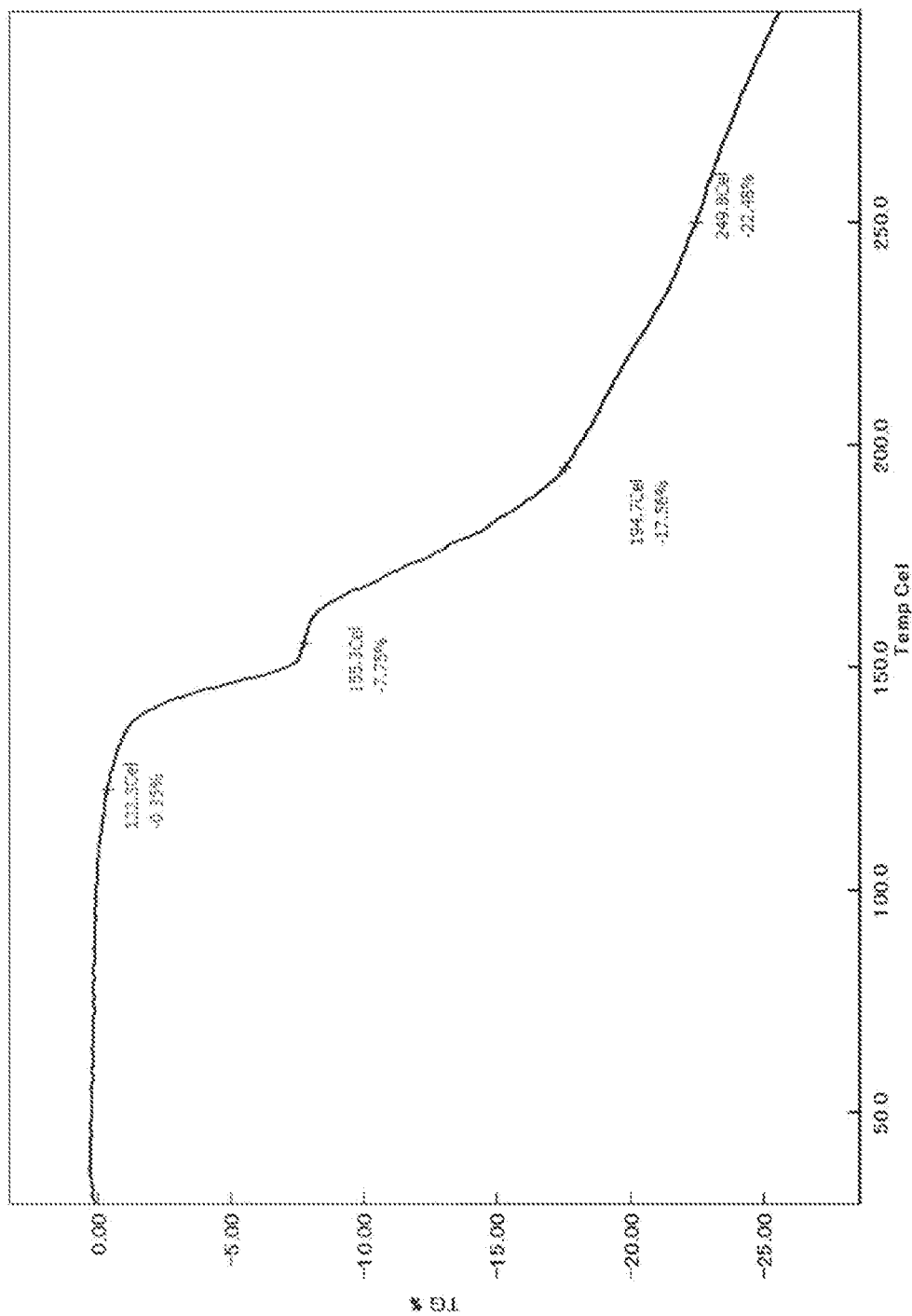
FIG. 17 depicts a TG thermogram of Form VIII of Compound 1.
Figure 18:
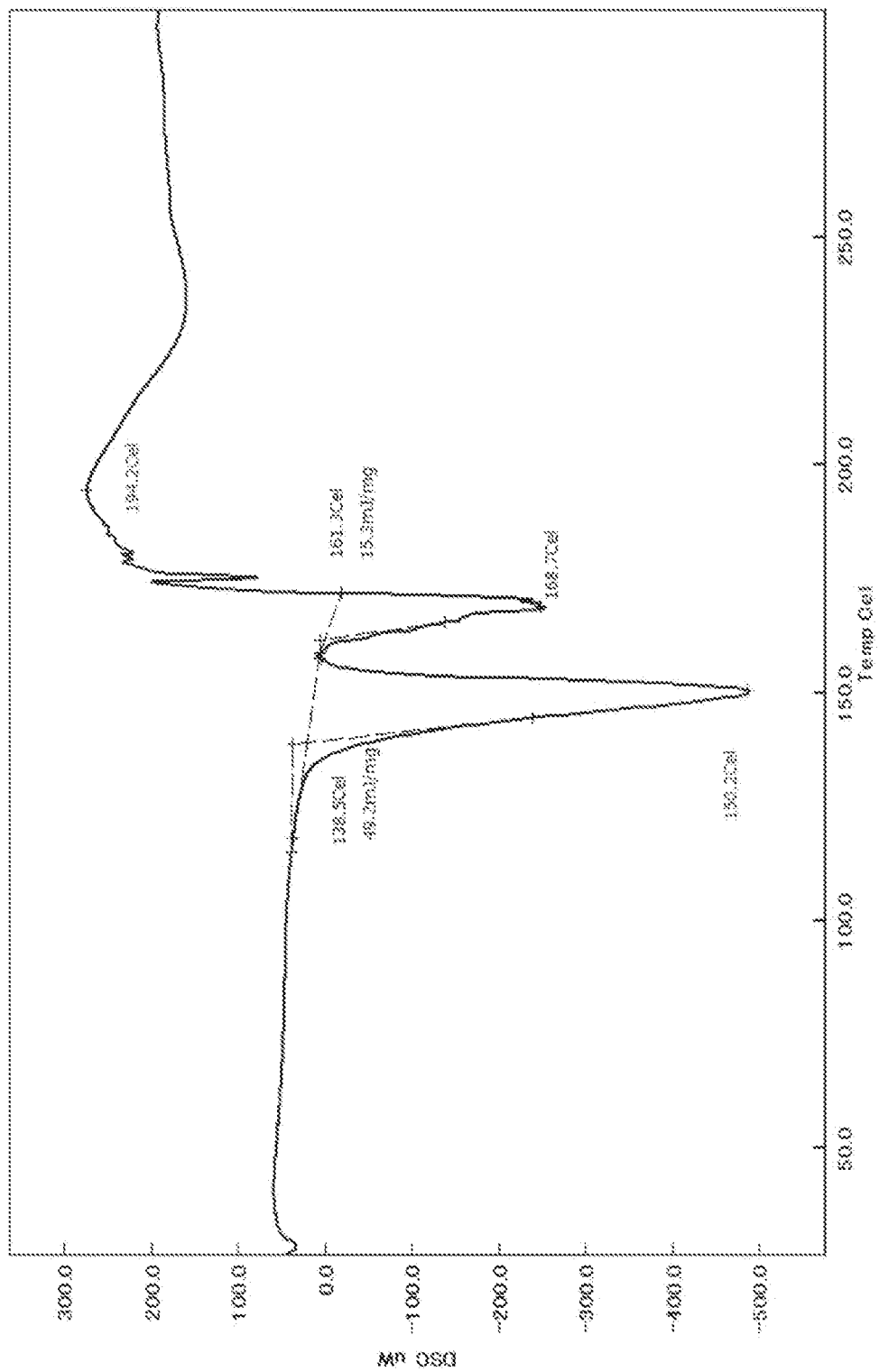
FIG. 18 depicts a DSC thermogram of Form VIII of Compound 1.

In some embodiments, Form VIII of Compound 1 is characterized by having at least two of the following:
a) an XRPD pattern comprising at least three peaks selected from the group consisting of 7.4°, 10.6°, 13.7°, 15.2°, and 18.7° 2θ±0.2° 2θ;
b) a TG thermogram substantially the same as the pattern shown in FIG. 17; and
c) a DSC thermogram substantially the same as the pattern shown in FIG. 18.

In some embodiments, the XRPD pattern comprises peaks at 7.4°, 10.6°, 13.7°, 15.2°, and 18.7° 2θ±0.2° 2θ. In some embodiments, the XRPD pattern comprises peaks at 7.4°, 10.6°, and 13.7° 2θ±0.2° 2θ. In some embodiments, the XRPD pattern comprises peaks at 7.4°, 10.6°, and 15.2° 2θ±0.2° 2θ. In some embodiments, the XRPD pattern comprises peaks at 7.4°, 10.6°, and 18.7° 2θ±0.2° 2θ. In some embodiments, the XRPD pattern comprises peaks at 7.4°, 13.7°, and 15.2° 2θ±0.2° 2θ. In some embodiments, the XRPD pattern comprises peaks at 7.4°, 13.7°, and 18.7° 2θ±0.2° 2θ. In some embodiments, the XRPD pattern comprises peaks at 7.4°, 15.2°, and 18.7° 2θ±0.2° 2θ. In some embodiments, the XRPD pattern comprises peaks at 10.6°, 13.7°, and 15.2° 2θ±0.2° 2θ. In some embodiments, the XRPD pattern comprises peaks at 10.6°, 13.7°, and 18.7° 2θ±0.2° 2θ. In some embodiments, the XRPD pattern comprises peaks at 10.6°, 15.2°, and 18.7° 2θ±0.2° 2θ. In some embodiments, the XRPD pattern comprises peaks at 13.7°, 15.2°, and 18.7° 2θ±0.2° 2θ.

Form IX of Compound 1

The present disclosure provides a crystalline form of Compound 1 characterized as Form IX of Compound 1. In some embodiments, Form IX of Compound 1 is an α,α,α-trifluorotoluene solvate. In some embodiments, Form IX of Compound 1 is characterized by an XRPD pattern substantially the same as the pattern shown in FIG. 19.

Form IX of Compound 1 may also be characterized by TG or DSC. In some embodiments, Form IX of Compound 1 is characterized by a TG thermogram substantially the same as the pattern shown in FIG. 20. In some embodiments, Form IX of Compound 1 is characterized by a DSC thermogram substantially the same as the pattern shown in FIG. 21.

Figure 19:
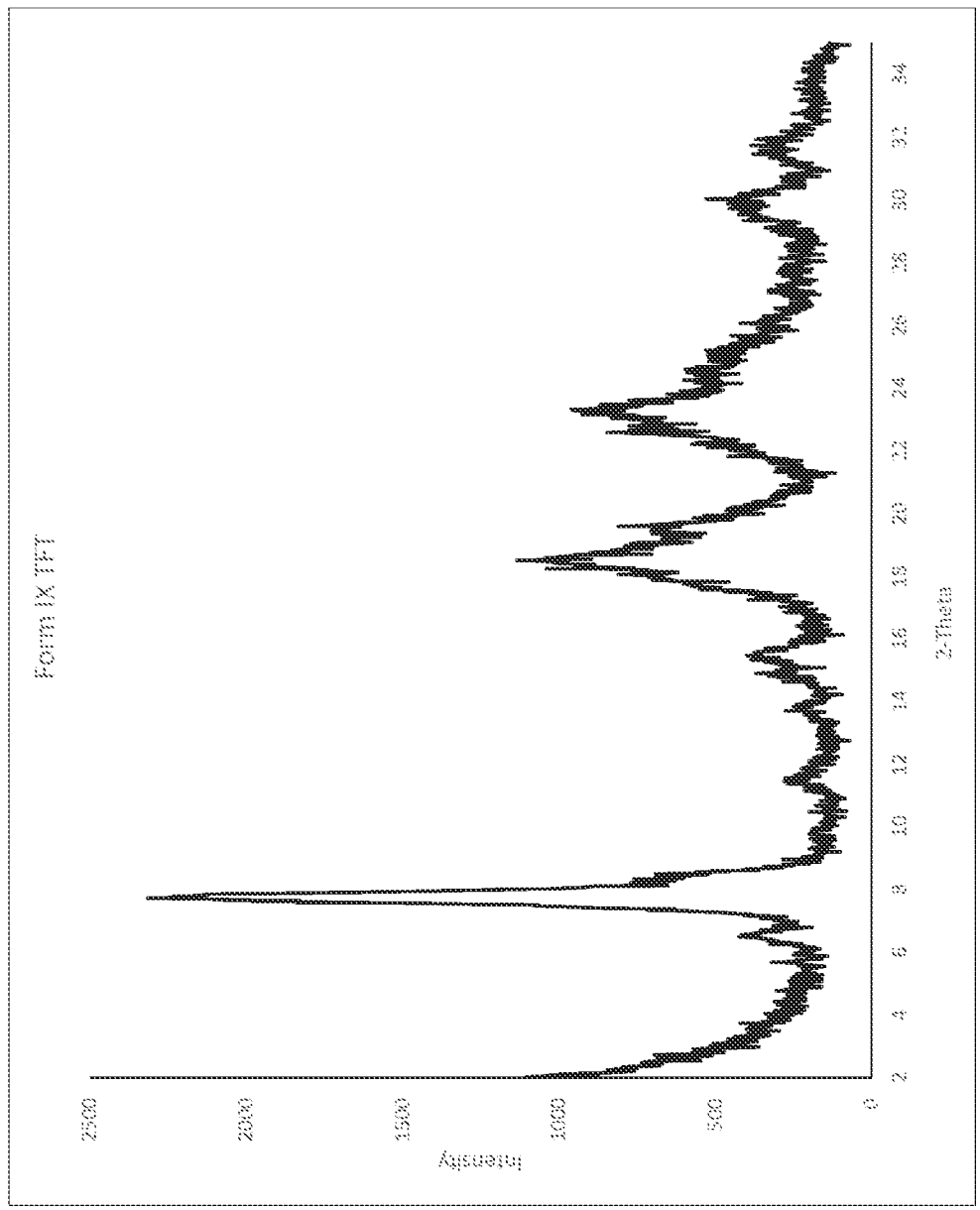
FIG. 19 depicts a powder X-ray diffraction pattern of Form IX of Compound 1.
Figure 20:
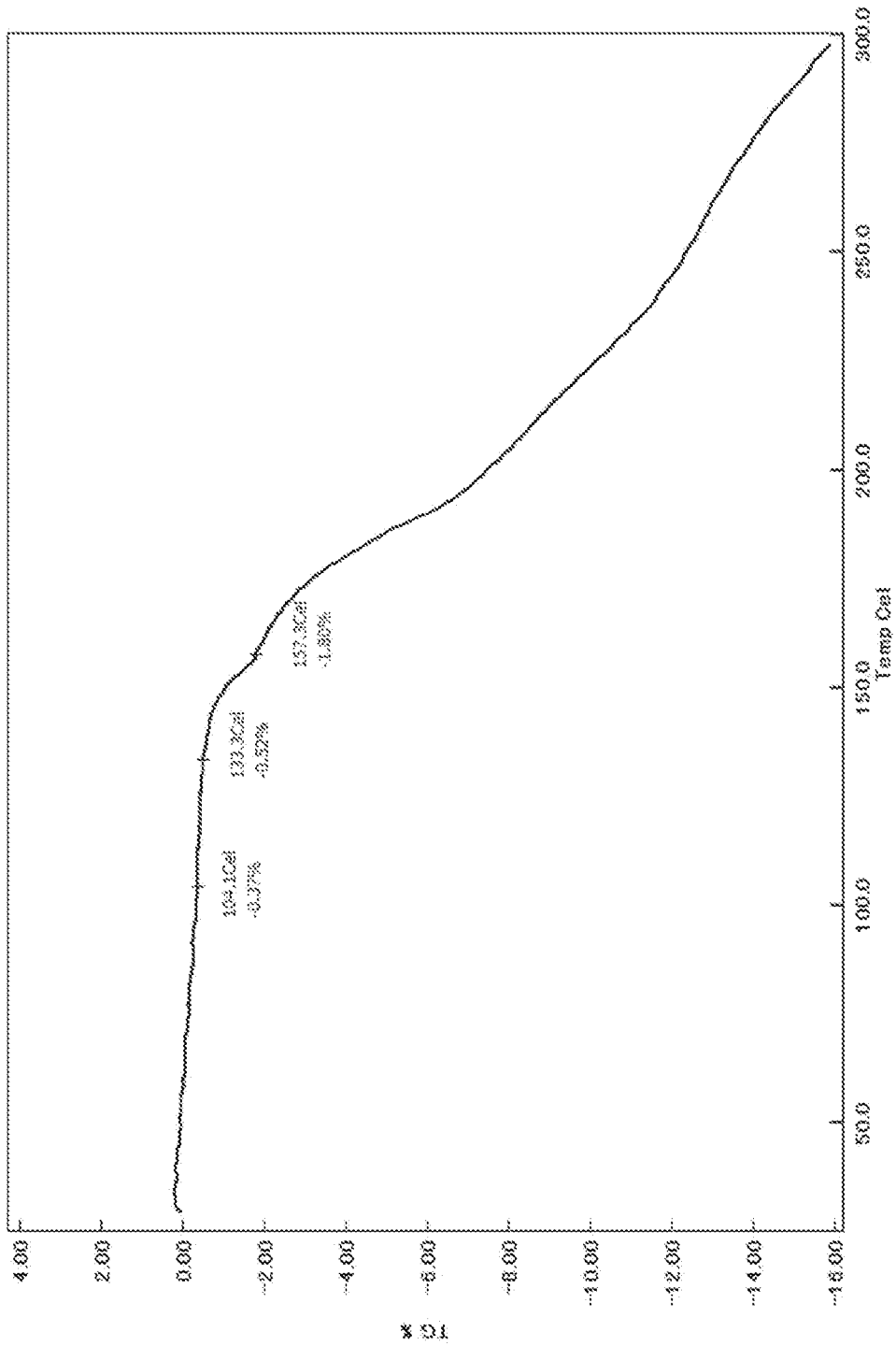
FIG. 20 depicts a TG thermogram of Form IX of Compound 1.
Figure 21:
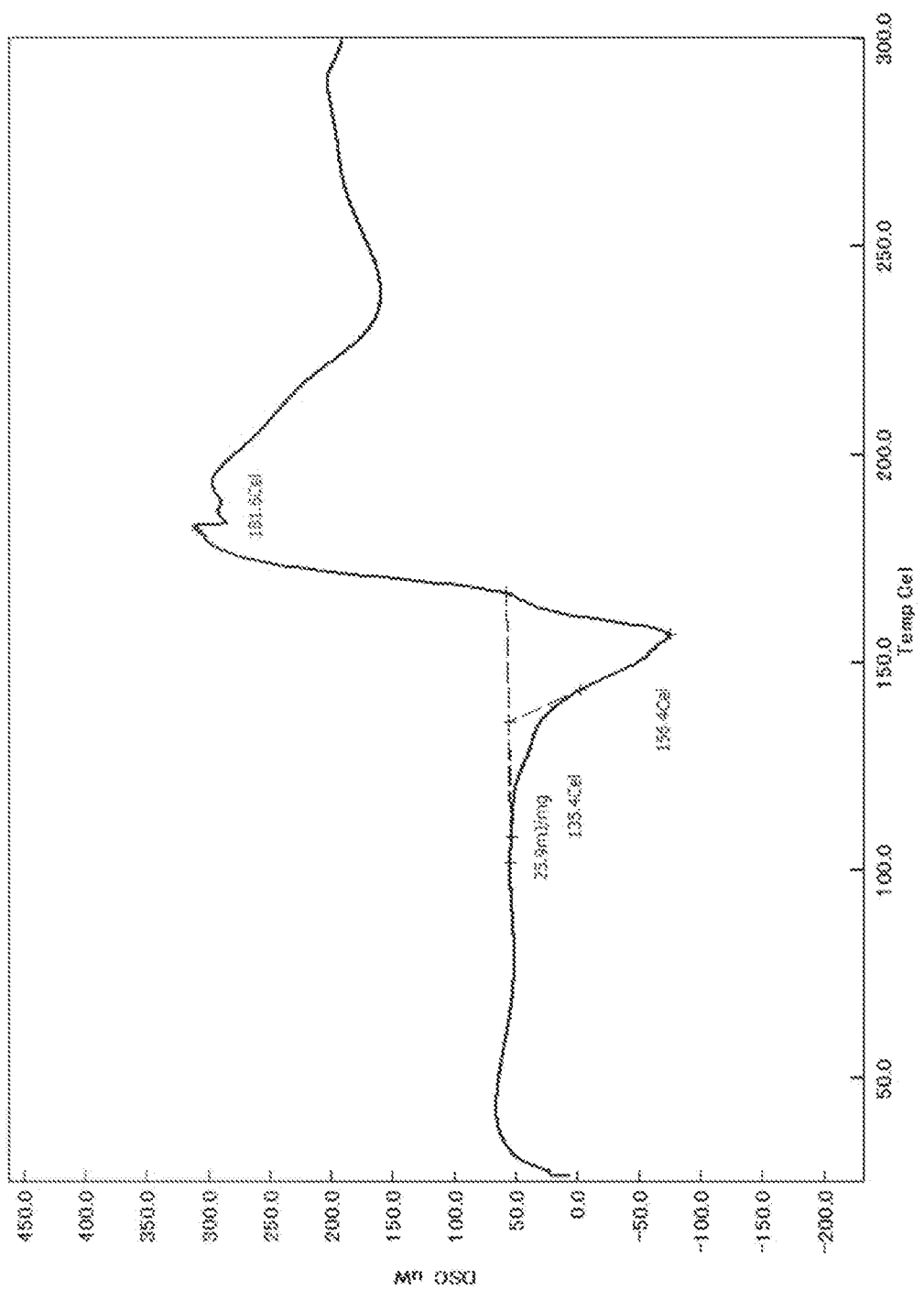
FIG. 21 depicts a DSC thermogram of Form IX of Compound 1.

In some embodiments, Form IX of Compound 1 is characterized by having at least two of the following:
a) an XRPD pattern substantially the same as the pattern shown in FIG. 19;
b) a TG thermogram substantially the same as the pattern shown in FIG. 20; and
c) a DSC thermogram substantially the same as the pattern shown in FIG. 21.

Form X of Compound 1

Figure 22:
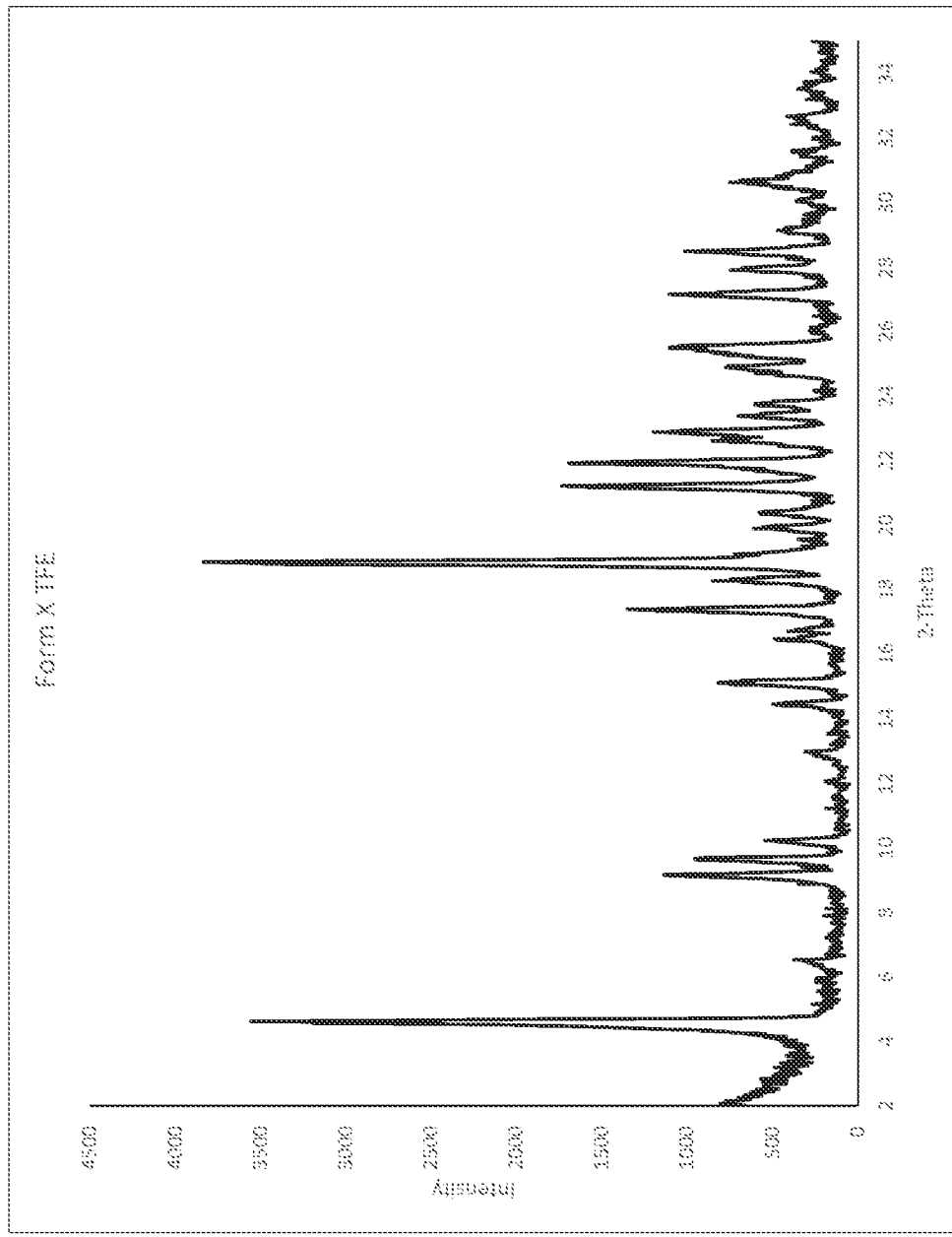
FIG. 22 depicts a powder X-ray diffraction pattern of Form X of Compound 1.

The present disclosure provides a crystalline form of Compound 1 characterized as Form X of Compound 1. In some embodiments, Form X of Compound 1 is a trifluoroethanol solvate. In some embodiments, Form X of Compound 1 is characterized by an XRPD pattern comprising at least three peaks selected from the group consisting of 4.6°, 9.1°, 9.6°, 17.4°, and 18.8° 2θ±0.2° 2θ. In some embodiments, Form X of Compound 1 is characterized by an XRPD pattern substantially the same as the pattern shown in FIG. 22.

Form X of Compound 1 may also be characterized by TG or DSC. In some embodiments, Form X of Compound 1 is characterized by a TG thermogram substantially the same as the pattern shown in FIG. 23, or by a DSC thermogram substantially the same as the pattern shown in FIG. 24.

Figure 23:
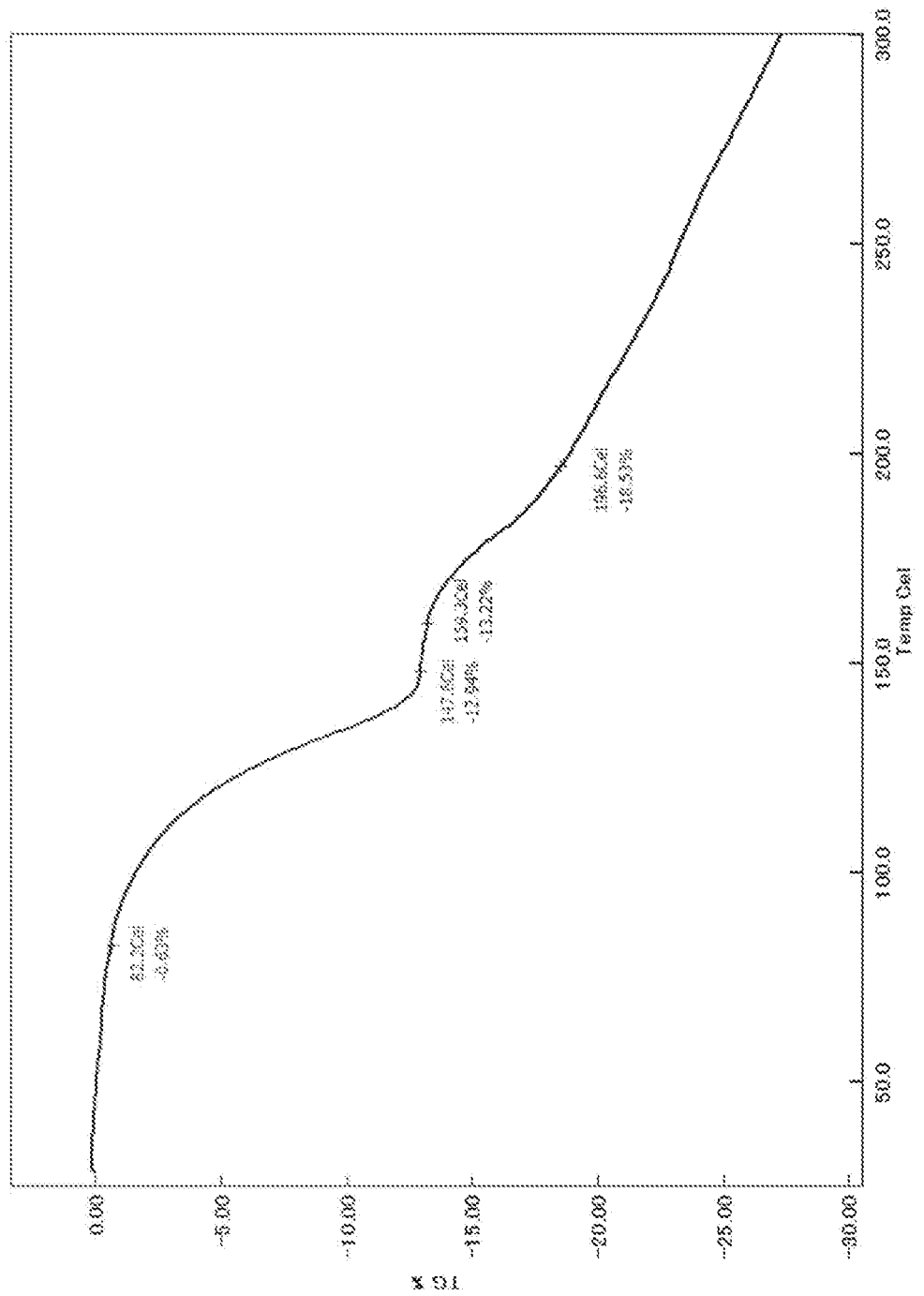
FIG. 23 depicts a TG thermogram of Form X of Compound 1.
Figure 24:
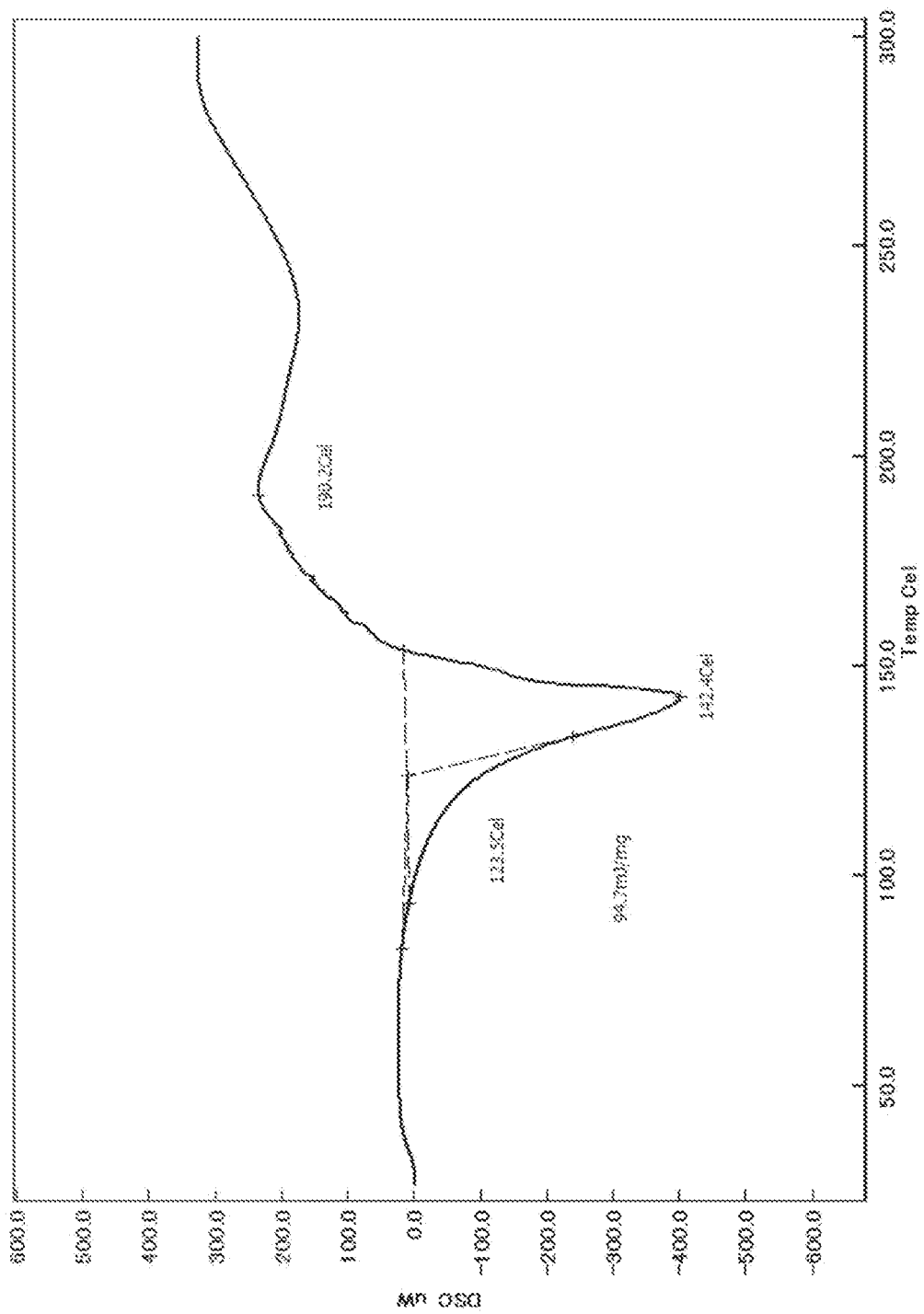
FIG. 24 depicts a DSC thermogram of Form X of Compound 1.

In some embodiments, Form X of Compound 1 is characterized by having at least two of the following:
a) an XRPD pattern comprising at least three peaks selected from the group consisting of 4.6°, 9.1°, 9.6°, 17.4°, and 18.8° 2θ±0.2° 2θ;
b) a TG thermogram substantially the same as the pattern shown in FIG. 23; and
c) a DSC thermogram substantially the same as the pattern shown in FIG. 24.

In some embodiments, the XRPD pattern comprises peaks at 4.6°, 9.1°, 9.6°, 17.4°, and 18.8° 2θ±0.2° 2θ. In some embodiments, the XRPD pattern comprises peaks at 4.6°, 9.1°, and 9.6° 2θ±0.2° 2θ. In some embodiments, the XRPD pattern comprises peaks at 4.6°, 9.1°, and 17.4° 2θ±0.2° 2θ. In some embodiments, the XRPD pattern comprises peaks at 4.6°, 9.1°, and 18.8° 2θ±0.2° 2θ. In some embodiments, the XRPD pattern comprises peaks at 4.6°, 9.6°, and 17.4° 2θ±0.2° 2θ. In some embodiments, the XRPD pattern comprises peaks at 4.6°, 9.6°, and 18.8° 2θ±0.2° 2θ. In some embodiments, the XRPD pattern comprises peaks at 4.6°, 17.4°, and 18.8° 2θ±0.2° 2θ. In some embodiments, the XRPD pattern comprises peaks at 9.1°, 9.6°, and 17.4° 2θ±0.2° 2θ. In some embodiments, the XRPD pattern comprises peaks at 9.1°, 9.6°, and 18.8° 2θ±0.2° 2θ. In some embodiments, the XRPD pattern comprises peaks at 9.1°, 17.4°, and 18.8° 2θ±0.2° 2θ. In some embodiments, the XRPD pattern comprises peaks at 9.6°, 17.4°, and 18.8° 2θ±0.2° 2θ.

Form XI of Compound 1

The present disclosure provides a crystalline form of Compound 1 characterized as Form XI of Compound 1. In some embodiments, Form XI of Compound 1 is a DMF solvate. In some embodiments, Form XI of Compound 1 is characterized by an XRPD pattern substantially the same as the pattern shown in FIG. 30.

Form XI of Compound 1 may also be characterized by TG or DSC. In some embodiments, Form XI of Compound 1 is characterized by a TG thermogram substantially the same as the pattern shown in FIG. 31 (top panel). In some embodiments, Form XI of Compound 1 is characterized by a DSC thermogram substantially the same as the pattern shown in FIG. 31 (bottom panel).

Figure 30:
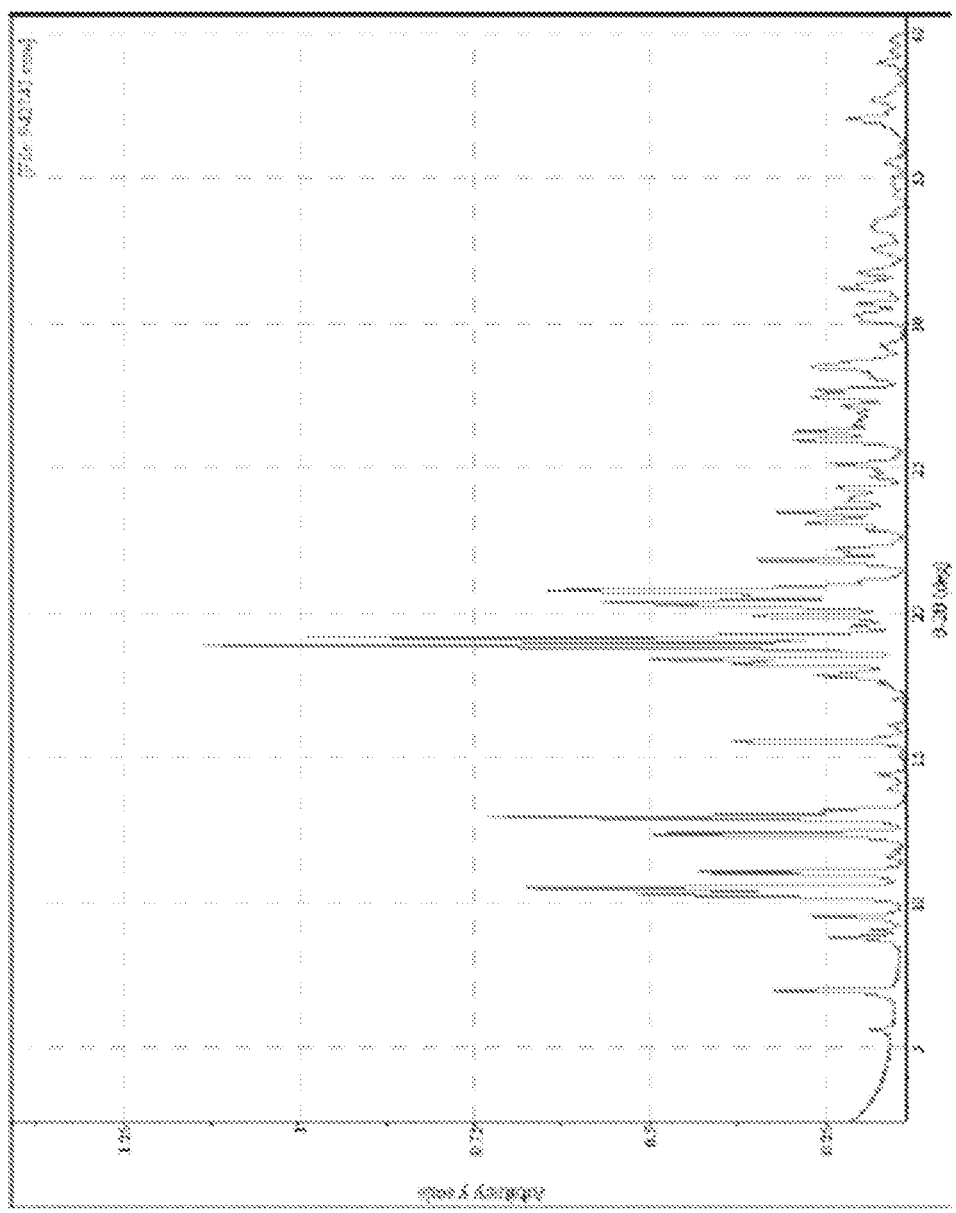
FIG. 30 depicts a powder X-ray diffraction pattern of Form XI of Compound 1.
Figure 31:
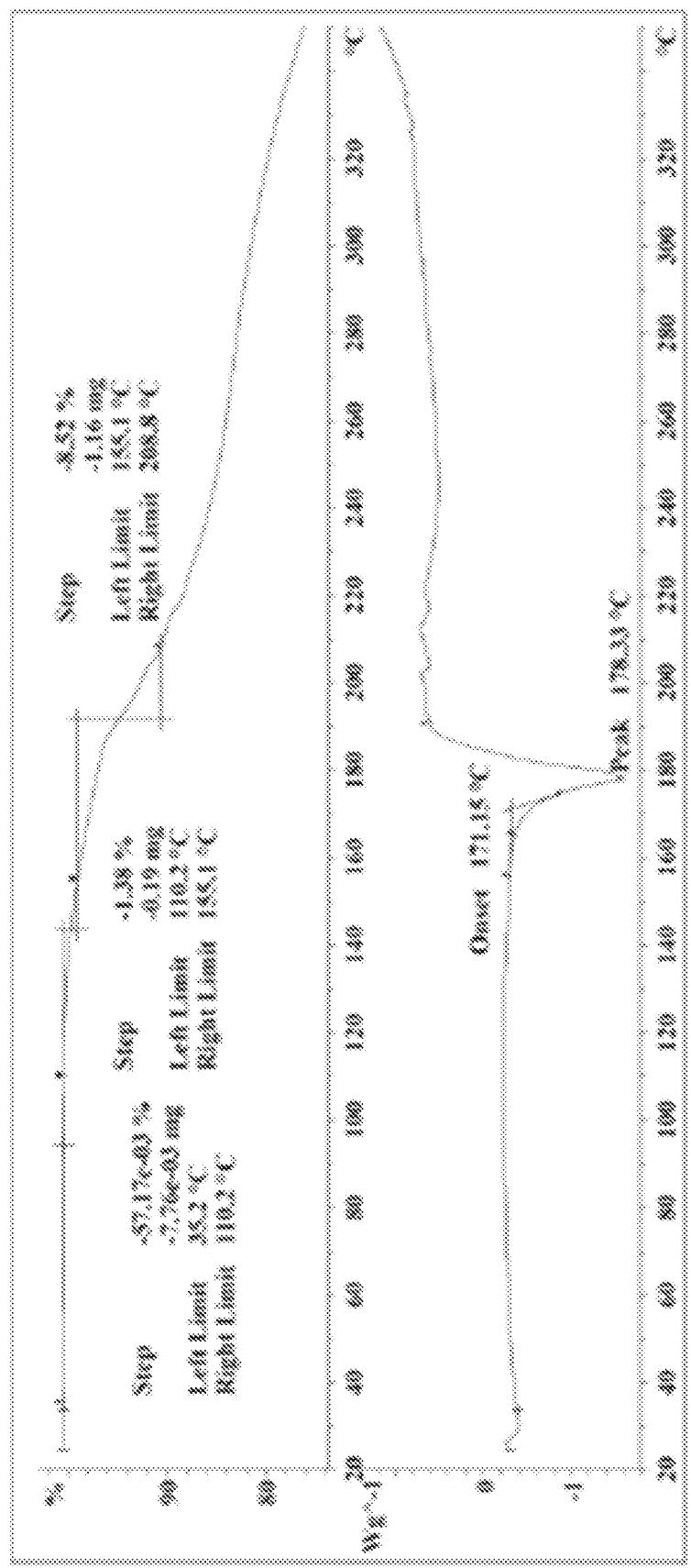
FIG. 31 depicts a TG thermogram (top panel) and a DSC thermogram (bottom panel) of Form XI of Compound 1.

In some embodiments, Form XI of Compound 1 is characterized by having at least two of the following:
  a) an XRPD pattern substantially the same as the pattern shown in FIG. 30;
  b) a TG thermogram substantially the same as the pattern shown in FIG. 31 (top panel); and
  c) a DSC thermogram substantially the same as the pattern shown in FIG. 31 (bottom panel).

Form XII of Compound 1

The present disclosure provides a crystalline form of Compound 1 characterized as Form XII of Compound 1. In some embodiments, Form XII of Compound 1 is characterized by an XRPD pattern substantially the same as the pattern shown in FIG. 32.

Form XII of Compound 1 may also be characterized by TG or DSC. In some embodiments, Form XII of Compound 1 is characterized by a TG thermogram substantially the same as the pattern shown in FIG. 33 (top panel). In some embodiments, Form XII of Compound 1 is characterized by a DSC thermogram substantially the same as the pattern shown in FIG. 33 (bottom panel).

Figure 32:
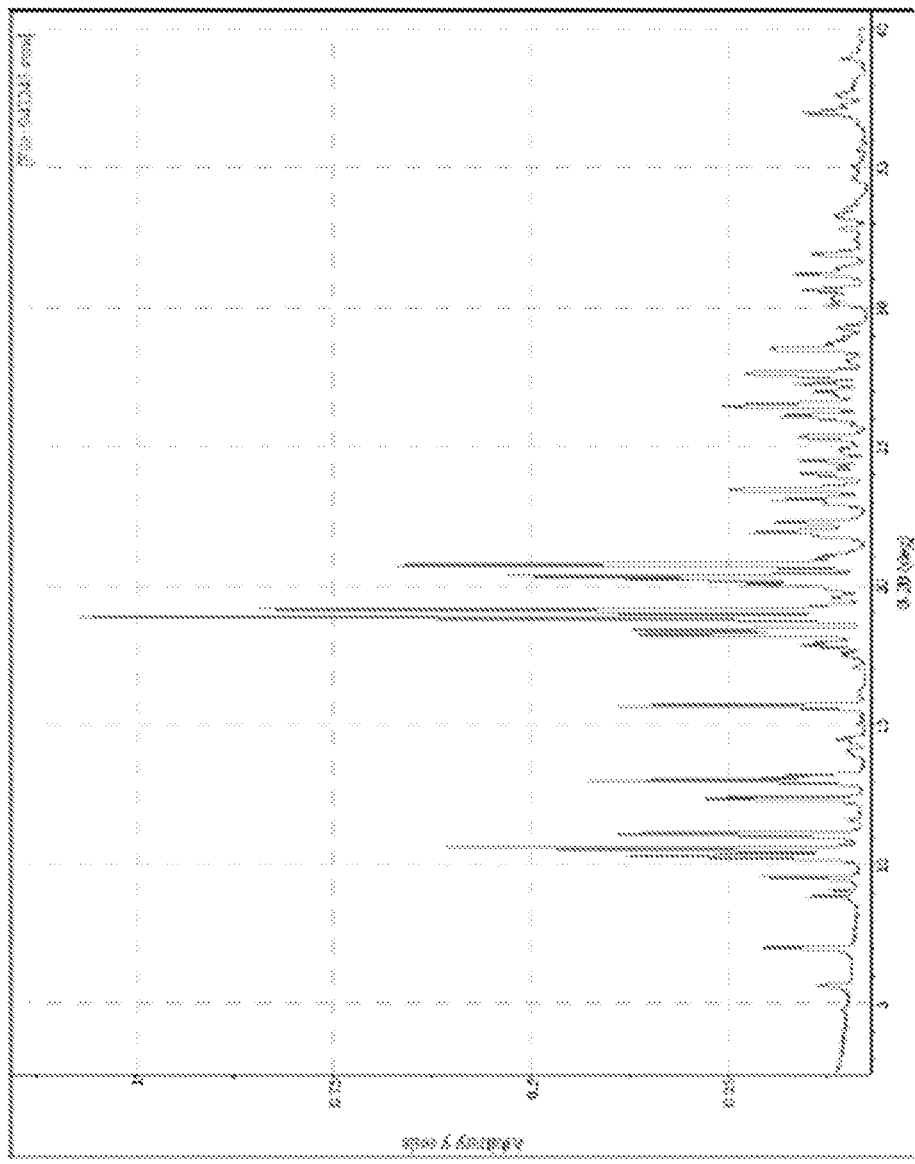
FIG. 32 depicts a powder X-ray diffraction pattern of Form XII of Compound 1.
Figure 33:
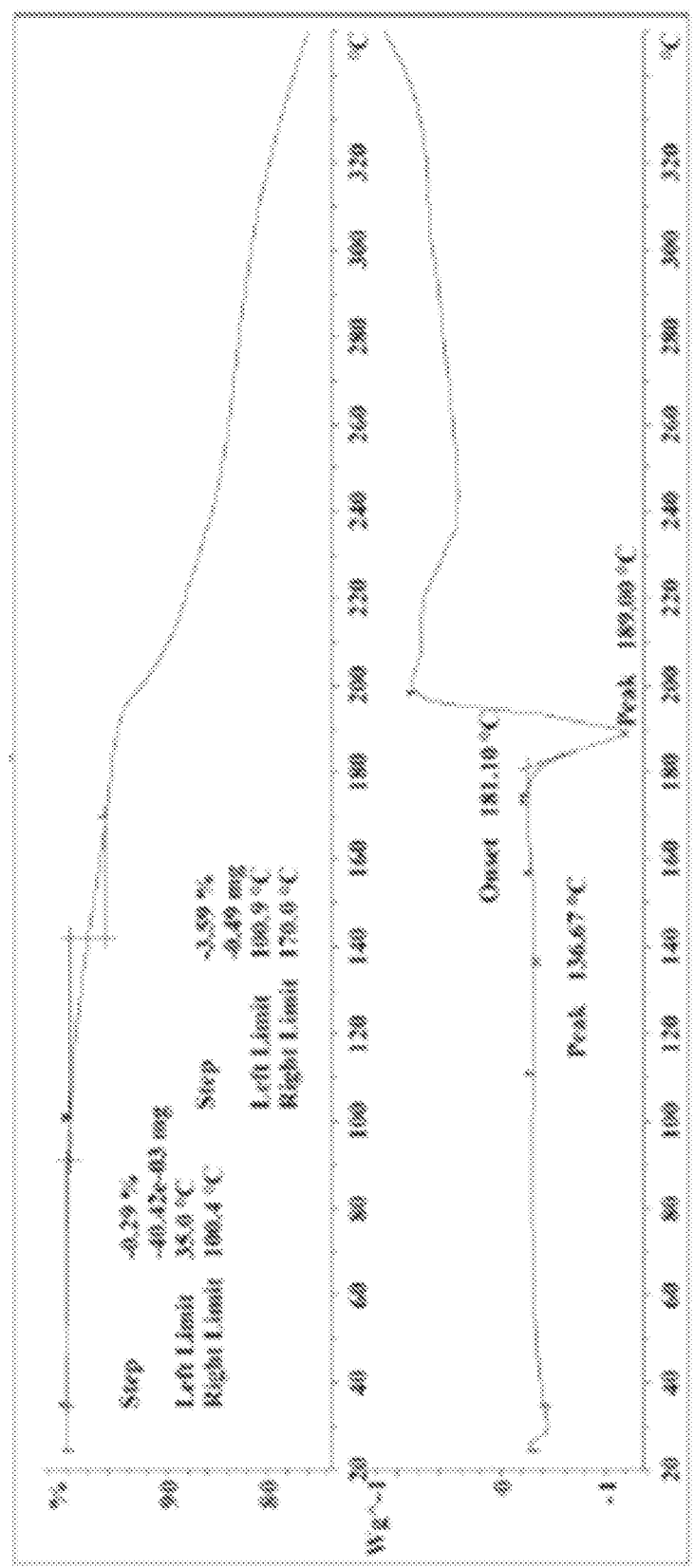
FIG. 33 depicts a TG thermogram (top panel) and a DSC thermogram (bottom panel) of Form XII of Compound 1.

In some embodiments, Form XII of Compound 1 is characterized by having at least two of the following:
  a. an XRPD pattern substantially the same as the pattern shown in FIG. 32;
  b. a TG thermogram substantially the same as the pattern shown in FIG. 33 (top panel); and
  c. a DSC thermogram substantially the same as the pattern shown in FIG. 33 (bottom panel).

In some embodiments, the crystalline forms of Compound I disclosed herein may be characterized by XRPD patterns having peaks listed in Table 2. All peak listings are in degrees 2θ±0.2° 2θ.

TABLE 2

XRPD Peaks of Crystalline Forms of Compound 1 (°2θ ± 0.2° 2θ)

| Form II | Form III | Form V | Form VI | Form VII | Form VIII | Form IX | Form X | Form XI | Form XII |
|---|---|---|---|---|---|---|---|---|---|
| 7.2 | 7.4 | 7.1 | 7.2 | 7.3 | 7.4 | 7.8 | 4.6 | 7.0 | 10.3 |
| 9.7 | 7.5 | 7.5 | 10.5 | 8.4 | 8.3 | 18.3 | 9.1 | 10.3 | 10.6 |
| 10.5 | 9.5 | 9.1 | 11.1 | 9.8 | 9.8 | 18.6 | 9.6 | 10.5 | 11.1 |
| 10.7 | 10.3 | 10.3 | 14.6 | 10.6 | 10.6 | 23.3 | 10.2 | 11.1 | 13.0 |
| 1.2 | 12.1 | 10.6 | 15.2 | 13.6 | 11.9 |  | 14.4 | 12.4 | 15.7 |
| 12.51 | 12.2 | 11.2 | 15.4 | 15.0 | 13.7 |  | 12.2 | 13.0 | 18.4 |
| 13.1 | 16.6 | 15.3 | 16.0 | 15.2 | 14.7 |  | 17.4 | 18.4 | 19.1 |
| 15.9 | 16.8 | 16.1 | 16.6 | 15.4 | 15.2 |  | 18.3 | 18.9 | 20.3 |
| 17.7 | 17.4 | 16.7 | 17.6 | 16.7 | 16.7 |  | 18.8 | 20.4 | 20.7 |
| 18.0 | 18.1 | 17.1 | 18.0 | 18.6 | 18.4 |  | 19.1 | 20.8 |  |
| 19.0 | 18.8 | 18.2 | 18.3 | 18.8 | 18.7 |  | 19.9 |  |  |
| 19.3 | 19.1 | 19.7 | 18.6 | 19.2 | 19.2 |  | 20.4 |  |  |
| 20.2 | 19.2 | 19.9 | 19.9 | 19.8 | 19.6 |  | 21.2 |  |  |
| 20.5 | 19.5 | 21.5 | 21.1 | 20.5 | 20.6 |  | 21.9 |  |  |
| 20.9 | 20.1 | 21.7 | 21.4 | 21.2 | 21.3 |  | 22.6 |  |  |

Solubility of Crystalline Forms I and II of Compound I

The aqueous solubility of Form II is summarized in Table 3:

TABLE 3

Aqueous Solubility of Form II (mg/mL) at 37° C.

| Solution | 2 hrs | 6 hrs | 24 hrs |
|---|---|---|---|
| pH 1.2 | >10 | >10 | >10 |
| pH 6.8 | 0.52 | 0.51 | 0.52 |

TABLE 3-continued

Aqueous Solubility of Form II (mg/mL) at 37° C.

| Solution | 2 hrs | 6 hrs | 24 hrs |
|---|---|---|---|
| 20 mM GCDC, pH 6.8 | 2.75 | 3.30 | 4.12 |

*GCDC is sodium glycochenodeoxycholate.

Form II of Compound 1 was found to be more soluble than Form I of Compound 1, the aqueous solubility of which is summarized in Table 4:

TABLE 4

Aqueous Solubility of Form I (mg/mL) at 37° C.

| Solution | 2 hrs | 6 hrs | 24 hrs |
|---|---|---|---|
| pH 1.2 | >10 | >10 | >10 |
| pH 6.8 | 0.08 | 0.08 | 0.07 |
| 20 mM GCDC, pH 6.8 | 0.96 | 0.98 | 0.97 |

Form II of Compound 1 is shown to have a higher aqueous solubility that Form 1 of Compound 1 at pH 6.8, which is within the pH range of the small intestine. While not being bound to any particular theory, the higher solubility of Form II of Compound 1 at this physiologically relevant pH may result in one or more pharmacokinetic or pharmacodynamic advantages such as higher bioavailability, lower dosing to reach therapeutic plasma concentrations, and lower patient-to-patient variability in efficacy at a particular dose. Higher aqueous solubility may also result in advantages in formulation development by obviating or lessening the need for methods typically used to enhance solubility or dissolution including particle size reduction, crystal engineering, salt formation, solid dispersion, use of surfactant, and complexation.

Preparation of Crystalline Forms of the Disclosure

Figure 25:
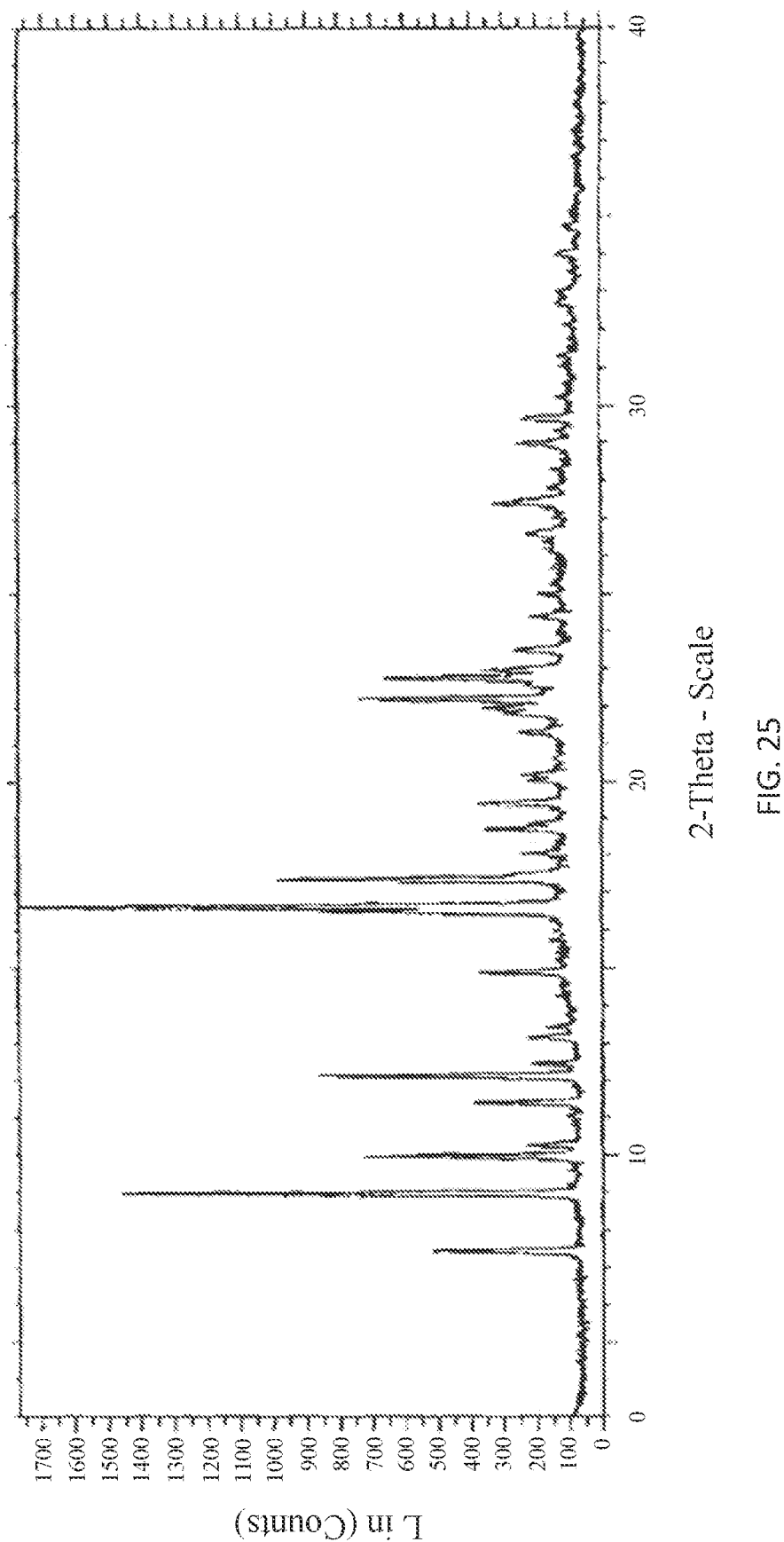
FIG. 25 depicts a powder X-ray diffraction pattern of Form I of Compound 1. Adapted from FIG. 2 of U.S. Pat. No. 9,758,528.

Forms II through XII of Compound 1 may be used during the synthesis or production of Form I of Compound 1. Form I of Compound 1 and methods of preparing Form I of Compound 1 are described in U.S. Pat. No. 9,758,528, hereby incorporated by reference in its entirety, particular with regard to synthesis and crystallization methods. The XRPD pattern of Form I of Compound 1 is depicted in FIG. 25. Methods of preparing Compound 1 before crystallization are described in U.S. Pat. Nos. 7,300,935, 8,058,280, 8,735,401, and 9,346,822, hereby incorporated by reference in their entireties.

In some embodiments, Form I of Compound 1 may be made by using any of Form II of Compound 1, Form III of Compound 1, Form IV of Compound 1, Form V of Compound 1, Form VI of Compound 1, Form VII of Compound 1, Form VIII of Compound 1, Form IX of Compound 1, Form X of Compound 1, Form XI of Compound 1, Form XII of Compound 1, or any combination thereof. In some embodiments, Form I of Compound 1 may be made from using any of solvated form of Compounds 1, for example, Form V of Compound 1, Form VI of Compound 1, Form VII of Compound 1, Form VIII of Compound 1, Form IX of Compound 1 Form X of Compound 1, Form XI of Compound 1, Form XII of Compound 1, or any combination thereof. For example, Form I of Compound 1 may be made by dissolving Form V of Compound 1 in DMSO at a temperature of about 35° C.+/−5° C. Ethanol is then added to the mixture. The mixture is then filtered and the solid washed with ethanol while maintaining the temperature of the mixture at about 35° C.+/−5° C. and the mixture is stirred at about 35° C.+/−5° C. for about one hour, cooled to about 25° C.+/−5° C. and stirred for about 12 hours or more. The resulting precipitate affords Form I of Compound 1.

Figure 27:
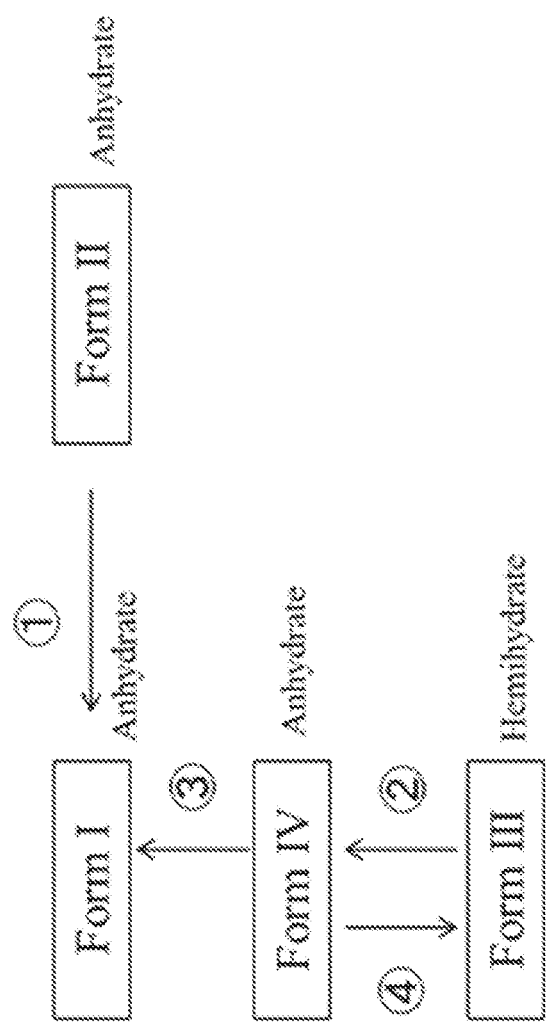
FIG. 27 depicts the conversion of Forms II, III, and IV to Form I. ① Competitive slurry in EtOH at 25° C. and 40° C. and EtOAc at 5° C., 25° C., and 40° C. ② Heating. ③ Heating. ④ Under room temperature and normal humidity environment.
Figure 28:
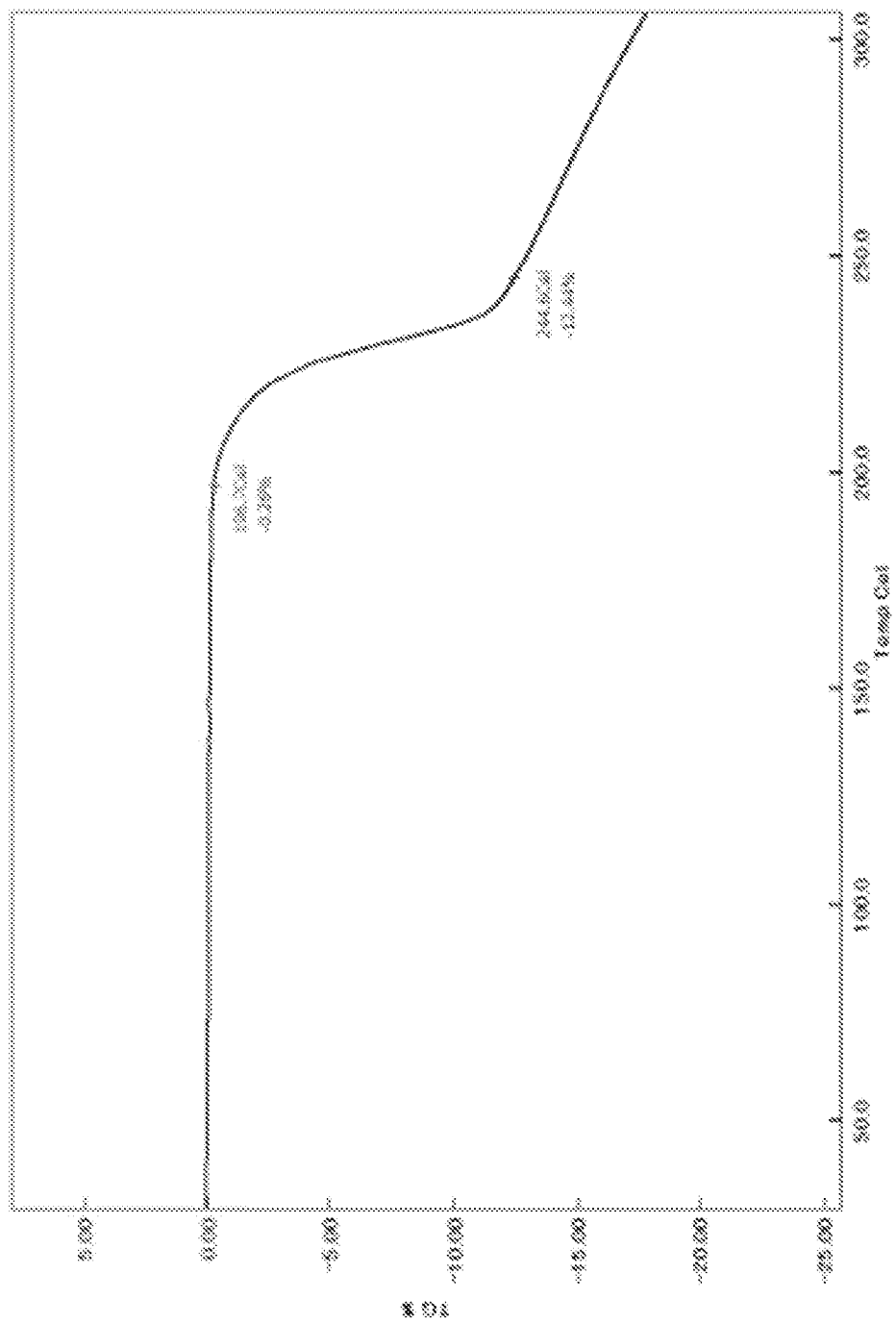
FIG. 28 depicts a TG thermogram of Form I of Compound 1.
Figure 29:
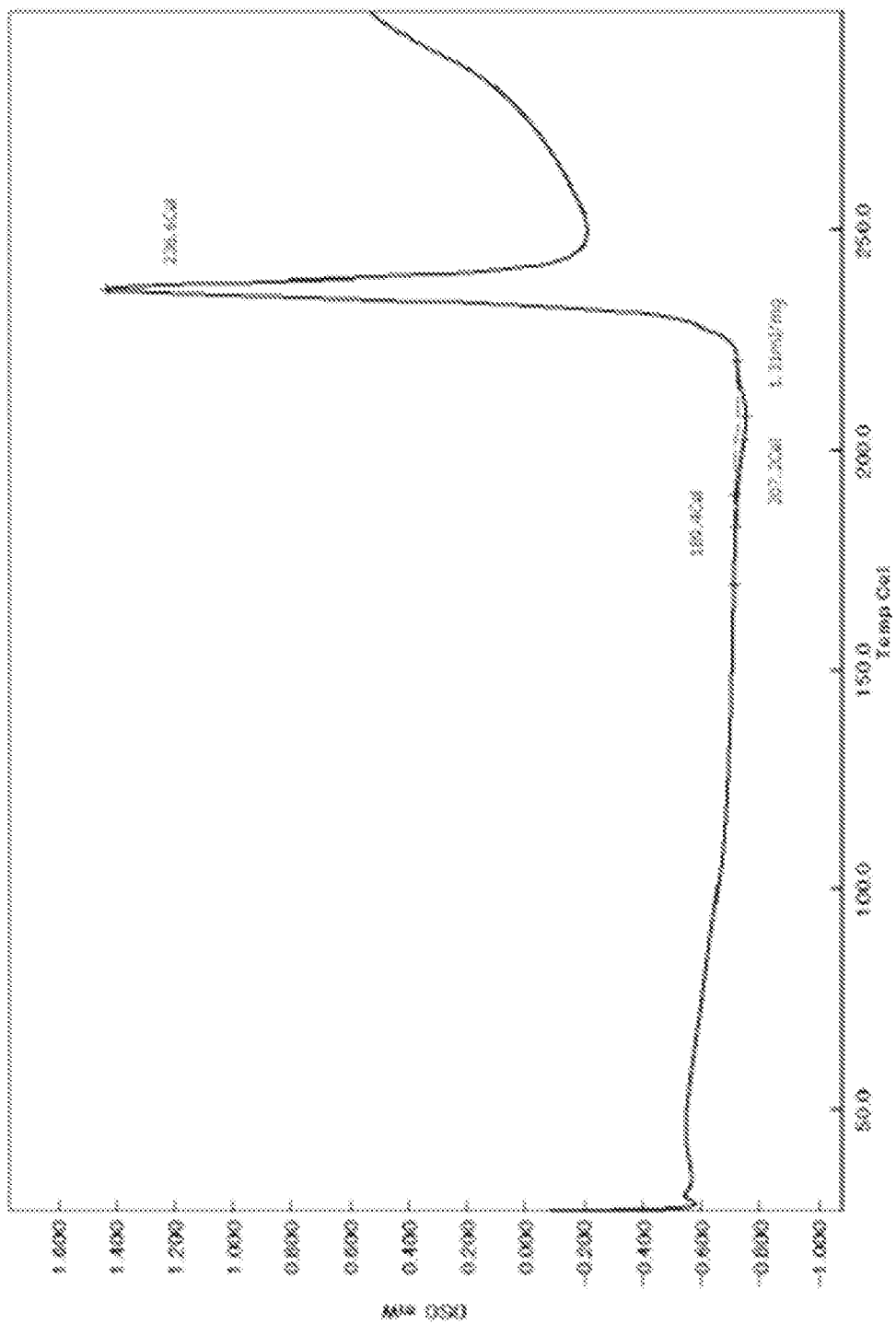
FIG. 29 depicts a DSC thermogram of Form I of Compound 1.

In some embodiments, Form III of Compound I is transformed to Form IV by heating to above about 52° C. In certain such embodiments, Form I is recrystallized after Form IV melting, which occurs between about 197° C. to about 201° C. In certain such embodiments, Form IV is not able to be isolated due to a reversible change to Form III at room temperature under normal humidity. The conversion of Forms II, III, and IV to Form I is illustrated in FIG. 27.

The disclosure provides a method for preparing an amorphous form of Compound 1. In certain such embodiments, Form I of Compound 1 is dissolved in an approximately 1:24 ratio (v/v) of dimethyl sulfoxide and 1,4-dioxane. The dimethyl sulfoxide and 1,4-dioxane are then evaporated by vacuum freeze drying to afford the amorphous form of Compound 1.

The disclosure provides methods for preparing Form II of Compound 1. In certain such embodiments, Form 1 of Compound 1 is dissolved in a mixture of DMF and acetone (about 6:94, v/v) at about 25° C. The resulting solution is stirred at a temperature of about −15° C. to about −25° C. for about 3 days to generate a suspension. The solids formed are isolated by vacuum filtration and vacuum dried at about 60° C. for about 4 hours, affording Form II of Compound 1.

In some embodiments, the method for preparing Form II of Compound 1 comprises dissolving Form 1 of Compound 1 in a mixture of DMF and acetone (about 80:20, v/v) at about 40° C. Acetone at room temperature is then added to the mixture to reach a DMF:acetone ratio of about 12.5:87.5, v/v. The mixture is then seeded with about 0.5% (wt) of crystals of Form II. The mixture is placed in a freezer at about −15° C. to about −25° C. overnight, after which the resulting suspension is vacuum filtered and the wet cake is washed with cold acetone and dried under vacuum at about 62° C. to about 65° C. for about 5 hours to afford Form II of Compound 1.

In some embodiments, the method for preparing Form II of Compound 1 comprises dissolving Form 1 of Compound 1 in DMF at about 40° C. Acetone at room temperature is added to the mixture to reach a DMF:acetone ratio of about 10:90, v/v. The mixture is then seeded with about 0.5% (wt) of Form II. The mixture is placed in a freezer at about −15° C. to about −25° C. overnight, after which the resulting suspension is vacuum filtered and the wet cake is washed with cold acetone and dried under vacuum at about 62° C. to about 65° C. for about 5 hours to afford Form II of Compound 1.

The disclosure provides a method for preparing Form III of Compound 1. In some embodiments, Form III of Compound 1 is made by dissolving Form 1 of Compound 1 in DMF, precipitating with water, and storing at about −10° C. for about three days.

The disclosure provides a method for preparing Form IV of Compound 1. In certain such embodiments, Form III of Compound I is transformed to anhydrate Form IV by heating Form III to between about 79° C. and about 197° C.

The disclosure provides a method for preparing Form V of Compound 1. In certain such embodiments, the amorphous form of Compound 1 is dissolved into toluene to make an approximately 10 mg/mL solution at about 55° C. The toluene is then evaporated by nitrogen flow at about 55° C. to afford Form V of Compound 1.

The disclosure provides a method for preparing Form VI of Compound 1. In certain such embodiments, the amorphous form of Compound 1 is dissolved into anisole to make an approximately 10 mg/mL solution at about 55° C. An approximately equivalent volume of heptane is added into the anisole solution to make an approximately 5 mg/mL solution at about 55° C. The anisole and heptane are evaporated by nitrogen flow at about 55° C. to afford Form VI of Compound 1.

The disclosure provides a method for preparing Form VII of Compound 1. In certain such embodiments, the amorphous form of Compound 1 is dissolved into 2-propanol to make an approximately 10 mg/mL solution at about 55° C. An approximately 2.5 times volume of water is added into the 2-propanol solution to make an approximately 2.9 mg/mL solution at about 55° C. The solution is cooled from about 55° C. to about 10° C. at a rate of about 3° C./hour with stirring. The crystallized solid is collected by filtration to afford Form VII of Compound 1.

The disclosure provides a method for preparing Form VIII of Compound 1. In certain such embodiments, Form I of Compound 1 is dispersed into a mixture of 1,4-dioxane and water (about 1:1, v/v) to make slurry conditions at a concentration of about 20 mg/mL. The slurry is aged by stirring for about three days at about 25° C. The dispersed powder is collected by filtration to afford Form VIII of Compound 1.

The disclosure provides a method for preparing Form IX of Compound 1. In certain such embodiments, the amorphous form of Compound 1 is dissolved into α,α,α-trifluorotoluene to make an approximately 10 mg/mL solution at about 55° C. An approximately equivalent volume of heptane is added into the α,α,α-trifluorotoluene solution to make an approximately 5 mg/mL solution at about 55° C. The α,α,α-trifluorotoluene and heptane are evaporated by nitrogen flow at about 55° C. to afford Form IX of Compound 1.

The disclosure provides a method for preparing Form X of Compound 1. In certain such embodiments, the amorphous form of Compound 1 is dissolved into trifluoroethanol to make an approximately 200 mg/mL solution at about 55° C. An approximately equivalent volume of diisopropylether is added into the trifluoroethanol solution to make an approximately 100 mg/mL solution at about 55° C. The solution is cooled from about 55° C. to about 10° C. at a rate of about 3° C. per hour with stirring. The crystallization solid in suspension is collected by filtration to afford Form X of Compound 1.

The disclosure provides several methods for preparing Form XI of Compound 1. In certain such embodiments, Form I of Compound 1 is dissolved in DMF at ambient temperature. The resulting clear solution is cooled to about −10° C. Aliquots of methyl tert-butyl ether (MTBE) are added to reach an about DMF:MTBE 50:50 volume ratio and seeds of Form II of Compound 1 are added. An additional amount of MTBE is added to reach an about DMF:MTBE 25:75 volume ratio. The resulting solution is stirred at about −10° C. overnight to afford a suspension. After a total of about 4 days of stirring at about −10° C., the solids are isolated cold by vacuum filtration and washed with cold MTBE to afford Form XI of Compound 1.

In some embodiments, the method for preparing Form XI of Compound 1 comprises dissolving Form I of Compound 1 in DMF at ambient temperature. The resulting solution is cooled to about −10° C. Aliquots of isopropanol are added to reach an about DMF:isopropanol 50:50 volume ratio and seeds of Form II of Compound 1 are added. The solution is allowed to stir at about −10° C. overnight. After a total of about 4 days of stirring at about −10° C., the solids of the resulting suspension are diluted with cold isopropanol and are isolated by vacuum filtration to afford Form XI of Compound 1.

The disclosure provides methods for preparing Form XII of Compound 1. In certain such embodiments, Form I of Compound 1 is dissolved in DMF at ambient temperature. The resulting solution is added dropwise with stirring into acetone without causing precipitation. The DMF:acetone volume ratio is about 6:94. The solution is allowed to stir at about −15° C. to about −25° C. for about 2 days, resulting in a solution that is stirred additionally for about 1 day, producing a suspension. The solids are isolated cold by vacuum filtration to afford Form XII of Compound 1.

In some embodiments, the method for preparing Form XII of Compound 1 comprises dissolving Form I of Compound 1 in DMF:acetone (about 80:20 (v/v)) at about 40° C. Additional aliquots of DMF are added until complete dissolution is observed, reaching a DMF:acetone ratio of about 85:15 (v/v). The resulting solution is stirred at ambient temperature and acetone is added slowly to reach a DMF:acetone ratio of about 12.5:87.5 (v/v). The resulting solution is seeded with Form II of Compound 1, producing a solution that is cooled to about −15° C. to about −25° C. overnight. The solids are isolated cold by vacuum filtration at about −15° C. to about −25° C. The solids are washed with cold acetone at about −15° C. to about −25° C. to afford Form XII of Compound 1.

In some embodiments, the method for preparing Form XII of Compound 1 comprises dissolving Form I of Compound 1 in DMF at about 40° C. Additional aliquots of DMF are added until complete dissolution is observed. The resulting solution is stirred at ambient temperature and acetone is added slowly to reach a DMF:acetone ratio of about 11:89 (v/v). The clear solution is seeded with Form II of Compound 1. Additional acetone is added to reach a DMF:acetone ratio of about 10:90 (v/v) and the sample is allowed to stir at ambient temperature, producing a suspension that is maintained at about −15° C. to about −25° C. overnight. The solids are isolated cold by vacuum filtration and washed with cold acetone to afford Form XII of Compound 1.

Pharmaceutical Compositions

The disclosed crystalline forms may be used on their own but if administered to a subject will generally be administered in the form of a pharmaceutical composition in which one or more disclosed crystalline forms of Compound 1 is in association with a pharmaceutically acceptable carrier. Conventional procedures for the selection and preparation of suitable pharmaceutical compositions are described in, for example, "Pharmaceuticals—The Science of Dosage Form Designs," M. E. Aulton, Churchill Livingstone, 1988, which is hereby incorporated by reference in its entirety.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as one or more crystalline forms of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., *Remington's Pharmaceutical Sciences*, Mack Publishing Co., Easton, Pa. 1975.

In some embodiments, the disclosure provides for a pharmaceutical composition comprising one or more crystalline forms disclosed herein. In some embodiments, the disclosure provides for a pharmaceutical composition comprising only one crystalline form disclosed herein. In some embodiments, the disclosure provides for a pharmaceutical composition comprising Form II of Compound 1. In other embodiments, the disclosure provides for a pharmaceutical composition comprising two or more crystalline forms disclosed herein. For example, a pharmaceutical composition comprising Compound 1 can comprise Form I of Compound 1 and Form II of Compound 1.

In some embodiments, the disclosure provides for a pharmaceutical composition comprising Form III of Compound 1. In some embodiments, the disclosure provides for a pharmaceutical composition comprising Form V of Compound 1. In some embodiments, the disclosure provides for a pharmaceutical composition comprising Form VI of Compound 1. In some embodiments, the disclosure provides for a pharmaceutical composition comprising Form VII of Compound 1. In some embodiments, the disclosure provides for a pharmaceutical composition comprising Form VIII of Compound 1. In some embodiments, the disclosure provides for a pharmaceutical composition comprising Form IX of Compound 1. In some embodiments, the disclosure provides for a pharmaceutical composition comprising Form X of Compound 1. In some embodiments, the disclosure provides for a pharmaceutical composition comprising Form XI of Compound 1. In some embodiments, the disclosure provides for a pharmaceutical composition comprising Form XII of Compound 1.

In some embodiments, the disclosure provides for a pharmaceutical composition comprising Form II of Compound 1 and a pharmaceutically acceptable carrier. In some embodiments, the disclosure provides for a pharmaceutical composition comprising Form I and Form II of Compound 1 and a pharmaceutically acceptable carrier.

In some embodiments, the disclosure provides for a pharmaceutical composition comprising Form III of Compound 1 and a pharmaceutically acceptable carrier. In some embodiments, the disclosure provides for a pharmaceutical composition comprising Form V of Compound 1 and a pharmaceutically acceptable carrier. In some embodiments, the disclosure provides for a pharmaceutical composition comprising Form VI of Compound 1 and a pharmaceutically acceptable carrier. In some embodiments, the disclosure provides for a pharmaceutical composition comprising Form VII of Compound 1 and a pharmaceutically acceptable carrier. In some embodiments, the disclosure provides for a pharmaceutical composition comprising Form VIII of Compound 1 and a pharmaceutically acceptable carrier. In some embodiments, the disclosure provides for a pharmaceutical composition comprising Form IX of Compound 1 and a pharmaceutically acceptable carrier. In some embodiments, the disclosure provides for a pharmaceutical composition comprising Form X of Compound 1 and a pharmaceutically acceptable carrier. In some embodiments, the disclosure provides for a pharmaceutical composition comprising Form XI of Compound 1 and a pharmaceutically acceptable carrier. In some embodiments, the disclosure provides for a pharmaceutical composition comprising Form XII of Compound 1 and a pharmaceutically acceptable carrier.

In some embodiments, the disclosure provides for a pharmaceutical composition comprising two or more of Forms II, III, V, VI, VII, VIII, IX, X, XI, or XII of Compound 1 and a pharmaceutically acceptable carrier. In some embodiments, the disclosure provides for a pharmaceutical composition comprising two or more of Forms I, II, III, V, VI, VII, VIII, IX, X, XI, or XII of Compound 1 and a pharmaceutically acceptable carrier.

Depending on the mode of administration, the pharmaceutical composition will comprise from about 0.05 to about 99 wt % (percent by weight), more particularly from about 0.05 to about 80 wt %, still more particularly from about 0.10 to about 70 wt %, and even more particularly from about 0.10 to about 50 wt % of one or more disclosed crystalline forms, all percentages by weight being based on total composition.

Pharmaceutical compositions of the present disclosure may comprise a therapeutically effective amount of one or more disclosed crystalline forms formulated together with one or more pharmaceutically acceptable carriers. Examples of pharmaceutically acceptable carriers include sugars such as lactose, dextrose, mannitol, glucose and sucrose; starches such as starches derived from corn, wheat or potato and other pharmaceutical grade starches such as sodium starch glycolate; cellulose and its derivatives such as sodium carboxymethyl cellulose, methyl cellulose, ethyl cellulose, hydroxypropyl cellulose, cellulose acetate, and microcrystalline cellulose; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; lubricants such as sodium lauryl sulfate and magnesium stearate; coloring agents; releasing agents; coating agents; sweetening, flavoring and perfuming agents; preservatives and antioxidants.

Methods of Treatment and Uses

The present disclosure provides a method of treating a disorder comprising administering an effective amount of one or more crystalline forms, or pharmaceutical compositions comprising the one or more crystalline forms, described herein to thereby treat the disorder in a subject in need thereof.

In some embodiments of the methods and uses of the disclosure, the disorder is a hormone-dependent condition. Hormone-dependent conditions may include sex hormone-dependent cancer (e.g., prostate cancer, uterine cancer, breast cancer, and ovarian cancer), bone metastasis of sex hormone-dependent cancer, prostatic hypertrophy, hysteromyoma (uterine fibroids), adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, heavy menstrual bleeding, and symptoms associated with these conditions. Such symptoms may include anemia, irregular periods, spotting, inflammation, pain, fatigue, urinary obstruction, urinary frequency, incontinence, constipation, anxiety, sleep disturbance, decrease in quality of life, difficulty with activities of daily living, female sexual dysfunction, and depression. In some embodiments of the methods and uses of the disclosure, the hormone-dependent condition is prostate cancer, uterine cancer, breast cancer, or ovarian cancer. Additional disorders that Compound 1 is useful for treating are described in U.S. Pat. Nos. 7,300,935, 8,058,280, 8,735,401, 9,346,822, WO2018060501, and WO2018060463, incorporated herein by reference in their entireties.

In some embodiments of the methods and uses of the disclosure, the hormone-dependent condition is prostate cancer. In some embodiments of the methods and uses of the disclosure, the hormone-dependent condition is uterine cancer. In some embodiments of the methods and uses of the disclosure, the hormone-dependent condition is breast cancer. In some embodiments of the methods and uses of the disclosure, the hormone-dependent condition is ovarian cancer. In some embodiments of the methods and uses of the disclosure, the hormone-dependent condition is uterine fibroids. In some embodiments of the methods and uses of the disclosure, the hormone-dependent condition is heavy menstrual bleeding associated with uterine fibroids. In some embodiments of the methods and uses of the disclosure, the hormone-dependent condition is pain or other symptoms associated with uterine fibroids. In some embodiments of the methods and uses of the disclosure, the hormone-dependent condition is endometriosis. In some embodiments of the methods and uses of the disclosure, the hormone-dependent condition is pain associated with endometriosis. In some embodiments of the methods and uses of the disclosure, the hormone-dependent condition is adenomyosis. In some embodiments of the methods and uses of the disclosure, the hormone-dependent condition is heavy menstrual bleeding.

A "patient" or "subject" is a mammal. Examples of mammals may include, but are not limited to, any member of the class Mammalia including humans; non-human primates such as chimpanzees, monkeys, baboons, and rhesus monkeys; cattle, horses, sheep, goats, and swine; rabbits, dogs, and cats; and rodents such as rats, mice and guinea pigs. In some embodiments, the patient or subject is a human.

The terms "effective amount" or "therapeutically effective amount" when used in connection with one or more crystalline forms or pharmaceutical compositions of the disclosure may refer to a sufficient amount of the one or more crystalline forms or pharmaceutical compositions to provide the desired biological result. That result can be reduction and/or alleviation of the signs, symptoms, or causes of a disorder, or any other desired alteration of a biological system. For example, an "effective amount" for therapeutic use may be the amount of the pharmaceutical composition comprising one or more crystalline forms as disclosed herein required to provide a clinically significant decrease in a disorder. An appropriate "effective amount" in any individual case may be determined by one of ordinary skill in the art using routine experimentation.

As used herein, the terms "treat" or "treatment" or cognates thereof, are meant to indicate a postponement of development of disorders; and/or reducing severity of such symptoms that will or are expected to develop. Thus, these terms may include ameliorating existing disorder symptoms; preventing additional symptoms; ameliorating or preventing the underlying causes of symptoms; inhibiting the disorder, e.g., arresting the development of the disorder; relieving the disorder; causing regression of the disorder; relieving a symptom caused by the disorder; or stopping or alleviating the symptoms of the disorder.

The terms "administered," "administration," or "administering" as used in this disclosure may refer to either directly administering one or more crystalline forms or pharmaceutical compositions of the disclosure to a subject.

The present disclosure provides a method of treating a disorder comprising administering an effective amount of Form II of Compound 1 to thereby treat the disorder in a subject in need thereof. The present disclosure provides a method of treating a disorder comprising administering an effective amount of Form III of Compound 1 to thereby treat the disorder in a subject in need thereof. The present disclosure provides a method of treating a disorder comprising administering an effective amount of Form V of Compound 1 to thereby treat the disorder in a subject in need thereof. The present disclosure provides a method of treating a disorder comprising administering an effective amount of Form VI of Compound 1 to thereby treat the disorder in a subject in need thereof. The present disclosure provides a method of treating a disorder comprising administering an effective amount of Form VII of Compound 1 to thereby treat the disorder in a subject in need thereof. The present disclosure provides a method of treating a disorder comprising administering an effective amount of Form VIII of Compound 1 to thereby treat the disorder in a subject in need thereof. The present disclosure provides a method of treating a disorder comprising administering an effective amount of Form IX of Compound 1 to thereby treat the disorder in a subject in need thereof. The present disclosure provides a method of treating a disorder comprising administering an effective amount of Form X of Compound 1 to thereby treat the disorder in a subject in need thereof. The present disclosure provides a method of treating a disorder comprising administering an effective amount of Form XI of Compound 1 to thereby treat the disorder in a subject in need thereof. The present disclosure provides a method of treating a disorder comprising administering an effective amount of Form XII of Compound 1 to thereby treat the disorder in a subject in need thereof. The present disclosure provides a method of treating a disorder comprising administering an effective amount of a mixture of two or more of Forms II, III, V, VI, VII, VIII, IX, X, XI, or XII of Compound 1 to thereby treat the disorder in a subject in need thereof. The present disclosure provides a method of treating a disorder comprising administering an effective amount of a mixture of two or more of Forms I, II, III, V, VI, VII, VIII, IX, X, XI, or XII of Compound 1 to thereby treat the disorder in a subject in need thereof. In some embodiments, the disorder is a hormone-dependent condition.

The present disclosure provides a method of treating a disorder comprising administering an effective amount of one or more pharmaceutical compositions of the present disclosure to thereby treat the disorder in a subject in need thereof. In some embodiments, the present disclosure provides a method of treating a disorder comprising administering an effective amount of one or more pharmaceutical compositions comprising one or more crystalline forms disclosed herein to thereby treat the disorder in a subject in need thereof. In some embodiments, the present disclosure provides a method of treating a disorder comprising administering an effective amount of one or more pharmaceutical compositions comprising Form II of Compound 1 to thereby treat the disorder in a subject in need thereof. In some embodiments, the present disclosure provides a method of treating a disorder comprising administering an effective amount of one or more pharmaceutical compositions comprising Form III of Compound 1 to thereby treat the disorder in a subject in need thereof. In some embodiments, the present disclosure provides a method of treating a disorder comprising administering an effective amount of one or more pharmaceutical compositions comprising Form V of Compound 1 to thereby treat the disorder in a subject in need thereof. In some embodiments, the present disclosure provides a method of treating a disorder comprising administering an effective amount of one or more pharmaceutical compositions comprising Form VI of Compound 1 to thereby treat the disorder in a subject in need thereof. In some embodiments, the present disclosure provides a method of treating a disorder comprising administering an effective amount of one or more pharmaceutical compositions comprising Form VII of Compound 1 to thereby treat the disorder in a subject in need thereof. In some embodiments, the present disclosure provides a method of treating a disorder comprising administering an effective amount of one or more pharmaceutical compositions comprising Form VIII of Compound 1 to thereby treat the disorder in a subject in need thereof. In some embodiments, the present disclosure provides a method of treating a disorder comprising administering an effective amount of one or more pharmaceutical compositions comprising Form IX of Compound 1 to thereby treat the disorder in a subject in need thereof. In some embodiments, the present disclosure provides a method of treating a disorder comprising administering an effective amount of one or more pharmaceutical compositions comprising Form X of Compound 1 to thereby treat the disorder in a subject in need thereof. In some embodiments, the present disclosure provides a method of treating a disorder comprising administering an effective amount of one or more pharmaceutical compositions comprising Form XI of Compound 1 to thereby treat the disorder in a subject in need thereof. In some embodiments, the present disclosure provides a method of treating a disorder comprising administering an effective amount of one or more pharmaceutical compositions comprising Form XII of Compound 1 to thereby treat the disorder in a subject in need thereof. In some embodiments, the present disclosure provides a method of treating a disorder comprising administering an effective amount of one or more pharmaceutical compositions comprising a mixture of two or more of Forms II, III, V, VI, VII, VIII, IX, X, XI, or XII of Compound 1 to thereby treat the disorder in a subject in need thereof. In some embodiments, the present disclosure provides a method of treating a disorder comprising administering an effective amount of one or more pharmaceutical compositions comprising a mixture of two or more of Forms I, II, III, V, VI, VII, VIII, IX, X, XI, or XII of Compound 1 to thereby treat the disorder in a subject in need thereof. In some embodiments, the disorder is a hormone-dependent condition.

The present disclosure provides one or more crystalline forms of the present disclosure or one or more pharmaceutical compositions of the present disclosure for use in treating a disorder in a subject in need thereof. In some embodiments, the one or more crystalline forms comprise Form II of Compound 1. In some embodiments, the one or more crystalline forms comprise Form III of Compound 1. In some embodiments, the one or more crystalline forms comprise Form V of Compound 1. In some embodiments, the one or more crystalline forms comprise Form VI of Compound 1. In some embodiments, the one or more crystalline forms comprise Form VII of Compound 1. In some embodiments, the one or more crystalline forms comprise Form VIII of Compound 1. In some embodiments, the one or more crystalline forms comprise Form IX of Compound 1. In some embodiments, the one or more crystalline forms comprise Form X of Compound 1. In some embodiments, the one or more crystalline forms comprise Form XI of Compound 1. In some embodiments, the one or more crystalline forms comprise Form XII of Compound 1. In some embodiments, the one or more crystalline forms are a mixture of two or more of Forms II, III, V, VI, VII, VIII, IX, X, XI, or XII of Compound 1. In some embodiments, the one or more crystalline forms are a mixture of two or more of Forms I, II, III, V, VI, VII, VIII, IX, X, XI, or XII of Compound 1. In some embodiments, the one or more pharmaceutical compositions of the present disclosure comprise one or more crystalline forms disclosed herein. In some embodiments, the one or more pharmaceutical compositions of the present disclosure comprise Form II of Compound 1. In some embodiments, the one or more pharmaceutical compositions of the present disclosure comprise Form III of Compound 1. In some embodiments, the one or more pharmaceutical compositions of the present disclosure comprise Form V of Compound 1. In some embodiments, the one or more pharmaceutical compositions of the present disclosure comprise Form VI of Compound 1. In some embodiments, the one or more pharmaceutical compositions of the present disclosure comprise Form VII of Compound 1. In some embodiments, the one or more pharmaceutical compositions of the present disclosure comprise Form VIII of Compound 1. In some embodiments, the one or more pharmaceutical compositions of the present disclosure comprise Form IX of Compound 1. In some embodiments, the one or more pharmaceutical compositions of the present disclosure comprise Form X of Compound 1. In some embodiments, the one or more pharmaceutical compositions of the present disclosure comprise Form XI of Compound 1. In some embodiments, the one or more pharmaceutical compositions of the present disclosure comprise Form XII of Compound 1. In some embodiments, the one or more pharmaceutical compositions of the present disclosure comprise a mixture of two or more of Forms II, III, V, VI, VII, VIII, IX, X, XI, or XII of Compound 1. In some embodiments, the one or more pharmaceutical compositions of the present disclosure comprise a mixture of two or more of Forms I, II, III, V, VI, VII, VIII, IX, X, XI, or XII of Compound 1. In some embodiments, the disorder is a hormone-dependent condition.

The present disclosure provides for use of one or more crystalline forms of the present disclosure for treating a disorder in a subject in need thereof. In some embodiments, the present disclosure provides for use of Form II of Compound 1 for treating a disorder in a subject in need thereof. In some embodiments, the present disclosure provides for use of Form III of Compound 1 for treating a disorder in a subject in need thereof. In some embodiments, the present disclosure provides for use of Form V of Compound 1 for treating a disorder in a subject in need thereof. In some embodiments, the present disclosure provides for use of Form VI of Compound 1 for treating a disorder in a subject in need thereof. In some embodiments, the present disclosure provides for use of Form VII of Compound 1 for treating a disorder in a subject in need thereof. In some embodiments, the present disclosure provides for use of Form VIII of Compound 1 for treating a disorder in a subject in need thereof. In some embodiments, the present disclosure provides for use of Form IX of Compound 1 for treating a disorder in a subject in need thereof. In some embodiments, the present disclosure provides for use of Form X of Compound 1 for treating a disorder in a subject in need thereof. In some embodiments, the present disclosure provides for use of Form XI of Compound 1 for treating a disorder in a subject in need thereof. In some embodiments, the present disclosure provides for use of Form XII of Compound 1 for treating a disorder in a subject in need thereof. In some embodiments, the present disclosure provides for use of a mixture of two or more of Forms II, III, V, VI, VII, VIII, IX, X, XI, or XII of Compound 1 for treating a disorder in a subject in need thereof. In some embodiments, the disorder is a hormone-dependent condition. In some embodiments, the present disclosure provides for use of a mixture of two or more of Forms I, II, III, V, VI, VII, VIII, IX, X, XI, or XII of Compound 1 for treating a disorder in a subject in need thereof. In some embodiments, the disorder is a hormone-dependent condition.

The present disclosure provides for use of one or more pharmaceutical compositions of the present disclosure for treating a disorder in a subject in need thereof. In some embodiments, the present disclosure provides for use of one or more pharmaceutical compositions comprising one or more crystalline forms disclosed herein for treating a disorder in a subject in need thereof. In some embodiments, the present disclosure provides for use of one or more pharmaceutical compositions comprising Form II of Compound 1 for treating a disorder in a subject in need thereof. In some embodiments, the present disclosure provides for use of one or more pharmaceutical compositions comprising Form III of Compound 1 for treating a disorder in a subject in need thereof. In some embodiments, the present disclosure provides for use of one or more pharmaceutical compositions comprising Form V of Compound 1 for treating a disorder in a subject in need thereof. In some embodiments, the present disclosure provides for use of one or more pharmaceutical compositions comprising Form VI of Compound 1 for treating a disorder in a subject in need thereof. In some embodiments, the present disclosure provides for use of one or more pharmaceutical compositions comprising Form VII of Compound 1 for treating a disorder in a subject in need thereof. In some embodiments, the present disclosure provides for use of one or more pharmaceutical compositions comprising Form VIII of Compound 1 for treating a disorder in a subject in need thereof. In some embodiments, the present disclosure provides for use of one or more pharmaceutical compositions comprising Form IX of Compound 1 for treating a disorder in a subject in need thereof. In some embodiments, the present disclosure provides for use of one or more pharmaceutical compositions comprising Form X of Compound 1 for treating a disorder in a subject in need thereof. In some embodiments, the present disclosure provides for use of one or more pharmaceutical compositions comprising Form XI of Compound 1 for treating a disorder in a subject in need thereof. In some embodiments, the present disclosure provides for use of one or more pharmaceutical compositions comprising Form XII of Compound 1 for treating a disorder in a subject in need thereof. In some embodiments, the present disclosure provides for use of one or more pharmaceutical compositions comprising a mixture of two or more of Forms II, III, V, VI, VII, VIII, IX, X, XI, or XII of Compound 1 for treating a disorder in a subject in need thereof. In some embodiments, the present disclosure provides for use of one or more pharmaceutical compositions comprising a mixture of two or more of Forms I, II, III, V, VI, VII, VIII, IX, X, XI, or XII of Compound 1 for treating a disorder in a subject in need thereof. In some embodiments, the disorder is a hormone-dependent condition.

The present disclosure provides for use of one or more crystalline forms of the present disclosure in the manufacture of a medicament for treating a disorder. In some embodiments, the present disclosure provides for use of Form II of Compound 1 in the manufacture of a medicament for treating a disorder. In some embodiments, the present disclosure provides for use of Form III of Compound 1 in the manufacture of a medicament for treating a disorder. In some embodiments, the present disclosure provides for use of Form V of Compound 1 in the manufacture of a medicament for treating a disorder. In some embodiments, the present disclosure provides for use of Form VI of Compound 1 in the manufacture of a medicament for treating a disorder. In some embodiments, the present disclosure provides for use of Form VII of Compound 1 in the manufacture of a medicament for treating a disorder. In some embodiments, the present disclosure provides for use of Form VIII of Compound 1 in the manufacture of a medicament for treating a disorder. In some embodiments, the present disclosure provides for use of Form IX of Compound 1 in the manufacture of a medicament for treating a disorder. In some embodiments, the present disclosure provides for use of Form X of Compound 1 in the manufacture of a medicament for treating a disorder. In some embodiments, the present disclosure provides for use of Form XI of Compound 1 in the manufacture of a medicament for treating a disorder. In some embodiments, the present disclosure provides for use of Form XII of Compound 1 in the manufacture of a medicament for treating a disorder. In some embodiments, the present disclosure provides for use of a mixture of two or more of Forms II, III, V, VI, VII, VIII, IX, X, XI, or XII of Compound 1 in the manufacture of a medicament for treating a disorder. In some embodiments, the present disclosure provides for use of a mixture of two or more of Forms I, II, III, V, VI, VII, VIII, IX, X, XI, or XII of Compound 1 in the manufacture of a medicament for treating a disorder. In some embodiments, the disorder is a hormone-dependent condition.

The present disclosure provides for use of one or more pharmaceutical compositions of the present disclosure in the manufacture of a medicament for treating a disorder. In some embodiments, the present disclosure provides for use of one or more pharmaceutical compositions comprising one or more crystalline forms disclosed herein in the manufacture of a medicament for treating a disorder. In some embodiments, the present disclosure provides for use of one or more pharmaceutical compositions comprising Form II of Compound 1 in the manufacture of a medicament for treating a disorder. In some embodiments, the present disclosure provides for use of one or more pharmaceutical compositions comprising Form III of Compound 1 in the manufacture of a medicament for treating a disorder. In some embodiments, the present disclosure provides for use of one or more pharmaceutical compositions comprising Form V of Compound 1 in the manufacture of a medicament for treating a disorder. In some embodiments, the present disclosure provides for use of one or more pharmaceutical compositions comprising Form VI of Compound 1 in the manufacture of a medicament for treating a disorder. In some embodiments, the present disclosure provides for use of one or more pharmaceutical compositions comprising Form VII of Compound 1 in the manufacture of a medicament for treating a disorder. In some embodiments, the present disclosure provides for use of one or more pharmaceutical compositions comprising Form VIII of Compound 1 in the manufacture of a medicament for treating a disorder. In some embodiments, the present disclosure provides for use of one or more pharmaceutical compositions comprising Form IX of Compound 1 in the manufacture of a medicament for treating a disorder. In some embodiments, the present disclosure provides for use of one or more pharmaceutical compositions comprising Form X of Compound 1 in the manufacture of a medicament for treating a disorder. In some embodiments, the present disclosure provides for use of one or more pharmaceutical compositions comprising Form XI of Compound 1 in the manufacture of a medicament for treating a disorder. In some embodiments, the present disclosure provides for use of one or more pharmaceutical compositions comprising Form XII of Compound 1 in the manufacture of a medicament for treating a disorder. In some embodiments, the present disclosure provides for use of one or more pharmaceutical compositions comprising a mixture of two or more of Forms II, III, V, VI, VII, VIII, IX, X, XI, or XII of Compound 1 in the manufacture of a medicament for treating a disorder. In some embodiments, the present disclosure provides for use of one or more pharmaceutical compositions comprising a mixture of two or more of Forms I, II, III, V, VI, VII, VIII, IX, X, XI, or XII of Compound 1 in the manufacture of a medicament for treating a disorder. In some embodiments, the disorder is a hormone-dependent condition.

The present disclosure provides for use of one or more crystalline forms of the present disclosure as a medicament for treating a disorder. In some embodiments, the present disclosure provides for use of Form II of Compound 1 as a medicament for treating a disorder. In some embodiments, the present disclosure provides for use of Form III of Compound 1 as a medicament for treating a disorder. In some embodiments, the present disclosure provides for use of Form V of Compound 1 as a medicament for treating a disorder. In some embodiments, the present disclosure provides for use of Form VI of Compound 1 as a medicament for treating a disorder. In some embodiments, the present disclosure provides for use of Form VII of Compound 1 as a medicament for treating a disorder. In some embodiments, the present disclosure provides for use of Form VIII of Compound 1 as a medicament for treating a disorder. In some embodiments, the present disclosure provides for use of Form IX of Compound 1 as a medicament for treating a disorder. In some embodiments, the present disclosure provides for use of Form X of Compound 1 as a medicament for treating a disorder. In some embodiments, the present disclosure provides for use of Form XI of Compound 1 as a medicament for treating a disorder. In some embodiments, the present disclosure provides for use of Form XII of Compound 1 as a medicament for treating a disorder. In some embodiments, the present disclosure provides for use of a mixture of two or more of Forms II, III, V, VI, VII, VIII, IX, X, XI, or XII of Compound 1 as a medicament for treating a disorder. In some embodiments, the present disclosure provides for use of a mixture of two or more of Forms I, II, III, V, VI, VII, VIII, IX, X, XI, or XII of Compound 1 as a medicament for treating a disorder. In some embodiments, the disorder is a hormone-dependent condition.

The present disclosure provides for use of one or more pharmaceutical compositions of the present disclosure as a medicament for treating a disorder. In some embodiments, the present disclosure provides for use of one or more pharmaceutical compositions comprising one or more crystalline forms disclosed herein as a medicament for treating a disorder. In some embodiments, the present disclosure provides for use of one or more pharmaceutical compositions comprising Form II of Compound 1 as a medicament for treating a disorder. In some embodiments, the present disclosure provides for use of one or more pharmaceutical compositions comprising Form III of Compound 1 as a medicament for treating a disorder. In some embodiments, the present disclosure provides for use of one or more pharmaceutical compositions comprising Form V of Compound 1 as a medicament for treating a disorder. In some embodiments, the present disclosure provides for use of one or more pharmaceutical compositions comprising Form VI of Compound 1 as a medicament for treating a disorder. In some embodiments, the present disclosure provides for use of one or more pharmaceutical compositions comprising Form VII of Compound 1 as a medicament for treating a disorder. In some embodiments, the present disclosure provides for use of one or more pharmaceutical compositions comprising Form VIII of Compound 1 as a medicament for treating a disorder. In some embodiments, the present disclosure provides for use of one or more pharmaceutical compositions comprising Form IX of Compound 1 as a medicament for treating a disorder. In some embodiments, the present disclosure provides for use of one or more pharmaceutical compositions comprising Form X of Compound 1 as a medicament for treating a disorder. In some embodiments, the present disclosure provides for use of one or more pharmaceutical compositions comprising Form XI of Compound 1 as a medicament for treating a disorder. In some embodiments, the present disclosure provides for use of one or more pharmaceutical compositions comprising Form XII of Compound 1 as a medicament for treating a disorder. In some embodiments, the present disclosure provides for use of one or more pharmaceutical compositions comprising a mixture of two or more of Forms II, III, V, VI, VII, VIII, IX, X, XI, or XII of Compound 1 as a medicament for treating a disorder. In some embodiments, the present disclosure provides for use of one or more pharmaceutical compositions comprising a mixture of two or more of Forms I, II, III, V, VI, VII, VIII, IX, X, XI, or XII of Compound 1 as a medicament for treating a disorder. In some embodiments, the disorder is a hormone-dependent condition.

In some embodiments of the methods and uses of the disclosure, only one pharmaceutical composition of the disclosure is used in the methods or uses. In some embodiments of the methods and uses of the disclosure, only one crystalline form of the disclosure is used in the methods or uses.

For the therapeutic uses mentioned herein, the dosage administered will, of course, vary with the one or more crystalline forms or pharmaceutical compositions employed, the mode of administration, the treatment desired and the disorder indicated. For example, the daily dosage of the one or more crystalline forms of the present disclosure, if inhaled, may be in the range from about 0.05 micrograms per kilogram body weight (μg/kg) to about 100 micrograms per kilogram body weight (μg/kg). Alternatively, if the one or more crystalline forms or pharmaceutical compositions is administered orally, then the daily dosage of the one or more crystalline forms of the present disclosure may be in the range from about 0.01 micrograms per kilogram body weight (μg/kg) to about 100 milligrams per kilogram body weight (mg/kg).

It will be understood, however, that the total daily usage of the one or more crystalline forms or pharmaceutical compositions of the present disclosure will be decided by the attending physician within the scope of sound medical judgment. The specific therapeutically effective dose level for any particular patient will depend upon a variety of factors including the disorder being treated and the severity of the disorder; the activity of the specific crystalline form employed; the specific pharmaceutical composition employed; the age, body weight, general health, sex and diet of the patient; the time of administration, route of administration, and rate of excretion of the specific crystalline form employed; the duration of the treatment; drugs used in combination or coincidental with the specific crystalline form employed; and like factors well known in the medical arts. A physician or veterinarian of ordinary skill in the art can readily determine and prescribe the therapeutically effective amount of the one or more crystalline forms or pharmaceutical compositions disclosed herein required to treat, counter, or arrest the progress of the disorder.

Combination Therapy

In some embodiments, one or more crystalline forms or pharmaceutical compositions described herein may be used alone or together or conjointly administered, or used in combination, with one or more other therapeutic agents or pharmaceutical compositions. Conjoint administration or used in combination may refer to any form of administration of two or more different compounds, crystalline forms, or pharmaceutical compositions such that the second compound, crystalline form, or pharmaceutical composition is administered while the previously administered compound, crystalline form, or pharmaceutical composition is still effective in the body. For example, the different compounds, crystalline forms, or pharmaceutical compositions can be administered either in the same formulation or in a separate formulation, either simultaneously, sequentially, or by separate dosing of the individual components of the treatment. In some embodiments, the different compounds, crystalline forms, or pharmaceutical compositions can be administered within about one hour, about 12 hours, about 24 hours, about 36 hours, about 48 hours, about 72 hours, or about a week of one another. Thus, an individual who receives such treatment can benefit from a combined effect of different compounds, crystalline forms, or pharmaceutical compositions.

In some embodiments, one or more of the crystalline forms or pharmaceutical compositions of the disclosure are used in combination with one or more other crystalline forms or pharmaceutical compositions of the disclosure in the methods or uses of the disclosure. In certain such embodiments, the combination of one or more other crystalline forms or pharmaceutical compositions of the disclosure is used in a method for treating one or more of the disorders listed herein.

In some embodiments, one or more of the crystalline forms or pharmaceutical compositions of the disclosure are used in combination with estradiol or a corresponding amount of estradiol equivalent. In some embodiments, one or more of the crystalline forms or pharmaceutical compositions of the disclosure are used in combination with a progestin. In some embodiments, one or more of the crystalline forms or pharmaceutical compositions of the disclosure are used in combination with estradiol or a corresponding amount of estradiol equivalent and a progestin. In some embodiments, the progestin is norethindrone acetate.

In some embodiments, combinations of one or more crystalline forms or pharmaceutical compositions provided herein, or combinations of other known agents or pharmaceutical compositions and one or more crystalline forms or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more crystalline forms or pharmaceutical compositions of the disclosure are administered at a sub-therapeutic dose, wherein a subtherapeutic dose is a dose that would be insufficient to treat one of the disorders listed herein if administered alone.

Kits

In some embodiments, this disclosure also provides a pharmaceutical package or kit comprising one or more containers filled with at least one crystalline form or pharmaceutical composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The foregoing applies to any of the crystalline forms, pharmaceutical compositions, methods, and uses described herein. This disclosure specifically contemplates any combination of the features of such crystalline forms, pharmaceutical compositions, methods, and uses (alone or in combination) with the features described for the various kits described in this section.

Although methods and materials similar or equivalent to those described herein can be used in the practice or testing of the present disclosure, illustrative methods and materials are described herein. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

ENUMERATED EMBODIMENTS

Some embodiments of the disclosure include those of Embodiment I:

Embodiment I-1. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form II of Compound 1.

Embodiment I-2. The crystalline form of Embodiment I-1, characterized by an X-ray power diffraction pattern comprising at least three peaks selected from the group consisting of 9.7°, 10.7°, 19.0°, 19.3° and 20.9° 2θ±0.2° 2θ.

Embodiment I-3. The crystalline form of Embodiment I-1, characterized by an X-ray power diffraction pattern comprising at least five peaks selected from the group consisting of 7.2°, 9.7°, 10.7°, 13.1°, 15.7°, 19.0°, 19.3° and 20.9° 2θ±0.2° 2θ.

Embodiment I-4. The crystalline form of Embodiment I-1, characterized by an X-ray power diffraction pattern comprising peaks at 9.7°, 10.7°, 19.0°, 19.3° and 20.9° 2θ±0.2° 2θ.

Embodiment I-5. The crystalline form of Embodiment I-4, wherein the X-ray power diffraction pattern comprises one or more peaks selected from the group consisting of 7.2°, 13.1° and 15.7°±0.2° 2θ.

Embodiment I-6. The crystalline form of any one of Embodiments I-1 to I-5, characterized by an XRPD pattern substantially the same as the pattern shown in FIG. 1.

Embodiment I-7. The crystalline form of any one of Embodiments I-1 to I-6, characterized by an onset of degradation between about 174° C. and about 176° C.

Embodiment I-8. The crystalline form of any one of Embodiments I-1 to I-7, characterized by an onset of degradation at about 175° C.

Embodiment I-9. The crystalline form of any one of Embodiments I-1 to I-8, characterized by a thermogravimetry (TG) thermogram substantially the same as the pattern shown in FIG. 2.

Embodiment I-10. The crystalline form of any one of Embodiments I-1 to I-9, characterized by an onset of melting between about 179° C. and about 181° C.

Embodiment I-11. The crystalline form of any one of Embodiments I-1 to I-10, characterized by an onset of melting at about 180° C.

Embodiment I-12. The crystalline form of any one of Embodiments I-1 to I-11, characterized by a differential scanning calorimetry (DSC) thermogram comprising an exothermic peak between about 191° C. and about 194° C.

Embodiment I-13. The crystalline form of any one of Embodiments I-1 to I-12, characterized by a DSC thermogram comprising an exothermic peak at about 192° C.

Embodiment I-14. The crystalline form of any one of Embodiments I-1 to I-13, characterized by a DSC thermogram substantially the same as the pattern shown in FIG. 3.

Embodiment I-15. The crystalline form of Embodiment I-1, characterized by having at least two of the following:
a) an XRPD pattern comprising at least three peaks selected from the group consisting of 9.7°, 10.7°, 19.0°, 19.3° and 20.9° 2θ±0.2° 2θ;
b) an onset of degradation at about 175° C. as measured by TG; and
c) an exothermic peak at about 192° C. as measured by DSC.

Embodiment I-16. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form III of Compound 1.

Embodiment I-17. The crystalline form of Embodiment I-16, characterized by an X-ray power diffraction pattern comprising at least three peaks selected from the group consisting of 7.5°, 9.5°, 16.8°, and 18.1° 2θ±0.2° 2θ.

Embodiment I-18. The crystalline form of Embodiment I-16, characterized by an X-ray power diffraction pattern comprising at least five peaks selected from the group consisting of 7.5°, 9.5°, 12.2°, 16.6°, 16.8°, and 18.1° 2θ±0.2° 2θ.

Embodiment I-19. The crystalline form of Embodiment I-16, characterized by an X-ray power diffraction pattern comprising peaks at 7.5°, 9.5°, 16.8°, and 18.1° 2θ±0.2° 2θ.

Embodiment I-20. The crystalline form of Embodiment I-19, wherein the X-ray power diffraction pattern comprises one or more peaks selected from the group consisting of 12.2° and 16.6°±0.2° 2θ.

Embodiment I-21. The crystalline form of any one of Embodiments I-16 to I-20, characterized by an XRPD pattern substantially the same as the pattern shown in FIG. 4.

Embodiment I-22. The crystalline form of any one of Embodiments I-16 to I-21, characterized by an onset of dehydration at about 43° C. and continued dehydration to about 78° C.

Embodiment I-23. The crystalline form of any one of Embodiments I-16 to I-22, characterized by an onset of degradation at about 183° C.

Embodiment I-24. The crystalline form of any one of Embodiments I-16 to I-23, characterized by a TG thermogram substantially the same as the pattern shown in FIG. 5.

Embodiment I-25. The crystalline form of any one of Embodiments I-16 to I-24, characterized by a differential scanning calorimetry (DSC) thermogram comprising an endothermic peak at about 79° C.

Embodiment I-26. The crystalline form of any one of Embodiments I-16 to I-25, characterized by a DSC thermogram comprising an exothermic peak at about 205° C.

Embodiment I-27. The crystalline form of any one of Embodiments I-16 to I-26, characterized by a DSC thermogram substantially the same as the pattern shown in FIG. 6.

Embodiment I-28. The crystalline form of Embodiment I-16, characterized by having at least two of the following:
a. an XRPD pattern comprising at least three peaks selected from the group consisting of 7.5°, 9.5°, 16.8°, and 18.1° 2θ±0.2° 2θ;
b. an onset of dehydration at about 43° C. as measured by TG; and
c. an endothermic peak at about 79° C. as measured by DSC.

Embodiment I-29. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form V of Compound 1.

Embodiment I-30. The crystalline form of Embodiment I-29, characterized by an X-ray power diffraction pattern comprising at least three peaks selected from the group consisting of 7.1°, 10.6°, 11.2°, 15.3° and 16.7° 2θ±0.2° 2θ.

Embodiment I-31. The crystalline form of Embodiment I-29 or I-30, characterized by an XRPD pattern substantially the same as the pattern shown in FIG. 7.

Embodiment I-32. The crystalline form of any one of Embodiments I-29 to I-31, characterized by a TG thermogram substantially the same as the pattern shown in FIG. 8.

Embodiment I-33. The crystalline form of any one of Embodiments I-29 to I-32, characterized by a DSC thermogram substantially the same as the pattern shown in FIG. 9.

Embodiment I-34. The crystalline form of Embodiment I-29, characterized by having at least two of the following:
a. an XRPD pattern comprising at least three peaks selected from the group consisting of 7.1°, 10.6°, 11.2°, 15.3° and 16.7° 2θ±0.2° 2θ;
b. a TG thermogram substantially the same as the pattern shown in FIG. 8; and
c. a DSC thermogram substantially the same as the pattern shown in FIG. 9.

Embodiment I-35. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form VI of Compound 1.

Embodiment I-36. The crystalline form of Embodiment I-35, characterized by an X-ray power diffraction pattern comprising at least three peaks selected from the group consisting of 7.2°, 10.5°, 11.1°, 15.2° and 16.6° 2θ±0.2° 2θ.

Embodiment I-37. The crystalline form of Embodiment I-35 or I-36, characterized by an XRPD pattern substantially the same as the pattern shown in FIG. 10.

Embodiment I-38. The crystalline form of any one of Embodiments I-35 to I-37, characterized by a TG thermogram substantially the same as the pattern shown in FIG. 11.

Embodiment I-39. The crystalline form of any one of Embodiments I-35 to I-38, characterized by a DSC thermogram substantially the same as the pattern shown in FIG. 12.

Embodiment I-40. The crystalline form of Embodiment I-35, characterized by having at least two of the following:
a. an XRPD pattern comprising at least three peaks selected from the group consisting of 7.2°, 10.5°, 11.1°, 15.2° and 16.6° 2θ±0.2° 2θ;
b. a TG thermogram substantially the same as the pattern shown in FIG. 11; and
c. a DSC thermogram substantially the same as the pattern shown in FIG. 12.

Embodiment I-41. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form VII of Compound 1.

Embodiment I-42. The crystalline form of Embodiment I-41, characterized by an X-ray power diffraction pattern comprising at least three peaks selected from the group consisting of 8.4°, 10.6°, 13.6°, 15.4° and 18.8° 2θ±0.2° 2θ.

Embodiment I-43. The crystalline form of Embodiment I-41 or I-42, characterized by an XRPD pattern substantially the same as the pattern shown in FIG. 13.

Embodiment I-44. The crystalline form of any one of Embodiments I-41 to I-43, characterized by a TG thermogram substantially the same as the pattern shown in FIG. 14.

Embodiment I-45. The crystalline form of any one of Embodiments I-41 to I-44, characterized by a DSC thermogram substantially the same as the pattern shown in FIG. 15.

Embodiment I-46. The crystalline form of Embodiment I-41, characterized by having at least two of the following:
a. an XRPD pattern comprising at least three peaks selected from the group consisting of 8.4°, 10.6°, 13.6°, 15.4° and 18.8° 2θ±0.2° 2θ;
b. a TG thermogram substantially the same as the pattern shown in FIG. 14; and
c. a DSC thermogram substantially the same as the pattern shown in FIG. 15.

Embodiment I-47. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form VIII of Compound 1.

Embodiment I-48. The crystalline form of Embodiment I-47, characterized by an X-ray power diffraction pattern comprising at least three peaks selected from the group consisting of 7.4°, 10.6°, 13.7°, 15.2°, and 18.7° 2θ±0.2° 2θ.

Embodiment I-49. The crystalline form of Embodiment I-47 or I-48, characterized by an XRPD pattern substantially the same as the pattern shown in FIG. 16.

Embodiment I-50. The crystalline form of any one of Embodiments I-47 to I-49, characterized by a TG thermogram substantially the same as the pattern shown in FIG. 17.

Embodiment I-51. The crystalline form of any one of Embodiments I-47 to I-50, characterized by a DSC thermogram substantially the same as the pattern shown in FIG. 18.

Embodiment I-52. The crystalline form of Embodiment I-47, characterized by having at least two of the following:
a. an XRPD pattern comprising at least three peaks selected from the group consisting of 7.4°, 10.6°, 13.7°, 15.2°, and 18.7° 2θ±0.2° 2θ;
b. a TG thermogram substantially the same as the pattern shown in FIG. 17; and
c. a DSC thermogram substantially the same as the pattern shown in FIG. 18.

Embodiment I-53. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form IX of Compound 1.

Embodiment I-54. The crystalline form of Embodiment I-53, characterized by an XRPD pattern substantially the same as the pattern shown in FIG. 19.

Embodiment I-55. The crystalline form of Embodiment I-53 or I-54, characterized by a TG thermogram substantially the same as the pattern shown in FIG. 20.

Embodiment I-56. The crystalline form of any one of Embodiments I-53 to I-55, characterized by a DSC thermogram substantially the same as the pattern shown in FIG. 21.

Embodiment I-57. The crystalline form of Embodiment I-53, characterized by having at least two of the following:
a. an XRPD pattern substantially the same as the pattern shown in FIG. 19;
b. a TG thermogram substantially the same as the pattern shown in FIG. 20; and
c. a DSC thermogram substantially the same as the pattern shown in FIG. 21.

Embodiment I-58. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form X of Compound 1.

Embodiment I-59. The crystalline form of Embodiment I-58, characterized by an X-ray power diffraction pattern comprising at least three peaks selected from the group consisting of 4.6°, 9.1°, 9.6°, 17.4°, and 18.8° 2θ±0.2° 2θ.

Embodiment I-60. The crystalline form of Embodiment I-58 or I-59, characterized by an XRPD pattern substantially the same as the pattern shown in FIG. 22.

Embodiment I-61. The crystalline form of any one of Embodiments I-58 to I-60, characterized by a TG thermogram substantially the same as the pattern shown in FIG. 23.

Embodiment I-62. The crystalline form of any one of Embodiments I-58 to I-61, characterized by a DSC thermogram substantially the same as the pattern shown in FIG. 24.

Embodiment I-63. The crystalline form of Embodiment I-58, characterized by having at least two of the following:
a. an XRPD pattern comprising at least three peaks selected from the group consisting of 4.6°, 9.1°, 9.6°, 17.4°, and 18.8° 2θ±0.2° 2θ;
b. a TG thermogram substantially the same as the pattern shown in FIG. 23; and
c. a DSC thermogram substantially the same as the pattern shown in FIG. 24.

Embodiment I-64. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XI of Compound 1.

Embodiment I-65. The crystalline form of Embodiment I-64, characterized by an XRPD pattern substantially the same as the pattern shown in FIG. 30.

Embodiment I-66. The crystalline form of Embodiment I-64 or I-65, characterized by a TG thermogram substantially the same as the pattern shown in FIG. 31, top panel.

Embodiment I-67. The crystalline form of any one of Embodiments I-64 to I-66, characterized by a DSC thermogram substantially the same as the pattern shown in FIG. 31, bottom panel.

Embodiment I-68. The crystalline form of Embodiment I-64, characterized by having at least two of the following:
a) an XRPD pattern substantially the same as the pattern shown in FIG. 30;
b) a TG thermogram substantially the same as the pattern shown in FIG. 31, top panel; and
c) a DSC thermogram substantially the same as the pattern shown in FIG. 31, bottom panel.

Embodiment I-69. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XII of Compound 1.

Embodiment I-70. The crystalline form of Embodiment I-69, characterized by an XRPD pattern substantially the same as the pattern shown in FIG. 32.

Embodiment I-71. The crystalline form of Embodiment I-69 or I-70, characterized by a TG thermogram substantially the same as the pattern shown in FIG. 33, top panel.

Embodiment I-72. The crystalline form of any one of Embodiments I-69 to I-71, characterized by a DSC thermogram substantially the same as the pattern shown in FIG. 33, bottom panel.

Embodiment I-73. The crystalline form of Embodiment I-69, characterized by having at least two of the following:
a) an XRPD pattern substantially the same as the pattern shown in FIG. 32;
b) a TG thermogram substantially the same as the pattern shown in FIG. 33, top panel; and
c) a DSC thermogram substantially the same as the pattern shown in FIG. 33, bottom panel.

Embodiment I-74. A pharmaceutical composition comprising one or more crystalline forms of any one of Embodiments I-1 to I-73 and a pharmaceutically acceptable carrier.

Embodiment I-75. The pharmaceutical composition of Embodiment I-74, the pharmaceutical composition comprising a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1.

Embodiment I-76. A method of treating a disorder in a subject in need thereof, comprising administering to the subject an effective amount of one or more crystalline forms of any one of Embodiments I-1 to I-73.

Embodiment I-77. The method of Embodiment I-76, the method comprising administering to the subject an effective amount of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1.

Embodiment I-78. A method of treating a disorder in a subject in need thereof, comprising administering to the subject an effective amount of the pharmaceutical composition of Embodiment I-74 or I-75.

Embodiment I-79. The method of any one of Embodiments I-76 to I-78, wherein the disorder is a hormone-dependent condition.

Embodiment I-80. The method of Embodiment I-79, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-81. The method of Embodiment I-79 or I-80, wherein the hormone-dependent condition is prostate cancer, uterine cancer, breast cancer, or ovarian cancer.

Embodiment I-82. The method of any one of Embodiments I-79 to I-81, wherein the hormone-dependent condition is prostate cancer.

Embodiment I-83. The method of any one of Embodiments I-79 to I-81, wherein the hormone-dependent condition is uterine cancer.

Embodiment I-84. The method of any one of Embodiments I-79 to I-81, wherein the hormone-dependent condition is breast cancer.

Embodiment I-85. The method of any one of Embodiments I-79 to I-81, wherein the hormone-dependent condition is ovarian cancer.

Embodiment I-86. The method of Embodiment I-79 or I-80, wherein the hormone-dependent condition is uterine fibroids.

Embodiment I-87. The method of Embodiment I-79, wherein the hormone-dependent condition is heavy menstrual bleeding associated with uterine fibroids.

Embodiment I-88. The method of Embodiment I-79, wherein the hormone-dependent condition is pain or other symptoms associated with uterine fibroids.

Embodiment I-89. The method of Embodiment I-79 or I-80, wherein the hormone-dependent condition is endometriosis.

Embodiment I-90. The method of Embodiment I-79 or I-80, wherein the hormone-dependent condition is adenomyosis.

Embodiment I-91. The method of Embodiment I-79 or I-80, wherein the hormone-dependent condition is heavy menstrual bleeding.

Embodiment I-92. The method of any one of Embodiments I-76 to I-91, the method comprising administering to the subject estradiol or a corresponding amount of estradiol equivalent.

Embodiment I-92. The method of any one of Embodiments I-76 to I-91, the method comprising administering to the subject a progestin.

Embodiment I-93. The method of any one of Embodiments I-76 to I-91, the method comprising administering to the subject estradiol, or a corresponding amount of estradiol equivalent, and a progestin.

Embodiment I-94. The method of Embodiment I-92 or I-93, wherein the progestin is norethindrone acetate.

Embodiment I-95. One or more crystalline forms of any one of Embodiments I-1 to I-73 for use in treating a disorder in a subject in need thereof.

Embodiment I-96. The one or more crystalline forms for use of Embodiment I-95, the one or more crystalline forms for use comprising a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 for use in treating the disorder in the subject in need thereof.

Embodiment I-97. The one or more crystalline forms for use of Embodiment I-95 or I-96, wherein the disorder is a hormone-dependent condition.

Embodiment I-98. The one or more crystalline forms for use of Embodiment I-97, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-99. The one or more crystalline forms for use of Embodiment I-97 or I-98, wherein the hormone-dependent condition is prostate cancer, uterine cancer, breast cancer, or ovarian cancer.

Embodiment I-100. The one or more crystalline forms for use of any one of Embodiments I-97 to I-99, wherein the hormone-dependent condition is prostate cancer.

Embodiment I-101. The one or more crystalline forms for use of any one of Embodiments I-97 to I-99, wherein the hormone-dependent condition is uterine cancer.

Embodiment I-102. The one or more crystalline forms for use of any one of Embodiments I-97 to I-99, wherein the hormone-dependent condition is breast cancer.

Embodiment I-103. The one or more crystalline forms for use of any one of Embodiments I-97 to I-99, wherein the hormone-dependent condition is ovarian cancer.

Embodiment I-104. The one or more crystalline forms for use of Embodiment I-97 or I-98, wherein the hormone-dependent condition is uterine fibroids.

Embodiment I-105. The one or more crystalline forms for use of Embodiment I-97, wherein the hormone-dependent condition is heavy menstrual bleeding associated with uterine fibroids.

Embodiment I-106. The one or more crystalline forms for use of Embodiment I-97, wherein the hormone-dependent condition is pain or other symptoms associated with uterine fibroids.

Embodiment I-107. The one or more crystalline forms for use of Embodiment I-97 or I-98, wherein the hormone-dependent condition is endometriosis.

Embodiment I-108. The one or more crystalline forms for use of Embodiment I-97 or I-98, wherein the hormone-dependent condition is adenomyosis.

Embodiment I-109. The one or more crystalline forms for use of Embodiment I-97 or I-98, wherein the hormone-dependent condition is heavy menstrual bleeding.

Embodiment I-110. The one or more crystalline forms for use of any one of Embodiments I-95 to I-109, wherein the one or more crystalline forms for use are used in combination with estradiol or a corresponding amount of estradiol equivalent.

Embodiment I-111. The one or more crystalline forms for use of any one of Embodiments I-95 to I-109, wherein the one or more crystalline forms for use are used in combination with progestin.

Embodiment I-112. The one or more crystalline forms for use of any one of Embodiments I-95 to I-109, wherein the one or more crystalline forms for use are used in combination with estradiol, or a corresponding amount of estradiol equivalent, and a progestin.

Embodiment I-113. The one or more crystalline forms for use of Embodiment I-111 or I-112, wherein the progestin is norethindrone acetate.

Embodiment I-114. A pharmaceutical composition of Embodiment I-74 or I-75 for use in treating a disorder in a subject in need thereof.

Embodiment I-115. The pharmaceutical composition for use of Embodiment I-114, wherein the disorder is a hormone-dependent condition.

Embodiment I-116. The pharmaceutical composition for use of Embodiment I-115, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-117. The pharmaceutical composition for use of Embodiment I-115 or I-116, wherein the hormone-dependent condition is prostate cancer, uterine cancer, breast cancer, or ovarian cancer.

Embodiment I-118. The pharmaceutical composition for use of any one of Embodiments I-115 to I-117, wherein the hormone-dependent condition is prostate cancer.

Embodiment I-119. The pharmaceutical composition for use of any one of Embodiments I-115 to I-117, wherein the hormone-dependent condition is uterine cancer.

Embodiment I-120. The pharmaceutical composition for use of any one of Embodiments I-115 to I-117, wherein the hormone-dependent condition is breast cancer.

Embodiment I-121. The pharmaceutical composition for use of any one of Embodiments I-115 to I-117, wherein the hormone-dependent condition is ovarian cancer.

Embodiment I-122. The pharmaceutical composition for use of Embodiment I-115 or I-116, wherein the hormone-dependent condition is uterine fibroids.

Embodiment I-123. The pharmaceutical composition for use of Embodiment I-115, wherein the hormone-dependent condition is heavy menstrual bleeding associated with uterine fibroids.

Embodiment I-124. The pharmaceutical composition for use of Embodiment I-115, wherein the hormone-dependent condition is pain or other symptoms associated with uterine fibroids.

Embodiment I-125. The pharmaceutical composition for use of Embodiment I-115 or I-116, wherein the hormone-dependent condition is endometriosis.

Embodiment I-126. The pharmaceutical composition for use of Embodiment I-115 or I-116, wherein the hormone-dependent condition is adenomyosis.

Embodiment I-127. The pharmaceutical composition for use of Embodiment I-115 or I-116, wherein the hormone-dependent condition is heavy menstrual bleeding.

Embodiment I-128. The pharmaceutical composition for use of any one of Embodiments I-114 to I-127, wherein the pharmaceutical composition for use is used in combination with estradiol or a corresponding amount of estradiol equivalent.

Embodiment I-129. The pharmaceutical composition for use of any one of Embodiments I-114 to I-127, wherein the pharmaceutical composition for use is used in combination with a progestin.

Embodiment I-130. The pharmaceutical composition for use of any one of Embodiments I-114 to I-127, wherein the pharmaceutical composition for use is used in combination with estradiol, or a corresponding amount of estradiol equivalent, and a progestin.

Embodiment I-131. The pharmaceutical composition for use of Embodiment I-129 or I-130, wherein the progestin is norethindrone acetate.

Embodiment I-132. Use of one or more crystalline forms of any one of Embodiments I-1 to I-73 for treating a disorder in a subject in need thereof.

Embodiment I-133. The use of Embodiment I-132, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 for treating the disorder in the subject in need thereof.

Embodiment I-134. Use of a pharmaceutical composition of Embodiment I-74 or I-75 for treating a disorder in a subject in need thereof.

Embodiment I-135. Use of one or more crystalline forms of any one of Embodiments I-1 to I-73 in the manufacture of a medicament for treating a disorder.

Embodiment I-136. The use of Embodiment I-135, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in the manufacture of the medicament for treating the disorder.

Embodiment I-137. Use of a pharmaceutical composition of Embodiment I-74 or I-75 in the manufacture of a medicament for treating a disorder.

Embodiment I-138. Use of one or more crystalline forms of any one of Embodiments I-1 to I-73 as a medicament for treating a disorder.

Embodiment I-139. The use of Embodiment I-138, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 as a medicament for treating the disorder.

Embodiment I-140. Use of a pharmaceutical composition of Embodiment I-74 or I-75 as a medicament for treating a disorder.

Embodiment I-141. The use of any one of Embodiments I-132 to I-140, wherein the disorder is a hormone-dependent condition.

Embodiment I-142. The use of Embodiment I-141, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-143. The use of Embodiment I-141 or I-142, wherein the hormone-dependent condition is prostate cancer, uterine cancer, breast cancer, or ovarian cancer.

Embodiment I-144. The use of any one of Embodiments I-141 to I-143, wherein the hormone-dependent condition is prostate cancer.

Embodiment I-145. The use of any one of Embodiments I-141 to I-143, wherein the hormone-dependent condition is uterine cancer.

Embodiment I-146. The use of any one of Embodiments I-141 to I-143, wherein the hormone-dependent condition is breast cancer.

Embodiment I-147. The use of any one of Embodiments I-141 to I-143, wherein the hormone-dependent condition is ovarian cancer.

Embodiment I-148. The use of Embodiment I-141 or I-142, wherein the hormone-dependent condition is uterine fibroids.

Embodiment I-149. The use of Embodiment I-141, wherein the hormone-dependent condition is heavy menstrual bleeding associated with uterine fibroids.

Embodiment I-150. The use of Embodiment I-141, wherein the hormone-dependent condition is pain or other symptoms associated with uterine fibroids.

Embodiment I-151. The use of Embodiment I-141 or I-142, wherein the hormone-dependent condition is endometriosis.

Embodiment I-152. The use of Embodiment I-141 or I-142, wherein the hormone-dependent condition is adenomyosis.

Embodiment I-153. The use of Embodiment I-141 or I-142, wherein the hormone-dependent condition is heavy menstrual bleeding.

Embodiment I-154. The use of any one of Embodiments I-132 to I-153, the use comprising use of estradiol or a corresponding amount of estradiol equivalent for treating the disorder.

Embodiment I-155. The use of any one of Embodiments I-132 to I-153, the use comprising use of a progestin for treating the disorder.

Embodiment I-156. The use of any one of Embodiments I-132 to I-153, the use comprising use of estradiol, or a corresponding amount of estradiol equivalent, and a progestin for treating the disorder.

Embodiment I-157. The use of Embodiment I-155 or I-156, wherein the progestin is norethindrone acetate.

Embodiment I-158. A method for preparing the crystalline form of any one of Embodiments I-1 to I-15, said method comprising:
a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in a mixture of DMF and acetone (about 6:94, v/v) at about 25° C. to form a solution;
b) stirring the solution at a temperature of about −15° C. to about −25° C. for about 3 days to generate a suspension; and
c) isolating solids from the suspension by vacuum filtration to afford the crystalline form of any one of Embodiments I-1 to I-15.

Embodiment I-159. The method of Embodiment I-158, the method comprising vacuum drying the isolated solids at about 60° C. for about 4 hours to afford the crystalline form of any one of Embodiments I-1 to I-15.

EXAMPLES

General Methods of the Examples

All solvents (HPLC or reagent grade) or reagents used in the Examples were supplied by Wako Pure Chemical Industries.

X-Ray Powder Diffraction (XRPD)

X-ray powder diffractograms were obtained using D8 DISCOVER (Bruker AXS Corporation) and Ultima IV 3 kW X-ray diffractometer (Rigaku Corporation). Samples were placed on a glass plate or silicon sample plate. The instrument parameters were as follows:

D8 DISCOVER: 40 kV/50 mA; Vantec 2-dimensional detector; detection angle range (2θ), 4-28° Ultima IV: Cu Kα source (λ=0.154 nm) radiation, 40 kV/50 mA; Scan speed (2θ); 6°/minute detection angle range (2θ), 2-35°.

Gas Chromatography (GC)

Solvent contents in the samples were measured using GC 2010 Plus (Shimadzu Corporation). Samples were dissolved in a vial with acetone. The analytical conditions and calculation formula of solvent contents were as follows:

| Analytical conditions | |
|---|---|
| System: | GC2010 Plus |
| Detector: | FID2010 Plus |
| Column: | OVI-G43, 0.53 mm i.d. × 30 m, 3 μm (SUPELCO, Inc.)/Stabiwax, 0.53 mm i.d. × 60 m, 1 μm (Restek Corporation) |
| Oven Temp. Program: | 40° C. (10 min) to 240° C. at 10° C./min/40° C. (1 min) to 250° C. at 10° C./min |
| Detector Temp.: | 250° C./240° C. |
| Injection Temp: | 160° C. |
| He flow: | 35 cm/sec |
| Split ratio: | 1:5 |
| Injection volume: | 1 μL |
| Solvent contents calculation formula: | $SS_{ssssssssssss} = \dfrac{CC_{ssssss}}{AA_{ssssss}} \times \dfrac{AA_{sssssssssss}}{CC_{sssssssssss}} \times 1000000$ |

S: solvent content (ppm), C: concentration, A: area, Std: standard

Karl Fischer (KF) Titration

Water content in samples was measured using a Hiranuma aquacounter AQ-7 (Hiranuma Corporation). Samples were dissolved in Aqualite RS-A and water content was measured by coulometric titration method.

Differential Scanning calorimeter (DSC)

A Differential Scanning calorimeter of Hitachi DSC7000X (Hitachi High-Tech Science Corporation) was used for all the studies. Samples were placed in aluminum DSC pans crimped, and heated from 25° C. to 300° C. at the rate of 5° C./min under an atmosphere of nitrogen flow at 30 mL/min. This method was used for DSC analysis of Form II of Compound 1, Form III of Compound 1, Form V of Compound 1, Form VI of Compound 1, Form VII of Compound 1, Form VIII of Compound 1, Form IX of Compound 1, and Form X of Compound 1.

Thermogravimetry (TG)

For the thermogravimetry studies, a Hitachi STA7200 (Hitachi High-Tech Science Corporation) was used to determine the percentage weight loss upon heating. Samples were placed in open aluminum pans and the furnace was heated from 25° C. to 300° C. at the rate of 5° C./min under an atmosphere of nitrogen flow at 200 mL/min. This method was used for TG analysis of Form II of Compound 1, Form III of Compound 1, Form V of Compound 1, Form VI of Compound 1, Form VII of Compound 1, Form VIII of Compound 1, Form IX of Compound 1, and Form X of Compound 1.

TGA-DSC

DSC/TGA analysis was performed using a Mettler-Toledo TGA/DSC3+ analyzer. Temperature calibration was performed using calcium oxalate, indium, tin, and zinc. The sample was placed in an aluminum pan. The sample was sealed, the lid pierced, then inserted into the TG furnace. Samples sealed, the lids pierced, and then inserted into the TG furnace and the furnace was heated from 25° C. to 350° C. at the rate of 10° C./min. under an atmosphere of nitrogen flow at 50 mL/min. This method was used for TGA-DSC analysis of Form XI of Compound 1 and Form XII of Compound XII. The term "about" when used in reference to TGA or DSC values means a range of ±2° C.

High Performance Liquid Chromatography (HPLC)

Substance contents in test solutions were measured using HPLC Prominence/PDA detector (Shimadzu Corporation). The analytical conditions and calculation formula were as follows:

| Analytical conditions | |
|---|---|
| Instruments: | HPLC Prominence /PDA detector (Shimadzu) |
| Detection: | UV 200-300 nm (Analyzed at 250 nm) |
| Column: | Inertsil ODS-4, 3 µm, 4.6 mm i.d. × 7.5 cm (GL Sciences Corporation) |
| Column Temp. | 40° C. |
| Mobile Phase A: | A mixture of 0.05 mol/L phosphate buffer (pH 2.0), acetonitrile and tetrahydrofuran (31:6:3 v/v/v) |
| Mobile Phase B: | A mixture of acetonitrile and 0.05 mol/L phosphate buffer (pH 2.0) (3:2 v/v) |

| Gradient Program: | | | |
|---|---|---|---|
| Time(min.) | Mobile Phase A(%) | Mobile Phase B(%) | Elution |
| 0-16 | 100 | 0 | isocratic |
| 16-16.1 | 100→0 | 0→100 | linear gradient |
| 16.1-19 | 0 | 100 | isocratic |
| 19-19.1 | 0→100 | 100→0 | linear gradient |
| 19.1-25 | 100 | 0 | re-equilibration |

| | |
|---|---|
| Flow Rate: | 1.0 mL/min |
| Injection volume: | 10 µL |
| Run time: | 25 minutes |
| Sample Temp: | 25° C. |
| Formula: | $SS_{ssssssssssss} = \dfrac{AA_{ssssssssssss}}{AA_{sssss}} \times C_{ssssss} \times DD_{ssssssssssss}$ |

S: solubility, C: concentration, A: area, Std: standard, D: dilution ratio

Preparation and Characterization of Crystalline Forms of Compound 1

Amorphous Form of Compound 1

The disclosure provides a method for preparing an amorphous form of Compound 1. Form I of Compound 1 was dissolved in an approximately 1:24 ratio (v/v) of dimethyl sulfoxide and 1,4-dioxane. The dimethyl sulfoxide and 1,4-dioxane were then evaporated by vacuum freeze drying to afford the amorphous powder form of Compound 1. The amorphous form of Compound 1 can be prepared using Compound 1 prepared as described in U.S. Pat. Nos. 7,300,935, 8,058,280, 8,735,401, and 9,346,822, hereby incorporated by reference in their entireties.

Form I of Compound 1

The disclosure provides methods for preparing Form I of Compound 1. Form I of Compound 1 may be made by dissolving Form V of Compound 1 in DMSO at a temperature of about 35° C.+/−5° C. Ethanol is then added to the mixture. The mixture is then filtered and the solid washed with ethanol while maintaining the temperature of the mixture at about 35° C.+/−5° C. and the mixture is stirred at about 35° C.+/−5° C. for about one hour, cooled to about 25° C.+/−5° C. and stirred for about 12 hours or more. The resulting precipitate affords Form I of Compound 1.

Form II of Compound I

The disclosure provides several methods for preparing Form II of Compound 1.

Method 1: About 0.3 mL of a DMF solution of Form I of Compound 1 was added to 5 mL of acetone at room temperature (DMF:acetone, 6:94, v/v). The mixture was stirred at a temperature of about −15° C. to about −25° C. for about 3 days when a white suspension consisting of fibers was observed. The solids were isolated by vacuum filtration and vacuum dried at about 60° C. for about 4 hours, resulting in Form II of Compound 1.

Method 2: About 1 g of Form I of Compound 1 was dissolved in 2.6 mL of an 80:20 mixture of DMF:acetone at about 40° C. Acetone at room temperature was added to the mixture to reach a DMF:acetone ratio of about 12.5:87.5, v/v. The mixture was then seeded with about 0.5% (wt) of crystals of Form II. The mixture was placed in a freezer at about −15° C. to about −25° C. overnight, after which the resulting suspension was vacuum filtered and the wet cake was washed with cold acetone and dried under vacuum at about 62° C. to about 65° C. for about 5 hours. Solids were consistent with Form II of Compound 1; yield 78.5%.

Method 3: About 1 g of Form 1 of Compound 1 was dissolved in 2.2 mL of DMF at about 40° C. Acetone at room temperature was added to the mixture to reach a DMF: acetone ratio of about 10:90, v/v. The mixture was then seeded with about 0.5% (wt) of Form II. The mixture was placed in a freezer at about −15° C. to about −25° C. overnight, after which the resulting suspension was vacuum filtered and the wet cake was washed with cold acetone and dried under vacuum at about 62° C. to about 65° C. for about 5 hours. Solids were consistent with Form II of Compound 1; yield 77.5%.

Form III of Compound 1

The disclosure provides a method for preparing Form III of Compound 1. Form I of Compound 1 was dissolved in DMF and then precipitated with water at about −10° C. (DMF:H₂O 42:58). The mixture was then seeded with Form II and the resulting slurry was stored at about −10° C. for three days whereupon a thick, white mobile suspension was observed. Solids were consistent with Form III as determined by XRPD.

Form IV of Compound 1

The disclosure provides a method for preparing Form IV of Compound 1. Form III of Compound I was transformed to anhydrate Form IV by heating Form III to between about 79° C. and about 197° C.

Form V of Compound 1

The disclosure provides a method for preparing Form V of Compound 1. The amorphous form of Compound 1 was dissolved into toluene to make an approximately 10 mg/mL solution at about 55° C. The toluene was then evaporated by nitrogen flow at about 55° C. to afford powder Form V of Compound 1.

Form VI of Compound 1

The disclosure provides a method for preparing Form VI of Compound 1. The amorphous form of Compound 1 was dissolved into anisole to make an approximately 10 mg/mL solution at about 55° C. An approximately equivalent volume of heptane was added into the anisole solution to make an approximately 5 mg/mL solution at about 55° C. The anisole and heptane were evaporated by nitrogen flow at about 55° C. to afford powder Form VI of Compound 1.

Form VII of Compound 1

The disclosure provides a method for preparing Form VII of Compound 1. The amorphous form of Compound 1 was dissolved into 2-propanol to make an approximately 10 mg/mL solution at about 55° C. An approximately 2.5 times volume of water was added into the 2-propanol solution to make an approximately 2.9 mg/mL solution at about 55° C. The solution was cooled from about 55° C. to about 10° C. at a rate of about 3° C./hour with stirring at about 500 rpm. The crystallized solid in suspension was collected by vacuum filtration using a filter (Millipore JGWP 0.2 µm) to afford powder Form VII of Compound 1.

Form VIII of Compound 1

The disclosure provides a method for preparing Form VIII of Compound 1. Form I of Compound 1 was dispersed into a mixture of 1,4-dioxane and water (about 1:1, v/v) to make slurry conditions at a concentration of about 20 mg/mL. The slurry was aged by stirring for about three days at about 25° C. The dispersed powder was collected by vacuum filtration using a filter (Millipore JGWP 0.2 µm) to afford powder Form VIII of Compound 1.

Form IX of Compound 1

The disclosure provides a method for preparing Form IX of Compound 1. The amorphous form of Compound 1 was dissolved into α,α,α-trifluorotoluene to make an approximately 10 mg/mL solution at about 55° C. An approximately equivalent volume of heptane was added into the α,α,α-trifluorotoluene solution to make an approximately 5 mg/mL solution at about 55° C. The α,α,α-trifluorotoluene and heptane were evaporated by nitrogen flow at about 55° C. to afford powder Form IX of Compound 1.

Form X of Compound 1

The disclosure provides a method for preparing Form X of Compound 1. The amorphous form of Compound 1 was dissolved into trifluoroethanol to make an approximately 200 mg/mL solution at about 55° C. An approximately equivalent volume of diisopropylether was added into the trifluoroethanol solution to make an approximately 100 mg/mL solution at about 55° C. The solution was cooled from about 55° C. to about 10° C. at a rate of about 3° C. per hour with stirring at about 500 rpm. The crystallization solid in suspension was collected by vacuum filtration using a filter (Millipore JGWP 0.2 µm) to afford powder Form X of Compound 1.

Form XI of Compound 1

The disclosure provides several methods for preparing Form XI of Compound 1.

Method 1: Form I of Compound 1 (~100 mg) was dissolved in 0.5 mL of DMF at ambient temperature. The resulting clear solution was cooled to about −10° C. with no precipitation observed. Aliquots of methyl tert-butyl ether (MTBE) were added to reach a DMF:MTBE 50:50 volume ratio and seeds of Form II of Compound 1 were added resulting in a hazy solution. An additional amount of MTBE was added to reach a DMF:MTBE 25:75 volume ratio, with no visual change observed. The hazy solution was stirred at about −10° C. overnight, producing a white mobile suspension. After a total of about 4 days of stirring at about −10° C., the solids were isolated cold by vacuum filtration using a funnel conditioned on dry ice and washed with cold MTBE conditioned in a freezer at about −15° C. to about −25° C. to afford Form XI of Compound 1.

Method 2: Form I of Compound 1 (~100 mg) was dissolved in 0.5 mL of DMF at ambient temperature. The resulting clear solution was cooled to about −10° C. with no precipitation observed. Aliquots of isopropanol were added to reach a DMF:isopropanol 50:50 volume ratio and seeds of Form II of Compound 1 were added resulting in a hazy solution. The hazy solution became a thin suspension within a half hour and was allowed to stir at about −10° C. overnight producing a white slightly dense mobile suspension. After a total of about 4 days of stirring at about −10° C., the solids of the resulting milky thick suspension were diluted with 0.5 mL of cold isopropanol conditioned in a freezer at about −15° C. to about −25° C. and were isolated cold by vacuum filtration using a funnel conditioned on dry ice to afford Form XI of Compound 1.

Form XII of Compound 1

The disclosure provides methods for preparing Form XII of Compound 1.

Method 1: Form I of Compound 1 (~100 mg) was dissolved in 0.3 mL of DMF at ambient temperature. The resulting clear solution was added dropwise with stirring into 5.0 mL of acetone without causing precipitation. The DMF:acetone volume ratio was calculated to be 6:94. The clear solution was allowed to stir at about −15° C. to about −25° C. for about 2 days, resulting in a hazy solution that was stirred additionally for 1 day, producing a white suspension. The solids were isolated cold by vacuum filtration using a funnel conditioned on dry ice to afford Form XII of Compound 1.

Method 2: Form I of Compound 1 (~1.0 g) was slurried in 2.0 mL of DMF:acetone 80:20 (v/v) at about 40° C. Additional aliquots of DMF were added until complete dissolution was observed, reaching a DMF:acetone 85:15 (v/v) ratio. The resulting clear solution was placed on a stirrer at ambient temperature and acetone was added slowly to reach a DMF:acetone 12.5:87.5 (v/v) ratio, with no visual change observed. The clear solution was seeded with 0.45 wt % of Form II of Compound 1, producing a hazy solution that was placed in a freezer at about −15° C. to about −25° C. overnight. The solids were isolated cold by vacuum filtration using a funnel conditioned in a freezer at about −15° C. to about −25° C. The solids were washed with cold acetone also conditioned in a freezer at about −15° C. to about −25° C. to afford Form XII of Compound 1.

Method 3: Form I of Compound 1 (~1.0 g) was slurried in 1.0 mL of DMF at about 40° C. Additional aliquots of DMF totaling 1.2 mL were added until complete dissolution was observed. The resulting clear solution was placed on a stirrer at ambient temperature and acetone was added slowly to reach a DMF:acetone 11:89 (v/v) ratio, with no visual change observed. The clear solution was seeded with 0.5 wt % of Form II of Compound 1, producing a hazy solution. Additional acetone (1 mL) was added to reach a DMF:acetone 10:90 (v/v) ratio and the sample was allowed to stir at ambient temperature, producing a white suspension that was placed in a freezer at about −15° C. to about −25° C. overnight. The solids were isolated cold by vacuum filtration and washed with cold acetone to afford Form XII of Compound 1. Both the acetone and funnel were conditioned in a freezer at about −15° C. to about −25° C. prior to use.

XRPD Characterization of the Crystalline Forms of Compound 1

XRPD data for the crystalline forms of Compound 1 disclosed herein were collected as detailed above. The XRPD patterns for the crystalline forms are detailed in FIG. 1 (Form II of Compound 1), FIG. 4 (Form III of Compound 1), FIG. 7 (Form V of Compound 1), FIG. 10 (Form VI of Compound 1), FIG. 13 (Form VII of Compound 1), FIG. 16 (Form VIII of Compound 1), FIG. 19 (Form IX of Compound 1), FIG. 22 (Form X of Compound 1), FIG. 30 (Form XI of Compound 1), and FIG. 32 (Form XII of Compound 1). The peaks present in these XRPD patterns are listed in Table 2 above. All peak listings are in degrees 2θ±0.2° 2θ.

Figure 26:
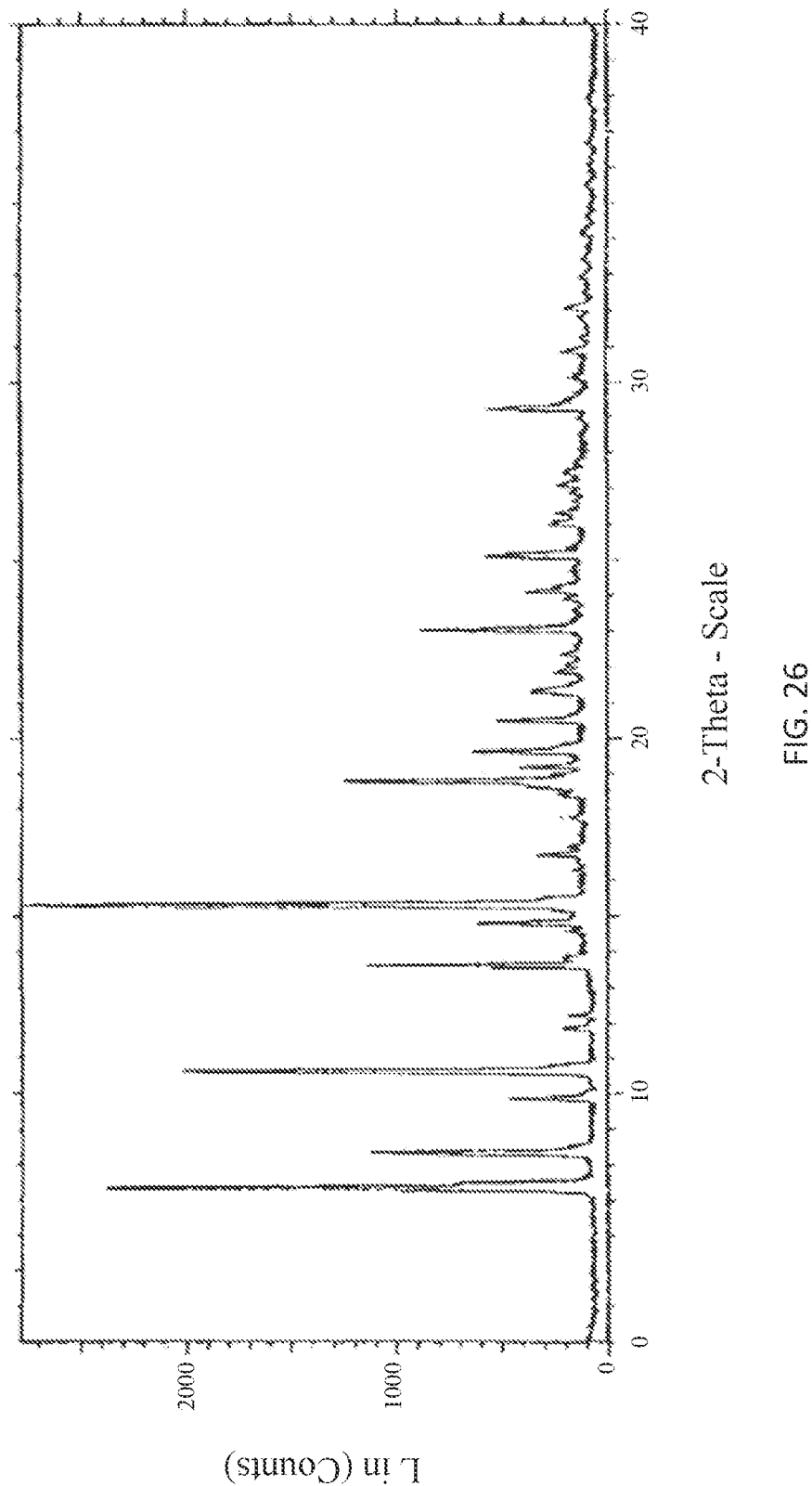
FIG. 26 depicts a powder X-ray diffraction pattern of a crystal of a tetrahydrofuran solvate of Compound 1. Adapted from FIG. 1 of U.S. Pat. No. 9,758,528.

FIG. 25 depicts a powder X-ray diffraction pattern of Form I of Compound 1. FIG. 26 depicts a powder X-ray diffraction pattern of a crystal of a tetrahydrofuran solvate of Compound 1.

GC Characterization of the Crystalline Forms of Compound 1

GC results of the crystallization solvent present in Forms V-X are shown in the following Table:

Solvent Contents of Forms V-X

| Sample name | Crystallization solvent | ppm |
| --- | --- | --- |
| Form V | Toluene | 79520 |
| Form VI | Anisole/heptane | 100750/130 |
| Form VII | 2-propanol/(water) | 94230 |
| Form VIII | 1,4-dioxane/(water) | 131880 |
| Form IX | α,α,α-trifluorotoluene/heptane | 11360/30 |
| Form X | Trifluoroethanol/diisopropylether | 165920/5330 |

The detected amounts of solvents by GC indicated that Forms V-X are the hemi- or mono-solvates of Compound 1.

Karl Fischer (KF) Titration of Form III

As determined by KF titration, the water content in hemihydrate Form A was 1.3%, which is the equivalent of a hemihydrate.

Thermal Analyses (DSC and TG)

DSC and TG data for the crystalline forms of Compound 1 disclosed herein were collected as detailed above. The TG thermograms for the crystalline forms are detailed in FIG. 2 (Form II of Compound 1), FIG. 5 (Form III of Compound 1), FIG. 8 (Form V of Compound 1), FIG. 11 (Form VI of Compound 1), FIG. 14 (Form VII of Compound 1), FIG. 17 (Form VIII of Compound 1), FIG. 20 (Form IX of Compound 1), FIG. 23 (Form X of Compound 1), FIG. 31 (top panel, Form XI of Compound 1), and FIG. 33 (top panel, Form XII of Compound 1). The DSC thermograms for the crystalline forms are detailed in FIG. 3 (Form II of Compound 1), FIG. 6 (Form III of Compound 1), FIG. 9 (Form V of Compound 1), FIG. 12 (Form VI of Compound 1), FIG. 15 (Form VII of Compound 1), FIG. 18 (Form VIII of Compound 1), FIG. 21 (Form IX of Compound 1), FIG. 24 (Form X of Compound 1), FIG. 31 (bottom panel, Form XI of Compound 1), and FIG. 33 (bottom panel, Form XII of Compound 1). The thermal events in the DSC and TG of the crystalline forms of Compound 1 are detailed in the tables below.

Thermal Events in DSC and TG of Form II

| Thermal events | T (onset, ° C.) | T (peak top, ° C.) |
| --- | --- | --- |
| Melting point (degradation) | (180) | (187) |
| Degradation | 175 | 208 |
| Exotherm of degradation | — | 192 |

Thermal Events in DSC and TG of Form III

| Thermal events | T (onset, ° C.) | T (peak top, ° C.) |
| --- | --- | --- |
| Dehydrate and transformation to anhydrate Form C | 52 | 79 |
| Melting point of Form C (degradation) | (197) | (201) |
| Degradation | 183 | 215, 250 |
| Exotherm of degradation (crystallization of anhydrate Form A) | — | 205 |
| Exotherm of degradation | — | 240 |

Thermal Events in DSC and TG of Form V

| Thermal events | T (onset, ° C.) | T (peak top, ° C.) |
| --- | --- | --- |
| Volatilization of tiny residual solvent | 36 | 39, 66 |
| Desolvation | — | 163 |
| Melting point (degradation) | (145) | (153) |
| Degradation | 163 | 202 |
| Exotherm of degradation | — | 198 |

Thermal Events in DSC and TG of Form VI

| Thermal events | T (onset, ° C.) | T (peak top, ° C.) |
| --- | --- | --- |
| Volatilization of tiny residual solvent | — | 66 |
| Desolvation | — | 158 |
| Melting point (degradation) | (143) | (147) |
| Degradation | 158 | 201 |
| Exotherm of degradation | — | 155, 198 |

Thermal Events in DSC and TG of Form VII

| Thermal events | T (onset, ° C.) | T (peak top, ° C.) |
| --- | --- | --- |
| Volatilization of tiny residual solvent | — | 92, 122 |
| Desolvation | — | 161 |
| Melting point (degradation) | (136) | (147) |
| Degradation | 161 | 205 |
| Exotherm of degradation | — | 179 |

Thermal Events in DSC and TG of Form VIII

| Thermal events | T (onset, ° C.) | T (peak top, ° C.) |
|---|---|---|
| Volatilization of tiny residual solvent | — | 122 |
| Desolvation | — | 155 |
| Melting point (degradation) | (139, 161) | (150, 169) |
| Degradation | 155 | 195 |
| Exotherm of degradation | — | 194 |

Thermal Events in DSC and TG of Form IX

| Thermal events | T (onset, ° C.) | T (peak top, ° C.) |
|---|---|---|
| Volatilization of tiny residual solvent | — | 104, 133 |
| Melting point (degradation) | (135) | (156) |
| Degradation | — | 157 |
| Exotherm of degradation | — | 182 |

Thermal Events in DSC and TG of Form X

| Thermal events | T (onset, ° C.) | T (peak top, ° C.) |
|---|---|---|
| Volatilization of tiny residual solvent | — | 82 |
| Desolvation | — | 159 |
| Melting point (degradation) | (124) | (142) |
| Degradation | 159 | 197 |
| Exotherm of degradation | — | 190 |

Thermal Events in DSC and TG of Form XI

| Thermal events | Result |
|---|---|
| DSC | Large endotherm with peak maximum at ~178.3° C. and onset at 171.2° C. |
| TG | Negligible weight loss of 0.06% between 35° C. and 110° C. and a small weight loss of 1.4% between 110° C. and 155° C. followed by an additional weight loss of 8.5% between 155° C. and 209° C. that coincided with the potential melt |

Thermal Events in DSC and TG of Form XII

| Thermal events | Result |
|---|---|
| DSC | Broad endotherm at 136.7° C. Large endotherm at 189.0° C. (onset 181.1° C.) |
| TG | 0.29% wt loss at 35-100° C. 3.59% wt loss at 101-170° C. |

Solubility Determination of Forms I and II of Compound 1

The thermodynamic solubility of Forms I and II was determined at pH 1.2 and pH 6.8 and in 20 mM GCDC, pH 6.8 at 37° C. with an equilibrium period for 2, 6 and 24 hours. The average of solubility (n=3) is summarized in Tables 3 and 4 above. Form I exhibited lower solubility than Form II at pH 6.8 and in 20 mM GCDC, pH 6.8, while all crystal forms were extremely soluble at pH 1.2.

We claim:

1. A crystalline form of an isopropyl alcohol solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea.

2. The crystalline form of claim 1, characterized by an X-ray powder diffraction pattern comprising at least three 2-theta (2θ+0.2° 2θ) peaks selected from 8.4°, 10.6°, 13.6°, 15.4° and 18.8°.

3. The crystalline form of claim 1, characterized by an X-ray powder diffraction pattern comprising 2-theta (2θ+0.2° 2θ) peaks at 8.4°, 10.6°, 13.6°, 15.4° and 18.8°.

4. The crystalline form of claim 1, characterized by an X-ray powder diffraction pattern substantially the same as the pattern shown in FIG. 13.

5. The crystalline form of claim 1, characterized by a thermogravimetric (TG) thermogram substantially the same as the pattern shown in FIG. 14.

6. The crystalline form of claim 1, characterized by a differential scanning calorimetry (DSC) thermogram comprising an endothermic peak at about 147° C.

7. The crystalline form of claim 1, characterized by a DSC thermogram substantially the same as the pattern shown in FIG. 15.

8. A crystalline form of a dimethylformamide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea that exhibits an X-ray powder diffraction pattern comprising at least three 2-theta (2θ+0.2° 2θ) peaks selected from 7.0°, 10.3°, 10.5°, 13.0°, 18.4° and 20.8°.

9. The crystalline form of claim 8, wherein the X-ray powder diffraction pattern comprises at least five 2-theta (2θ+0.2° 2θ) peaks selected from 7.0°, 10.3°, 10.5°, 13.0°, 18.4° and 20.8°.

10. The crystalline form of claim 8, characterized by an X-ray powder diffraction pattern substantially the same as the pattern shown in FIG. 30.

11. The crystalline form of claim 8, characterized by a TG thermogram substantially the same as the pattern shown in FIG. 31, top panel.

12. The crystalline form of claim 8, characterized by a DSC thermogram comprising an endothermic peak at about 178° C.

13. The crystalline form of claim 8, characterized by a DSC thermogram substantially the same as the pattern shown in FIG. 31, bottom panel.

14. A crystalline form of an acetone solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea.

15. The crystalline form of claim 14, characterized by an X-ray powder diffraction pattern comprising at least three 2-theta (2θ+0.2° 2θ) peaks selected from 10.3°, 10.6°, 11.1°, 13.0°, 15.7°, 18.4°, 19.1°, 20.3° and 20.7°.

16. The crystalline form of claim 14, characterized by an X-ray powder diffraction pattern comprising at least five 2-theta (2θ+0.2° 2θ) peaks selected from 10.3°, 10.6°, 11.1°, 13.0°, 15.7°, 18.4°, 19.1°, 20.3° and 20.7°.

17. The crystalline form of claim 14, characterized by an X-ray powder diffraction pattern substantially the same as the pattern shown in FIG. 32.

18. The crystalline form of claim 14, characterized by a TG thermogram substantially the same as the pattern shown in FIG. 33, top panel.

19. The crystalline form of claim 14, characterized by a DSC thermogram comprising an endothermic peak at about 189° C.

20. The crystalline form of claim 14, characterized by a DSC thermogram substantially the same as the pattern shown in FIG. 33, bottom panel.

* * * * *